(12) United States Patent
Sabatini et al.

(10) Patent No.: US 11,571,441 B2
(45) Date of Patent: Feb. 7, 2023

(54) SIDEROFLEXINS AS MITOCHONDRIAL SERINE TRANSPORTERS

(71) Applicant: Whitehead Institute for Biomedical Research, Cambridge, MA (US)

(72) Inventors: David M. Sabatini, Cambridge, MA (US); Nora Kory, Allston, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 17/042,875

(22) PCT Filed: Mar. 26, 2019

(86) PCT No.: PCT/US2019/024152
§ 371 (c)(1),
(2) Date: Sep. 28, 2020

(87) PCT Pub. No.: WO2019/191148
PCT Pub. Date: Oct. 3, 2019

(65) Prior Publication Data
US 2021/0268015 A1    Sep. 2, 2021

Related U.S. Application Data

(60) Provisional application No. 62/731,056, filed on Sep. 13, 2018, provisional application No. 62/648,363, filed on Mar. 26, 2018.

(51) Int. Cl.
*C07H 21/04*       (2006.01)
*A61K 31/713*      (2006.01)
*G01N 33/574*      (2006.01)
*C12N 9/22*        (2006.01)
*C12N 15/11*       (2006.01)
*C12N 15/113*      (2010.01)
*A61P 35/04*       (2006.01)

(52) U.S. Cl.
CPC ............. *A61K 31/713* (2013.01); *C12N 9/22* (2013.01); *C12N 15/111* (2013.01); *C12N 15/113* (2013.01); *G01N 33/57492* (2013.01); *A61P 35/04* (2018.01); *C12N 2310/20* (2017.05); *G01N 2500/10* (2013.01); *G01N 2500/20* (2013.01)

(58) Field of Classification Search
CPC .......................... C12N 15/113; C12N 2310/20
See application file for complete search history.

(56) References Cited

U.S. PATENT DOCUMENTS

| 2014/0314786 A1 | 10/2014 | Condeelis et al. |
| 2017/0247710 A1* | 8/2017 | Nagaraju ............... C12N 15/74 |
| 2019/0271702 A1* | 9/2019 | Poupot .................... A61P 35/02 |

FOREIGN PATENT DOCUMENTS

| CN | 1448402 A | 10/2003 |
| WO | WO 2018/019990 A1 | 2/2018 |
| WO | WO 2018/129421 A1 | 7/2018 |

OTHER PUBLICATIONS

Kory, Nora, et al. "SFXN1 is a mitochondrial serine transporter required for one-carbon metabolism." Science 362.6416 (2018).
Fleming, Mark D., et al. "A mutation in a mitochondrial transmembrane protein is responsible for the pieiotropic hematological and skeletal phenotype of flexed-taii (f/f) mice." Genes & development 5.6 (2001): 652-657.
International Search Report issued in PCT/US2019/024152, dated Jul. 15, 2019.

* cited by examiner

*Primary Examiner* — Amy H Bowman
(74) *Attorney, Agent, or Firm* — Morse, Barnes-Brown & Pendleton, P.C.; Lisa M. Warren, Esq.; Erin E. Bryan, Esq.

(57) ABSTRACT

In some aspects, the disclosure provides methods for modulating mitochondrial transport of serine in a cell, the methods comprising modulating expression or activity of one or more sideroflexins. In some aspects, methods of identifying agents that modulate sideroflexin expression or activity are provided. In some aspects, methods of treating cancer are provided.

17 Claims, 40 Drawing Sheets

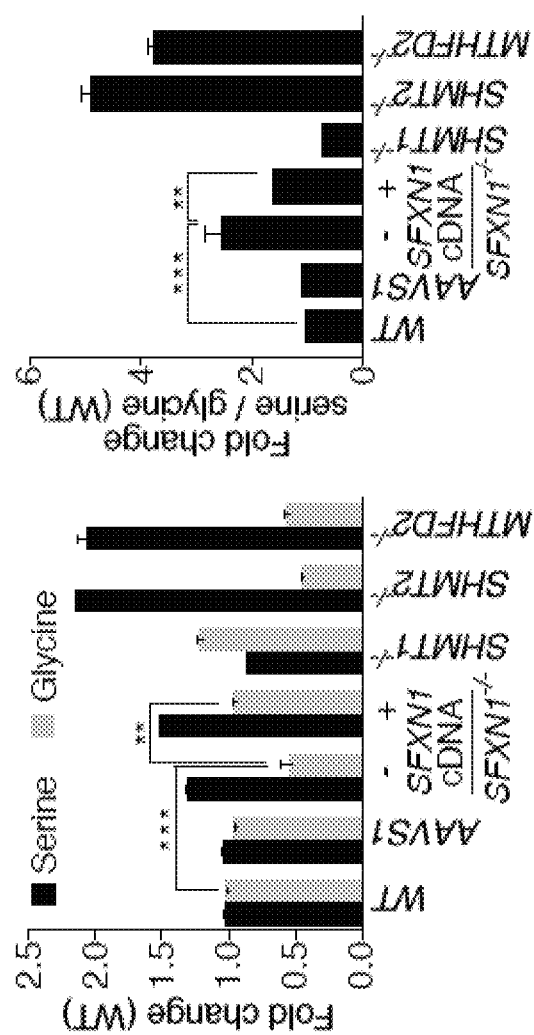
FIG. 2N
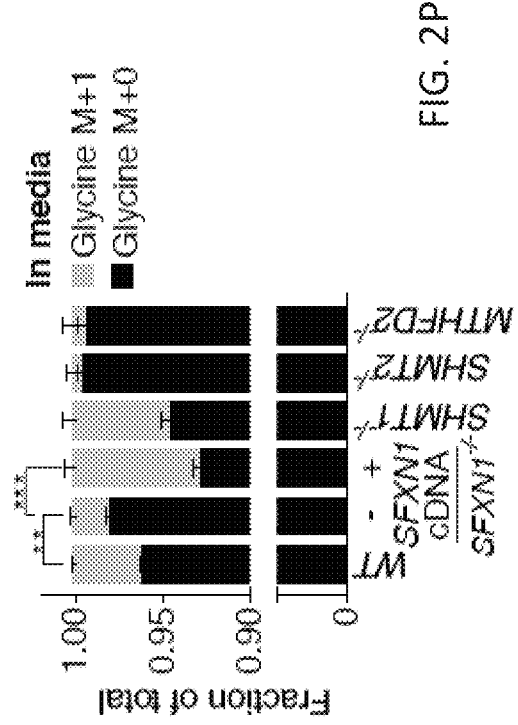
FIG. 2O
FIG. 2P

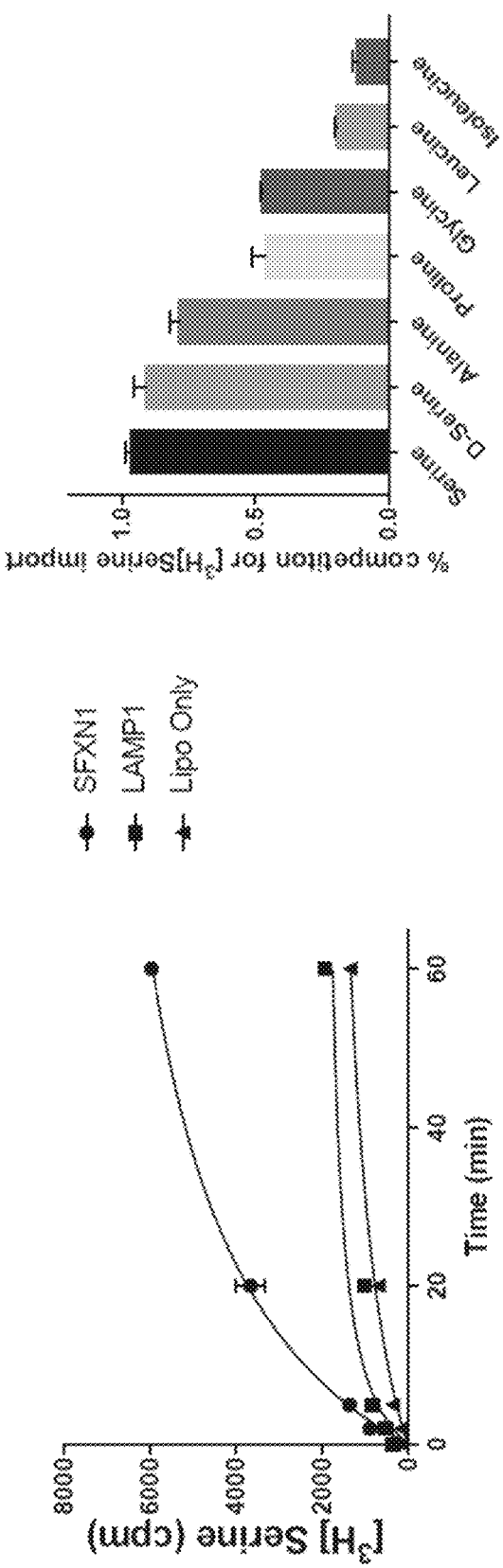
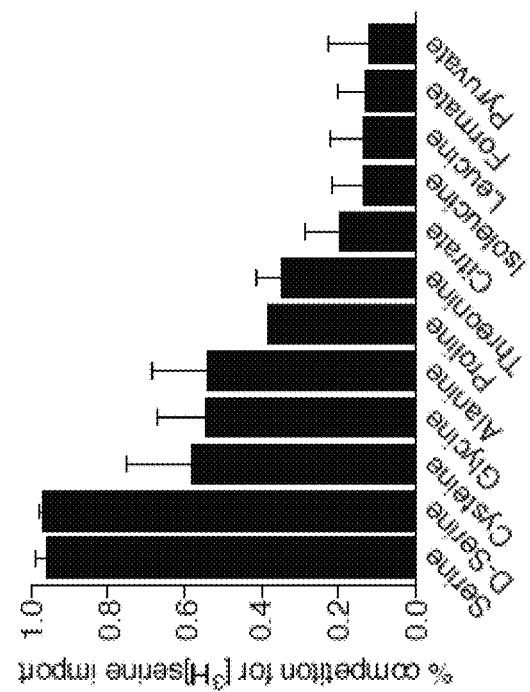
FIG. 3A
FIG. 3B
FIG. 3C

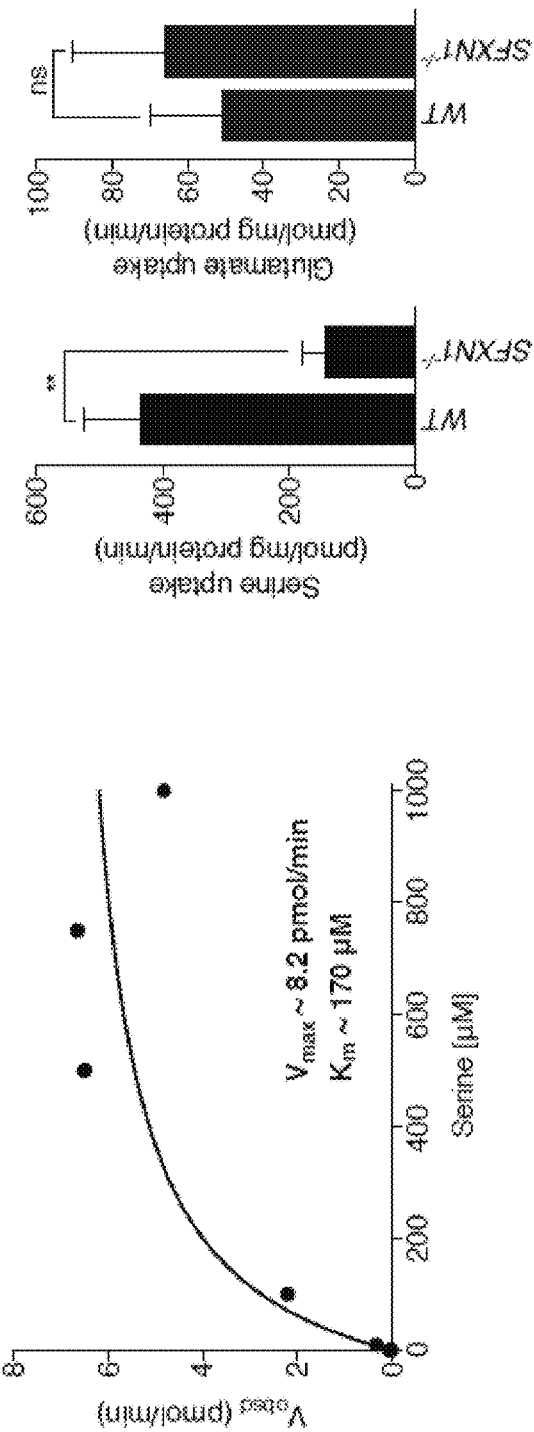
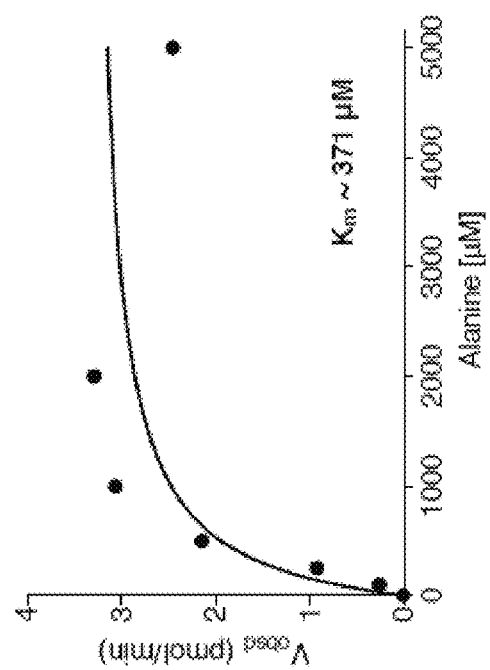
FIG. 3D
FIG. 3E
FIG. 3F

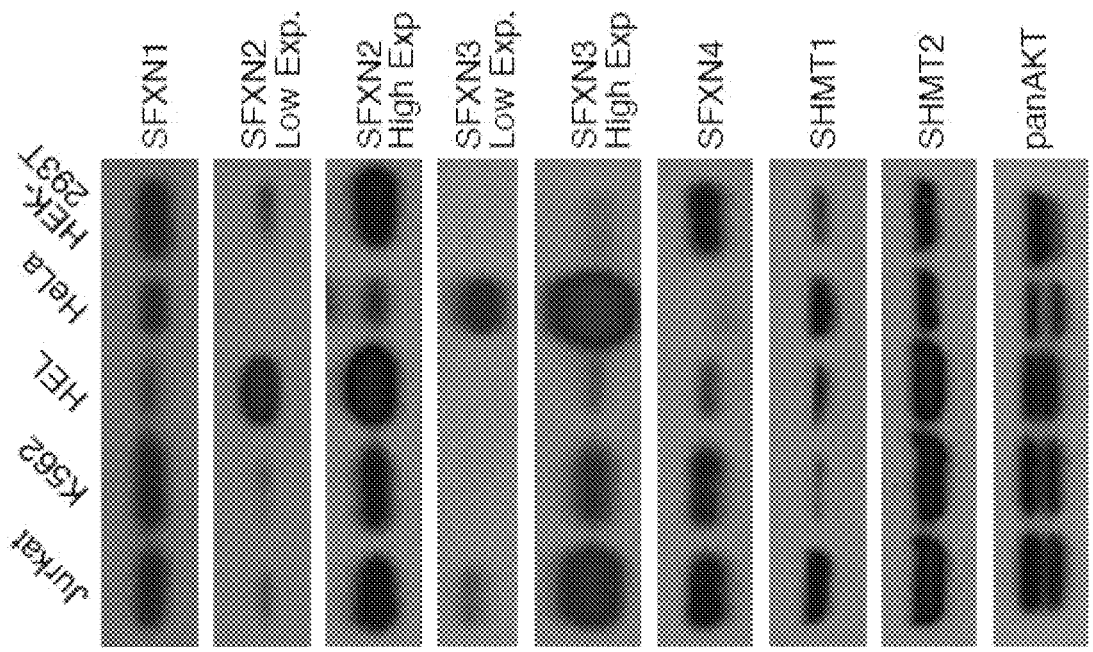
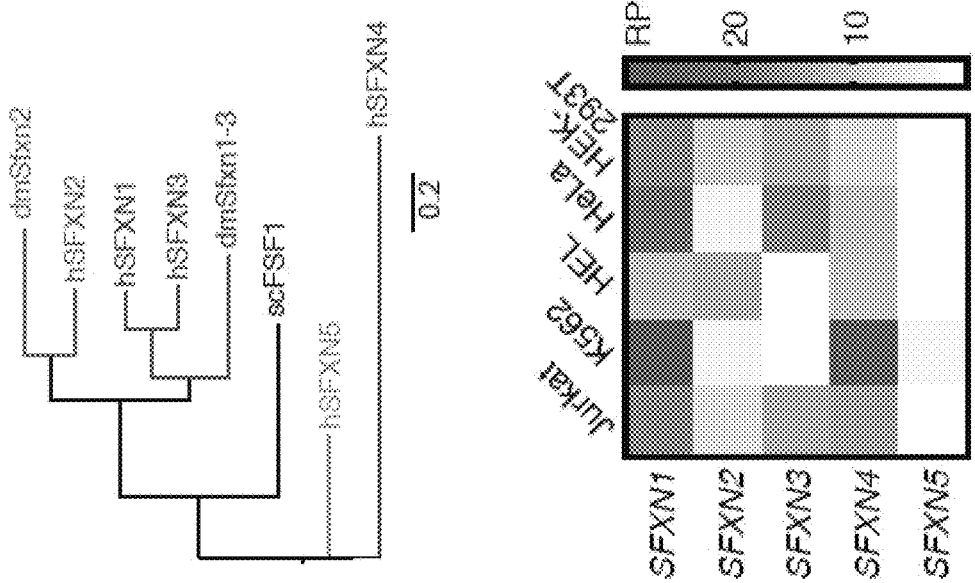
FIG. 4C
FIG. 4A
FIG. 4B

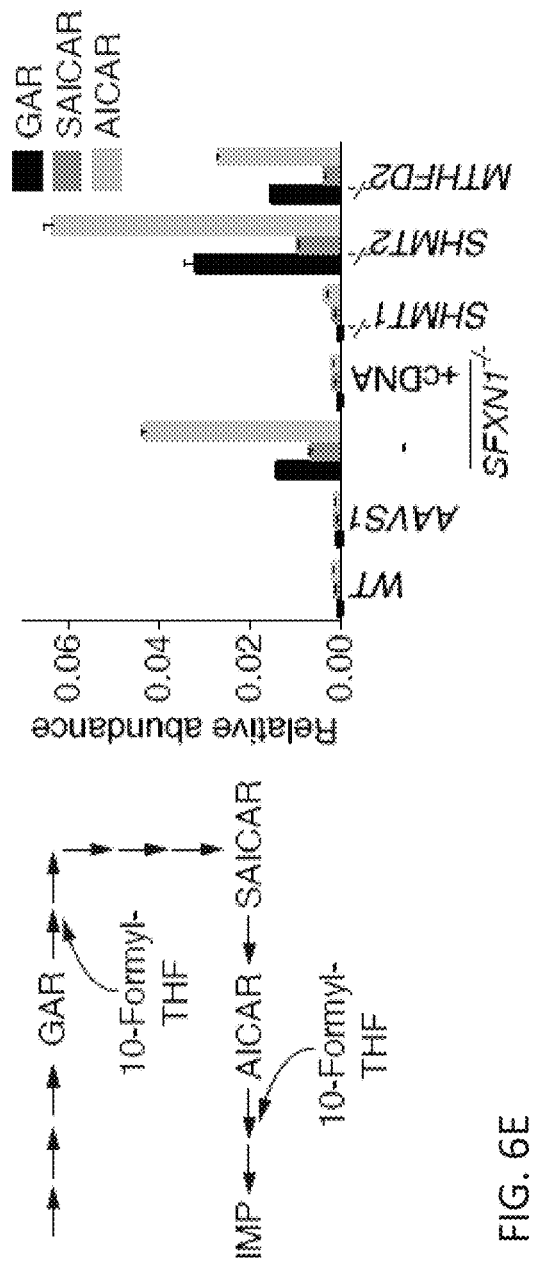
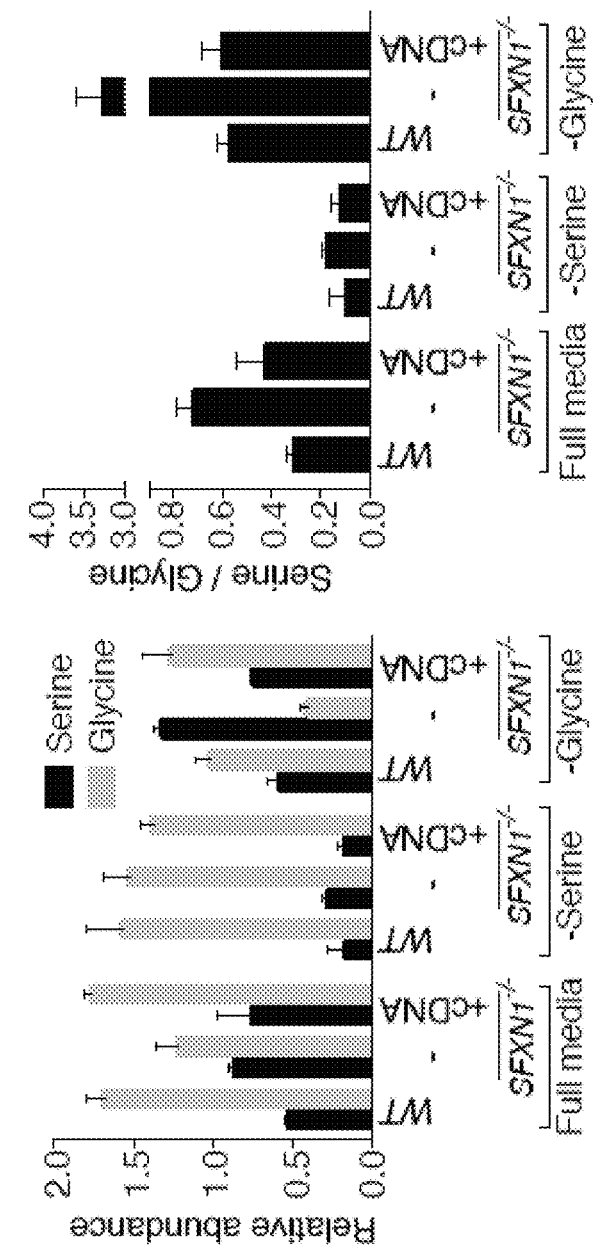

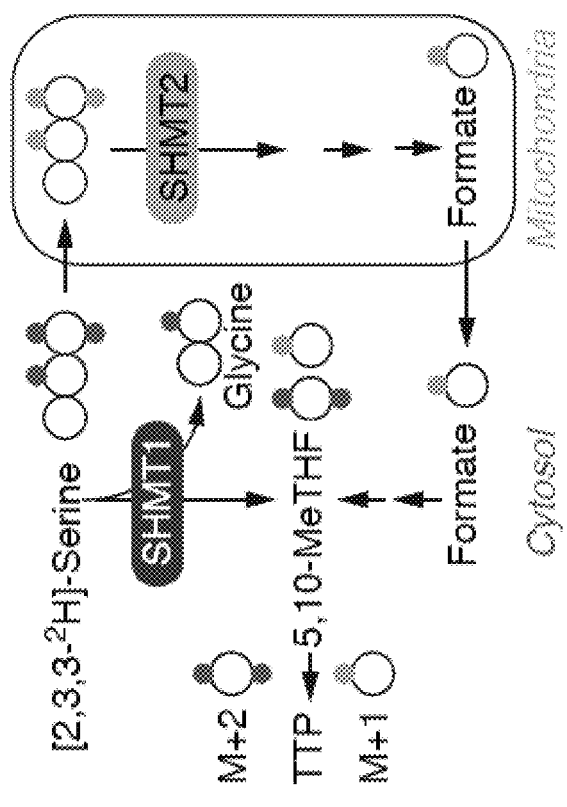
FIG. 6F
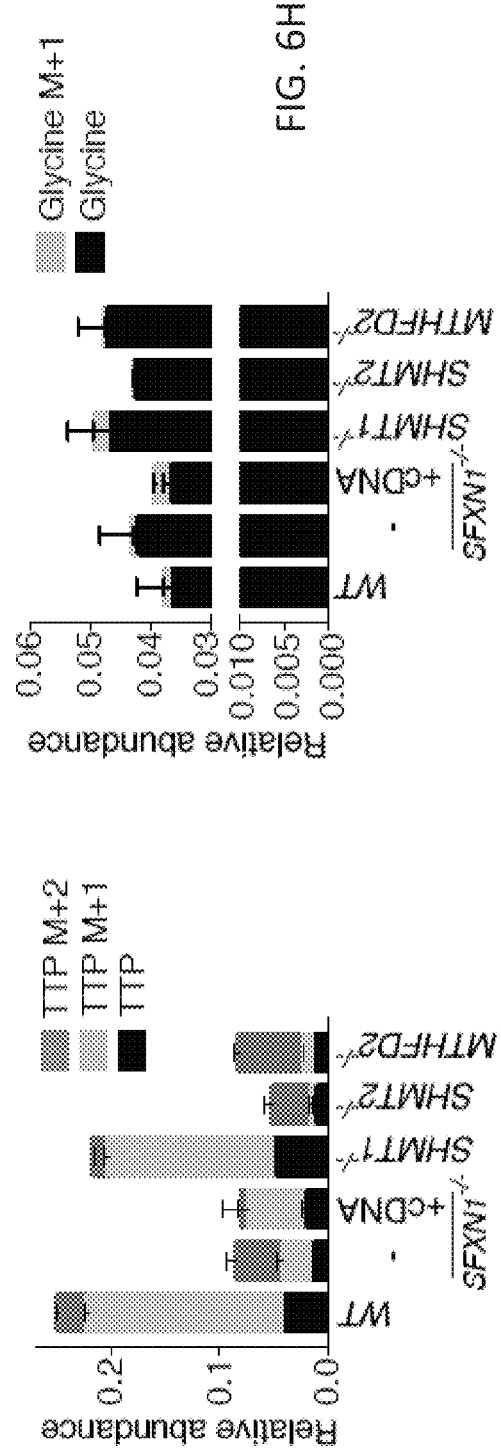
FIG. 6H
FIG. 6G

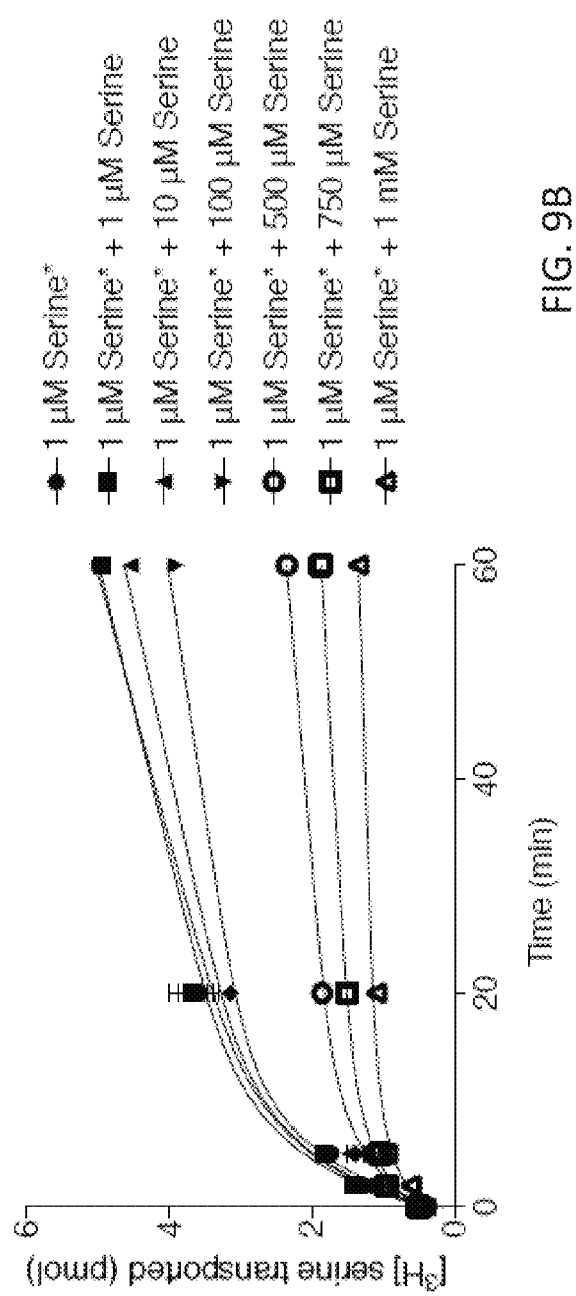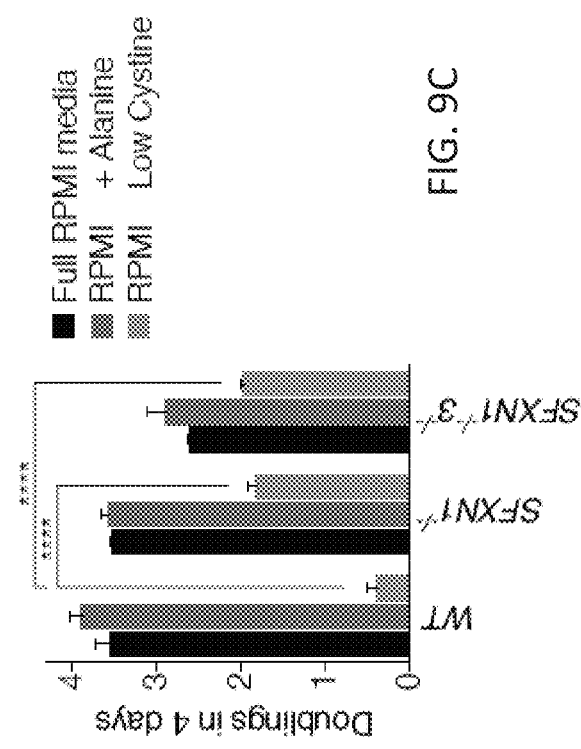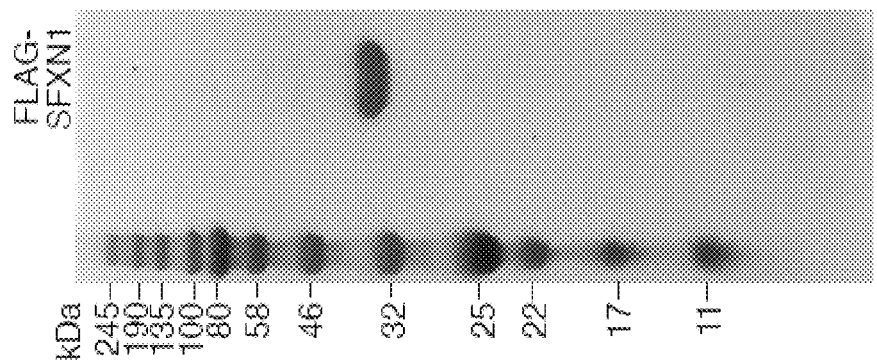
FIG. 9A
FIG. 9B
FIG. 9C

SIDEROFLEXINS AS MITOCHONDRIAL SERINE TRANSPORTERS

RELATED APPLICATIONS

This application is a national stage filing under 35 U.S.C. 371 of International Application No. PCT/US2019/024152, filed Mar. 26, 2019, which claims the benefit of U.S. Provisional Application Ser. No. 62/731,056, filed Sep. 13, 2018, and U.S. Provisional Application Ser. No. 62/648,363, filed Mar. 26, 2018, the contents of which are hereby incorporated by reference in their entirety. International Application No. PCT/US2019/024152 was published under PCT Article 21(2) in English.

BACKGROUND OF THE INVENTION

The one-carbon metabolism pathway generates reactive one-carbon units used in the biosynthesis of nucleotides, proteins, and lipids. Flux through the pathway is especially critical in rapidly dividing cells, including cancer cells, and not only generates biomass, but also maintains redox homeostasis and epigenetic gene regulation.

One-carbon metabolism is compartmentalized ((1,2)) with at least one isozyme for each step in the pathway in the cytosol and in mitochondria. In proliferating cells, mitochondrial one-carbon metabolism supplies the majority of one-carbon units for purine synthesis and methylation reactions (3-12) and enzymes in the mitochondrial branch of the pathway are highly expressed in cancer cells (13-15).

The amino acid serine is the major one-carbon donor in most organisms and its contribution to cellular biomass is estimated to be second only to glutamine (16). Serine enters mitochondria, where it is oxidized by serine hydroxymethyltransferase-2 (SHMT2) to glycine and 5,10-methylene-THF (tetrahydrofolate), which is further converted to formate by methylenetetrahydrofolate dehydrogenase-2/2L (MTHFD2/MTHFD2L) and MTHFD1L. Formate then exits mitochondria and is fixed in the cytosol by MTHFD1 to regenerate one-carbon units needed for nucleotide synthesis. While the import of serine into mitochondria is a critical step in the generation of one-carbon units, how it enters mitochondria is not known (3, 17-20).

SUMMARY OF THE INVENTION

In some aspects, the disclosure relates to methods for modulating mitochondrial transport of serine in a cell, the methods comprising modulating expression or activity of one or more sideroflexins. In some aspects, methods of identifying agents that modulate sideroflexin expression or activity are provided. In some aspects, methods of treating cancer are provided.

In some aspects, described herein are methods for modulating mitochondrial transport of serine in a cell, the methods comprising modulating expression or activity of one or more sideroflexins, thereby modulating the mitochondrial transport of serine in the cell.

In some embodiments the one or more sideroflexins is selected from the group consisting of SFXN1, SFXN2, SFXN3, SFXN4, and SFXN5. In some embodiments, the one or more sideroflexins is SFXN1. In some embodiments, the one or more sideroflexins is SFXN1 and SFXN3. The one or more sideroflexins may be a mammalian sideroflexin (e.g., a human sideroflexin).

In some embodiments, modulating of expression or activity of one or more sideroflexins comprises inhibiting expression or activity of one or more sideroflexins. In some embodiments, modulating expression or activity of one or more sideroflexins comprises contacting the cell with an inhibitor of sideroflexin expression or activity. In some embodiments, an inhibitor of sideroflexin expression or activity comprises a small molecule or nucleic acid. In some aspects, the inhibitor comprises an RNAi agent. In some aspects, the inhibitor comprises D-serine. In some embodiments, modulating expression or activity of one or more sideroflexins comprises deleting or mutating the sideroflexin gene. In some aspects, the sideroflexin gene is deleted or mutated using a CRISPR/Cas genome editing system.

In some embodiments the cell is a cancer cell. In some aspects, the cell is a blood cancer cell (e.g., a leukemia cell, lymphoma cell, or multiple myeloma cell). In some aspects, the cell is a carcinoma cell or sarcoma cell. In some aspects, the cell is a brain tumor cell, bladder tumor cell, breast tumor cell, cervical tumor cell, colorectal tumor cell, embryonal tumor cell, gastric tumor cell, germ cell tumor cell, head and neck tumor cell, hematologic tumor cell, kidney tumor cell, melanoma cell, mesothelial tumor cell, ovarian tumor cell, or yolk sac tumor cell. In some embodiments the cell is a breast cancer cell. In some embodiments the cell is a mammalian cell.

In some embodiments the methods disclosed herein further comprise inhibiting expression or activity of SHMT1, SHMT2, and/or MTHFD2. In some embodiments the methods disclosed herein further comprise inhibiting serine synthesis in the cell. In some aspects the modulation of mitochondrial transport of serine in the cell thereby modulates one-carbon metabolism in the cell.

In some aspects, described herein are methods of treating a subject in need of treatment for a cancer, the methods comprising modulating expression or activity of one or more sideroflexins in a cancer cell of the subject.

In some embodiments the one or more sideroflexins is selected from the group consisting of SFXN1, SFXN2, SFXN3, SFXN4, and SFXN5. In some embodiments, the one or more sideroflexins is SFXN1. In some embodiments, the one or more sideroflexins is SFXN1 and SFXN3. The one or more sideroflexins may be a mammalian sideroflexin (e.g., a human sideroflexin).

In some embodiments modulating expression or activity of one or more sideroflexins comprises administering an inhibitor of sideroflexin expression or activity to the subject. In some embodiments an inhibitor sideroflexin expression or activity comprises a small molecule or nucleic acid. In some aspects, the inhibitor comprises an RNAi agent. In some aspects, the inhibitor comprises D-serine.

In some embodiments the cell is a cancer cell. In some aspects, the cell is a blood cancer cell (e.g., a leukemia cell, lymphoma cell, or multiple myeloma cell). In some aspects, the cell is a carcinoma cell or sarcoma cell. In some aspects, the cell is a brain tumor cell, bladder tumor cell, breast tumor cell, cervical tumor cell, colorectal tumor cell, embryonal tumor cell, gastric tumor cell, germ cell tumor cell, head and neck tumor cell, hematologic tumor cell, kidney tumor cell, melanoma cell, mesothelial tumor cell, ovarian tumor cell, or yolk sac tumor cell. In some embodiments the cell is a breast cancer cell. In some embodiments the cell is a mammalian cell. In some embodiments the cancer for treatment exhibits an increased level of expression or activity of a Myc transcription factor.

In some embodiments the methods disclosed herein further comprise inhibiting expression or activity of SHMT1, SHMT2, and/or MTHFD2. In some embodiments the methods disclosed herein further comprise inhibiting serine synthesis in the cell (e.g., inhibiting one or more genes selected from the group consisting of PHGDH, PSAT1, and PSPH).

In some aspects the methods disclosed herein further comprise treating the subject using radiation therapy. In some aspects the methods disclosed herein further comprise treating the subject with an anti-tumor agent. In some embodiments the anti-tumor agent targets one-carbon metabolism. In some embodiments the anti-tumor agent is methotrexate.

Also described herein are methods of screening one or more test agents to identify a modulator of SFXN1, comprising the steps of: (a) contacting a test agent with SFXN1, (b) measuring the level or activity of the contacted SFXN1, and (c) identifying the test agent as a modulator of SFXN1 if the level or activity of the contacted SFXN1 is decreased or increased as compared to SFXN1 not contacted with the test agent. In some embodiments, the method further comprises a step (d) of contacting the identified modulator with a test cell and measuring proliferation and/or survival of the contacted test cell as compared to a control cell not contacted with the identified modulator. In some embodiments the method further comprises a step (e) of contacting the identified modulator with a cancer cell and measuring proliferation and/or survival of the contacted cancer cell as compared to a non-cancerous cell not contacted with the identified modulator.

In some embodiments the modulator of SFXN1 is an inhibitor of SFXN1. In some embodiments the modulator of SFXN1 is an agent that enhances SFXN1 activity or expression. In some embodiments the test agent is contacted with a cell (e.g., a cancer cell) comprising SFXN1. In some embodiments the test agent is contacted with SFXN1 in a cell free assay. In some embodiments the test agent is contacted with SFXN1 in a liposome. In some aspects the test agent is a small molecule. In some embodiments the activity of SFXN1 to transport serine is measured. In some embodiments the activity of SFXN1 to transport cysteine is measured.

Described herein are methods of screening one or more test agents to identify a candidate anti-cancer agent, comprising contacting the test agent with a cell comprising SFXN1, measuring the survival or proliferation of the contacted cell, and identifying the test agent as a candidate anti-cancer agent if the survival or proliferation of the contacted cell is decreased as compared to the survival or proliferation of a control cell not comprising SFXN1 contacted with the test agent. In some embodiments the cell is a cancer cell (e.g., a blood cancer cell or a breast cancer cell).

Also described herein are methods for modulating mitochondrial transport of cysteine in a cell, the methods comprising modulating expression or activity of one or more sideroflexins, thereby modulating the mitochondrial transport of cysteine in the cell.

In some embodiments the one or more sideroflexins is selected from the group consisting of SFXN1, SFXN2, SFXN3, SFXN4, and SFXN5. In some embodiments, the one or more sideroflexins is SFXN1. In some embodiments, the one or more sideroflexins is SFXN1 and SFXN3. The one or more sideroflexins may be a mammalian sideroflexin (e.g., a human sideroflexin).

In some embodiments, modulating of expression or activity of one or more sideroflexins comprises inhibiting expression or activity of one or more sideroflexins. In some embodiments, modulating expression or activity of one or more sideroflexins comprises contacting the cell with an inhibitor of sideroflexin expression or activity. In some embodiments, an inhibitor of sideroflexin expression or activity comprises a small molecule or nucleic acid. In some aspects, the inhibitor comprises an RNAi agent. In some aspects, the inhibitor comprises D-serine. In some embodiments, modulating expression or activity of one or more sideroflexins comprises deleting or mutating the sideroflexin gene. In some aspects, the sideroflexin gene is deleted or mutated using a CRISPR/Cas genome editing system.

In some embodiments the cell is a cancer cell. In some aspects, the cell is a blood cancer cell (e.g., a leukemia cell, lymphoma cell, or multiple myeloma cell). In some aspects, the cell is a carcinoma cell or sarcoma cell. In some aspects, the cell is a brain tumor cell, bladder tumor cell, breast tumor cell, cervical tumor cell, colorectal tumor cell, embryonal tumor cell, gastric tumor cell, germ cell tumor cell, head and neck tumor cell, hematologic tumor cell, kidney tumor cell, melanoma cell, mesothelial tumor cell, ovarian tumor cell, or yolk sac tumor cell. In some embodiments the cell is a breast cancer cell. In some embodiments the cell is a mammalian cell.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1A provides a schematic of the one-carbon metabolism pathway. dTMP—deoxythymidine monophosphate; THF—tetrahydrofolate; meTHF—methyleneTHF; NAD(P)H—Nicotinamide adenine dinucleotide (phosphate); SHMT—serine hydroxymethyltransferase; MFT—mitochondrial folate transporter/carrier; MTHFD—methylenetetrahydrofolate dehydrogenase. The dashed arrows indicate that the exact nature of the substrate for MFT is unknown. FIG. 1B provides a CRISPR-Cas9 based screening strategy designed to identify new components of the mitochondrial one-carbon pathway. SHMT1-null cells were transduced with a sgRNA library consisting of sgRNAs targeting ~3,000 metabolic enzymes, small molecule transporters, and metabolism-related transcription factors in a Cas9-expressing lentiviral vector and the pool of knockout cells was passaged in media with or without serine. Cells grew slower in the absence of serine compared to in full RPMI media, thus cells were collected after ~14 population doublings in full media or ~9 population doublings in serine-deficient media. The abundance of sgRNAs in the cells cultured in the presence and absence of serine was determined at the beginning and at the end of the culture period. For each gene, its gene score was calculated as the mean $\log_2$ fold-change in the abundance of the 10 sgRNAs targeting the gene. The differential gene score was calculated as the difference in gene scores in absence versus presence of serine. sgRNA—single guide RNA; gDNA—genomic DNA. FIG. 1C shows results of the serine-depletion CRISPR screen in Jurkat and K562 cells. SFXN1 emerges as a strong hit in both the Jurkat and K562 screens. Gene scores in full media were plotted against gene scores in serine-deficient media. Genes with a differential gene score of <−1.5 are shown in red or blue (for serine synthesis genes). SHMT1-null K562 cells are designated as SHMT1$^{-/-/-}$ as K562 cells are triploid. The full list of genes that scored in K562 cells is shown in FIG. 5A. FIG. 1D shows top scoring genes from both screens. Genes were ranked according to differential gene score in full media versus serine-deficient media. 1C—one-carbon; PLP—pyridoxal phosphate. FIG. 1E shows single cell knockout clones confirm the findings from the screen. SFXN1-null cells have a proliferation defect in the absence of serine. The addition of 1 mM formate to the culture media rescues growth. Additional loss of SHMT1 exacerbates the proliferation defect in the Jurkat cells. Mean±SD; n=3, *P<0.001, **P<0.0001; N.S.—not significant. AAVS1 indicates control cells that were treated with an sgRNA targeting the AAVS1 locus as described before Wang et al., "Identification and characterization of essential genes in the human genome," *Science,* 350, 1096-1101 (2015). FIG. 1F shows expression of an sgRNA-resistant cDNA for SFXN1 in the SFXN1-null cells restores their proliferation rate in serine-deficient media (mean±SD; n=3; P<0.01, **P<0.0001). Two-tailed t tests were used for comparisons between groups.

FIG. 2A provides a model of the predicted topology of SFXN1 in the mitochondrial inner membrane. Transmembrane helices are indicated by numbers. IMS—intermembrane space. FIG. 2K shows multiple genes in the cytosolic branch of one-carbon metabolism are synthetic lethal with SFXN1 in Jurkat cells. Genes of the cytosolic one-carbon pathway are selectively required for the optimal proliferation of SFXN1-null cells. Gene scores in wild-type cells were plotted against gene scores in SFXN1-null cells. Genes with a differential gene score of <−1.5 are shown in red. FIG. 2L shows Serine Hydroxymethyltransferase 1 (SHMT1) is the top hit from the SFXN1 synthetic lethality screen. Genes were ranked according to differential gene score in wild-type versus SFXN1-null cells. Cyto 1C metabolism—cytosolic one-carbon metabolism; FA—fatty acid. Two-tailed t tests were used for comparisons between groups. FIG. 2N shows that, like in cells lacking known components of the mitochondrial one-carbon pathway, glycine levels are reduced and the cellular serine/glycine ratio is increased in SFXN1-null cells. Serine and glycine levels were measured by GC-MS in extracts from wild-type Jurkat cells or single-cell-derived control and knockout clones (mean±SD; n=3; P<0.01, *P<0.001). FIG. 2O shows loss of SFXN1 causes a glycine synthesis defect. GC-MS was used to measure glycine in the culture media of wild-type Jurkat cells or single-cell-derived knockout clones incubated for 12 hours with 2,3,3-$^2$H$_3$-serine as the only serine source. The glycine M+0 species is the unlabeled species. The glycine M+1 species is derived from 2,3,3-$^2$H$_3$-serine (mean±SD; n=3; P<0.01, *P<0.001). FIG. 2P shows charged folate species are decreased in SFXN1-null cells. Metabolites were measured by LC-MS in extracts from wild-type Jurkat cells or single-cell-derived control and knockout clones (mean±SD; n=3; P<0.01, *P<0.001, P<0.0001). THF—tetrahydrofolate; 5,10-CH+-THF—5,10-methenylTHF. FIG. 2T shows addition of 1 mM formate reverses the accumulation of purine synthesis intermediates in SFXN1-null cells. Intermediates were measured by LC-MS in extracts from wild-type Jurkat cells or single-cellderived SFXN1-null cells incubated for 24 hours in the indicated media (mean±SD; n=3; **P<0.0001; N.D.—not detected).

FIGS. 3A-3B demonstrate SFXN1 transports serine in vitro. FIG. 3A provides a time course of radioactive serine uptake into proteoliposomes containing SFXN1. LAMP1-containing or empty liposomes were used as controls. Values are averages of two replicates. Cpm—counts per minute. FIG. 3B shows competition of serine uptake after 60 min by different metabolites. FIG. 3C shows competition of serine uptake after 60 min by different metabolites at 500 µM (mean±SD; n=3). FIG. 3D provides steady-state kinetic analysis of SFXN1-mediated serine transport reveals a $V_{max}$ of ~8.2 pmol/min and a $K_m$ of ~170 µM. Velocity, as shown, was calculated as a function of the serine concentration. Each data point was calculated from three replicate data points. FIG. 3E shows radioactive serine uptake into mitochondria purified from SFXN1-null cells is reduced compared to that into mitochondria purified from wild-type cells, while glutamate uptake is unchanged (mean±SD; n=3, **P<0.01; N.S.—not significant). FIG. 3F provides steady-state kinetic analysis of SFXN1-mediated alanine transport reveals a $K_m$ of ~371 µM for alanine. Each data point was calculated from three replicate data points.

FIGS. 4A-4K demonstrate Sideroflexins have conserved functions in one-carbon metabolism. SFXN3 and fly and yeast Sideroflexin homologues can substitute for SFXN1 loss. FIG. 4A provides a phylogenetic tree of human, *Drosophila melanogaster*, and *Saccharomyces cerevisae* Sideroflexins. FIG. 4B shows mRNA levels of the 5 human Sideroflexins in blood cancer and other commonly used cell lines. RPKM (Reads Per Kilobase Million) levels were extracted from the Cancer Cell Line Encyclopedia. FIG. 4C shows Sideroflexin protein levels in blood cancer and other commonly used cell lines. Cell lysates prepared from indicated cell lines were equalized for total protein amounts and analyzed by immunoblotting for the levels of the indicated proteins. FIG. 4D shows Flag-tagged Sideroflexin homologs localize to mitochondria. Wild-type HeLa cells transiently expressing FLAG-Sideroflexin homologs were processed for immunofluorescence detection of the FLAG epitope (cyan) and the mitochondrial inner membrane marker COX4 (magenta). The merged image shows the overlap of both channels in white. FIG. 4E shows CRISPR-Cas9-based screen reveals that SFXN3 is required for growth or proliferation in the absence of SFXN1 and glycine, and thus functionally redundant with SFXN1. SFXN1-null Jurkat cells were infected with a sgRNA library targeting metabolic genes and passaged in the absence of glycine. Gene scores in SFXN1-null cells cultured in the presence of glycine were plotted against gene scores in SFXN1-null cells grown in the absence of glycine. Except for SFXN3, genes with a differential gene score of <−1.5 are shown in red. All Sideroflexins are shown in green. FIG. 4F shows proliferation of different human SFXN-null cells in the absence of serine and glycine. SFXN1/3-null cells are glycine auxotrophs. Formate does not rescue proliferation of SFXN1/3-null cells in the absence of glycine. The asterisk denotes a cell clone lacking SFXN1 and SFXN2 and with incomplete deletion of SFXN3. Proliferation of wild-type Jurkat or single cell-derived knockout cells was assayed in full-, serine- or glycine-deficient media as indicated. In the experiment with formate addition, cells were cultured in media with 1 mM formate for 2 days before initiating the experiment. Mean±SD; n=3, *P<0.001*P<0.0001. FIG. 4G shows accumulation of purine synthesis intermediates is exacerbated in SFXN1/3-null cells compared to their single knockout counterparts. The asterisk denotes a cell clone lacking SFXN1 and SFXN2 and with incomplete deletion of SFXN3. Purine intermediates were measured by LC/MS in extracts from wild-type Jurkat cells, or single-cell-derived knockout cells incubated for 24 hours in RPMI media. Mean±SD; n=3, **P<0.01. FIG. 4H shows human, yeast, and *Drosophila* Sideroflexin homologs with the exception of SFXN4 rescue glycine auxotrophy of cells lacking SFXN1 and SFXN3 (SFXN1/3-null cells). Single-cell-derived SFXN1/3-null Jurkat cells were transduced with empty vector (EV) or cDNAs of human, yeast, and *Drosophila* Sideroflexin homologs. Asterisks denote statistically significant differences in proliferation under glycine-depleted conditions between SFXN1/3-null cells expressing the empty vector and SFXN1/3-null cells re-expressing Sideroflexin homologs. Mean±SD; n=3, *P<0.001*P<0.001. FIG. 4I shows Sideroflexin homologs rescue purine synthesis to different degrees. Purine intermediates were measured by LC/MS in extracts from wild-type Jurkat cells, or single-cell-derived SFXN1/3-null Jurkat cells transduced with empty vector (EV) or cDNAs of human, yeast, and *Drosophila* Sideroflexin homologs cultured in RPMI media for 24 hours. Asterisks denote statistically significant differences between SFXN1/3-null cells expressing empty vector and SFXN1/3-null cells re-expressing Sideroflexin homologs. Mean±SD; n=3, P<0.01, *P<0.001*P<0.001. FIG. 4J shows the accumulation of purine synthesis intermediates is exacerbated in cells lacking both SFXN1 and SFXN3 compared to their single knockout counterparts. The asterisk denotes a cell clone lacking SFXN1 and SFXN2 and with incomplete deletion of SFXN3. Purine intermediates were measured by LC-MS in extracts from indicated cells (mean±SD; n=3; P<0.01). FIG. 4K shows Sideroflexin homologues rescue to varying degrees the purine synthesis defects of cells lacking SFXN1 and SFXN3. Purine intermediates were measured by LC-MS in extracts from wild-type Jurkat cells or the double knockout Jurkat cells expressing an empty vector (EV) or cDNAs of human, yeast, and *Drosophila* Sideroflexin homologues. Asterisks denote statistically significant differences between the cells expressing the empty vector and the Sideroflexin homologues. Values were normalized to the average value of the wild-type samples in (FIG. 4J) because purine synthesis intermediates were not detected in the wild-type samples in this experiment (mean±SD; n=3, **P<0.01; N.D. not detected; N.S.—not significant). Two-tailed t tests were used for comparisons between groups.

FIG. 5A provides a full list of genes with differential gene scores of <−1.5 from K562 cell screen. 1C—one-carbon; PLP—pyridoxal phosphate. FIG. 5B shows individual sgRNA (guide) scores for SFXN1 in Jurkat and K562 cells. FIG. 5C provides immunoblot showing deletion of one-carbon gene products in single cell clones. Lysates prepared from indicated knockout cells were equalized for total protein amount and analyzed by immunoblotting for the levels of the indicated proteins. FIG. 5D shows serine levels in cells decrease when cells are cultured in the absence of serine. Serine levels were measured by LC-MS in extracts from wild-type Jurkat cells (mean±SD; n=3; **P<0.01).

FIGS. 6A-6M demonstrate loss of SFXN1 phenocopies mutants in mitochondrial one-carbon metabolism. FIG. 6A shows serine levels are increased and glycine levels are reduced in SFXN1-null K562 cells and the cellular serine/glycine ratio is increased similarly to cells with deletion of known components of the mitochondrial 1C pathway. Serine and glycine levels were measured by LC/MS in extracts from wild-type K562 cells, or single-cell-derived SFXN1-null cells cultured for 24 hours in RPMI media. FIG. 6B shows THF-to-folate ratio of SFXN1-null Jurkat cells is restored by re-expression of SFXN1. FIG. 6C provides a schematic of purine synthesis pathway indicating steps using one-carbon units in the form of 10-formyl-THF. FIG. 6D shows purine intermediates accumulate in SFXN1-null K562 cells. Purine intermediates were measured by LC/MS in extracts from wild-type K562 cells, or single-cell-derived SFXN1-null cells cultured for 24 hours in RPMI media. FIG. 6E shows serine and glycine levels and serine-to-glycine ratio in Jurkat cells in serine- or glycine-deficient media. FIG. 6F provides tracing strategy to differentiate contribution of cytosolic and mitochondrial pathways to cytosolic TTP synthesis. Oxidation of 2,3,3-$^2$H$_3$-serine by SHMT2 and subsequent enzymes in mitochondria gives rise to a singly labeled formate species, and thus singly labeled (one mass unit heavier, M+1) TTP. Oxidation by SHMT1 in the cytosol gives rise to doubly labeled (two mass unit heavier, M+2) TTP. The difference between unlabeled (M+0), M+1 and M+2 TTP can be resolved on a high-resolution mass spectrometer. The ratio of M+1 to M+2 is indicative of the contribution of mitochondria-versus cytosol-derived one-carbon units to nucleotide synthesis. Adapted from Yu, et al. "Transport of glycine, serine, and proline into spinach leaf mitochondria," *Arch Biochem Biophys*, 227, 180-187 (1983). MeTHF—methylene tetrahydrofolate; TTP—thymidine triphosphate. FIG. 6G shows pool sizes of labeled TTP species in serine-tracing experiment. TTP levels measured by LC/MS were normalized to $^{15}$N-$^{13}$C-glutamate as internal standard. FIG. 6H shows pool sizes of glycine in the culture media supernatant in serine-tracing experiment. Glycine levels measured by GC/MS were normalized to norvaline as internal standard. Mean±SD; n=3, *P<0.05, P<0.01, *P<0.001 ***P<0.001. FIG. 6I shows serine levels are increased and glycine levels are reduced in SFXN1-null K562 cells and the cellular serine/glycine ratio is increased as in cells with deletion of known components of the mitochondrial one-carbon pathway. Serine and glycine levels were measured by LC-MS in extracts from wild-type K562 cells or single-cell-derived control and knockout clones (mean±SD; n=3; *P<0.05, P<0.01, *P<0.001, **P<0.0001). FIG. 6J shows SFXN1 deletion does not result in a reduction of folate or THF. The THF to folate ratio of SFXN1-null Jurkat cells is restored by expression of the sgRNA-resistant SFXN1 cDNA (mean±SD; n=3; P<0.01, ***P<0.001). THF—tetrahydrofolate. FIG. 6K shows purine intermediates accumulate in SFXN1-null K562 cells. Purine intermediates were measured by LC-MS in extracts from wild-type K562 cells or single-cell-derived control and knockout clones (mean±SD; n=3). FIG. 6L shows serine depletion causes accumulation of purine synthesis intermediates. Purine intermediates were measured by LC-MS in extracts from wild-type Jurkat cells, or single-cell-derived SFXN1-null cells incubated for 24 hours in the indicated media (mean±SD; n=3). FIG. 6M provides a one-carbon pathway map indicating genes that scored in the SFXN1 synthetic lethality screen. Two-tailed t tests were used for comparisons between groups.

FIG. 7A shows endogenous SFXN2-4 are present in purified mitochondria from Jurkat cells. Indicated endogenous Sideroflexin proteins are present in purified mitochondria from Jurkat cells. Mitochondria were affinity-purified using the HA-Mito-tag. HA-immunoprecipitates and cell lysates prepared from wild-type cells expressing the HA-mito tag or a control mito-tag and were analyzed by immunoblotting for the levels of the indicated proteins. CS—citrate synthase, mitochondrial matrix marker; VDAC1—voltage-dependent anion channel, mitochondrial outer membrane marker; CALR—calreticulin, ER marker; GOLGA1—Golgin subfamily A member, Golgi marker; LAMP2—lysosome-associated membrane glycoprotein, lysosomal marker; CAT—catalase, peroxisomal marker; RPS6KB1—Ribosomal protein S6 kinase beta-1, cytosolic marker; LMNA—Lamin A, nuclear marker. FIG. 7B shows endogenous SFXN1-4 are present in purified mitochondria from K562 cells. Indicated endogenous Sideroflexin proteins are present in purified mitochondria from K562 cells. Mitochondria were affinity-purified using the HA-Mito-tag. HA-immunoprecipitates and cell lysates prepared from wild-type cells expressing the HA-mito tag or a control mito-tag were analyzed by immunoblotting for the levels of the indicated proteins. FIG. 7C provides immunoblot showing loss of Sideroflexins in Jurkat single cell-derived clones. Lysates prepared from indicated knockout cells were equalized for total protein amount and analyzed by immunoblotting for the levels of the indicated proteins. FIG. 7D provides immunoblot showing levels of SFXN1 and SFXN3 in Jurkat cells expressing the SFXN1 or SFXN3 cDNA. Lysates prepared from indicated knockout cells were equalized for total protein amount and analyzed by immunoblotting for the levels of the indicated proteins. # indicates that the overexpressed SFXN3 protein is recognized by the SFXN1 antibody. FIG. 7E shows expression of SFXN1 or SFXN3 rescues growth and glycine auxotrophy of cells lacking SFXN1 and SFXN3 (SFXN1/3-null cells). Single-cell-derived SFXN1/3-null Jurkat cells were transduced with human SFXN1 or SFXN3 cDNA. Mean±SD; n=3; P<0.01, *P<0.001. FIG. 7F shows reexpression of SFXN1 or SFXN3 rescues purine synthesis intermediates in SFXN1/3-null cells. Purine intermediates were measured by LC/MS in extracts from wild-type Jurkat cells, or single-cell-derived SFXN1/3-null Jurkat cells transduced with human SFXN1 or SFXN3 cDNA cultured in RPMI media for 24 hours. Mean±SD; n=3, *P<0.05, P<0.01, *P<0.001***P<0.001. FIG. 7G provides immunoblot showing Sideroflexin homolog protein levels in wild-type cells and in SFXN1/3-null cells reexpressing different Sideroflexin homologs. Lysates prepared from wild-type or SFXN1/3-null cells transduced with empty vector (EV) or Sideroflexin cDNAs were equalized for total protein amount and analyzed by immunoblotting for the levels of the indicated proteins. # indicates overexpressed SFXN3 recognized by the SFXN1 antibody. ° indicates overexpressed SFXN5 recognized by the SFXN1 antibody. The SFXN1-3 antibody recognizes SFXN1, 2, and 3, and their orthologues. The asterisk denotes constructs containing an N-terminal FLAG-tag. Two-tailed t tests were used for comparisons between groups.

FIG. 8A provides protein levels of the 5 human Sideroflexins in different tissues (data from Human Proteome Map, Kim et al. "A draft map of the human proteome," *Nature*, 509, 575-581 (2014)). FIG. 8B shows mRNA levels of SFXN1 in normal human tissues. TPM (Transcripts Per Kilobase Million) levels were extracted from GTEx Portal V7 (mean±SD). FIG. 8C shows mRNA levels of SFXN1 in human cancers. Leukemias and lymphomas are amongst the cancers with the highest mRNA levels of SFXN1 (indicated in red). RPKM (Reads Per Kilobase Million) levels were extracted from the Cancer Cell Line Encyclopedia ((Barretina et al. "The Cancer Cell Line Encyclopedia enables predictive modelling of anticancer drug sensitivity," *Nature*, 483, 603-607 (2012)); mean±SD).

FIGS. 9A-9C demonstrates SFXN1 transports serine in vitro and may play a role in intracellular (e.g., mitochondrial) cysteine transport. FIG. 9A shows SDS-PAGE and Coomassie blue staining was used to analyze recombinant FLAG-SFXN1 purified from HEK293T cells. FIG. 9B shows steady-state kinetic analysis of SFXN1 transport reveals a Km of 170 µM for serine. Transport over time of [3H] serine (1 µM, indicated by asterisk) in the presence of increasing concentrations of unlabeled serine. FIG. 9C shows SFXN1-null cells have a proliferation advantage compared to wild-type cells in media with low concentrations of cystine. Proliferation of wild-type Jurkat or single cell-derived knockout cells was assayed in full RPMI media (not containing alanine and containing 235 µM cystine) or RPMI containing 130 µM alanine or 10 µM cystine as indicated (mean±SD; n=3; ****P <0.0001).

FIG. 10A shows mtDNA content of wild-type, SFXN1-null and SFXN1 &3 double knockout Jurkat cells (mean±SD; n=3; *P<0.001; N.S.—not significant). FIG. 10B provides mitochondrial mass per cell as determined by flow cytometry analysis of wild-type, SFXN1-null and SFXN1 &3 double knockout Jurkat cells stained with MitoTracker DeepRed FM. The histograms were normalized and smoothened. FIG. 10C shows max intensity z-projections of confocal images of mitochondria visualized by MitoTracker (magenta in merged images) were used to measure mitochondrial length of wild-type, SFXN1-null and SFXN1 &3 double knockout Jurkat cells. Nuclei were stained with Hoechst DNA stain (blue) (mean±SD; n>220; P<0.0001; N.S.—not significant). Scale bar is 5 µm. FIG. 10D provides oxygen consumption rate (OCR) and respiration of wild-type, SFXN1-null and SFXN1 &3 double knockout Jurkat cells determined by Seahorse Extracellular Flux Analysis (mean±SD; n≥5 technical replicates; *P<0.001, **P<0.0001). FIG. 10E shows proliferation of wild-type, SFXN1-null and SFXN1&3 double knockout Jurkat cells was assayed in RPMI containing glucose or galactose as the carbon source as indicated (mean±SD; n=3; *P<0.001, ****P<0.0001). FIG. 10F shows relative mitochondrial membrane potential as assessed by flow cytometry analysis of wild-type, SFXN1-null and SFXN1&3 double knockout Jurkat cells stained with tetramethylrhodamine, methyl ester, and perchlorate (TMRM). Indicated cells were treated with 10 µM FCCP. The histograms were normalized and smoothened. FIG. 10G provides expression of the mitochondrially translated Cytochrome c oxidase (COX; complex IV) subunit 1 (COX1) is reduced in SFXN1&3 double knockout cells. Lysates prepared from indicated cells were equalized for total protein amounts and analyzed by immunoblotting for mitochondrially (COX1) and nuclear encoded mitochondrial proteins (COX4, CS, SHMT2). CS—citrate synthase.

DETAILED DESCRIPTION OF THE INVENTION

Figure 1B:
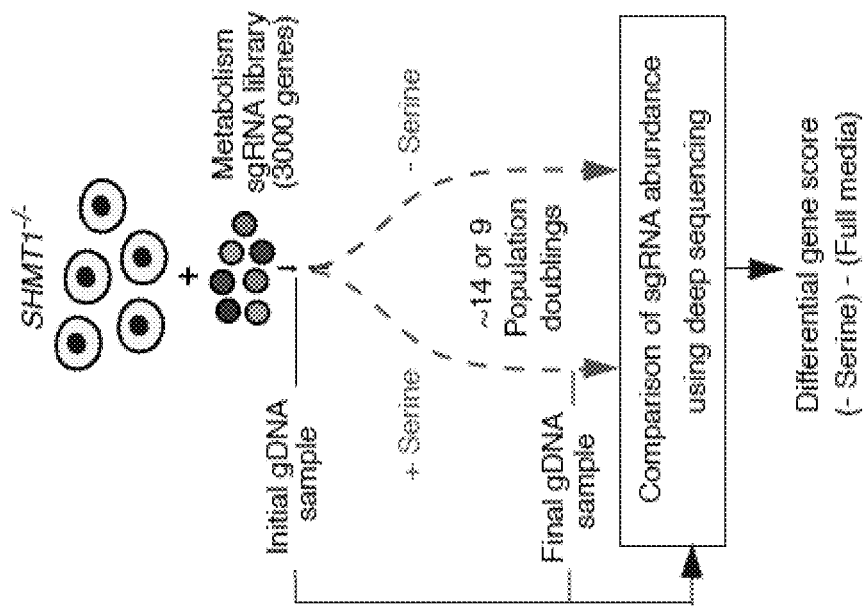
FIGS. 1A-1F demonstrate CRISPR/Cas9 screens identify SFXN1 to be required for growth in the absence of serine.

Descriptions and information relating to certain terms used in the present disclosure are collected here for convenience.

"Agent" is used herein to refer to any substance, compound (e.g., molecule), supramolecular complex, material, or combination or mixture thereof. A compound may be any agent that can be represented by a chemical formula, chemical structure, or sequence. Exemplary agents, include, e.g., small molecules, polypeptides, nucleic acids (e.g., RNAi agents, antisense oligonucleotide, aptamers), lipids, polysaccharides, etc. In general, agents may be obtained using any suitable method known in the art. The ordinary skilled artisan will select an appropriate method based, e.g., on the nature of the agent. An agent may be at least partly purified. In some embodiments an agent may be provided as part of a composition, which may contain, e.g., a counter-ion, aqueous or non-aqueous diluent or carrier, buffer, preservative, or other ingredient, in addition to the agent, in various embodiments. In some embodiments an agent may be provided as a salt, ester, hydrate, or solvate. In some embodiments an agent is cell-permeable, e.g., within the range of typical agents that are taken up by cells and act intracellularly, e.g., within mammalian cells, to produce a biological effect. Certain compounds may exist in particular geometric or stereoisomeric forms. Such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof are encompassed by this disclosure in various embodiments unless otherwise indicated. Certain compounds may exist in a variety or protonation states, may have a variety of configurations, may exist as solvates (e.g., with water (i.e. hydrates) or common solvents) and/or may have different crystalline forms (e.g., polymorphs) or different tautomeric forms. Embodiments exhibiting such alternative protonation states, configurations, solvates, and forms are encompassed by the present disclosure where applicable.

An "assay" may encompass any procedure or process of sequence of procedures or processes that may be used to identify or assess something. As used herein, "assess", "assessing", and similar terms encompass characterizing, detecting, determining, measuring, evaluating, estimating, analyzing, testing, etc. In various embodiments the thing being identified or assessed may be, e.g., a gene, gene product, reactant or product of a reaction, a pathway, an agent, a composition, a cell, a cell line, a tumor, a subject, a reagent for use in a composition or method, etc. In some embodiments an assay may be qualitative or may be at least in part quantitative, e.g., it may provide a measurement, which may be expressed numerically. A measurement may be relative or absolute in various embodiments. In some embodiments an assay provides a measurement of a magnitude, concentration, level, amount, intensity, degree of modulation (e.g., reduction or enhancement), activity, or a change in any of the foregoing, etc. A screen may comprise assessing an entity for one or more properties of interest or for its suitability for one or more purposes or applications of interest or may comprise identifying an entity that has one or more properties of interest or that is or may be suitable for one or more purposes or applications of interest. A screen may comprise, e.g., one or more assays, a computer-aided procedure or process, etc. In various embodiments the thing being or to identified or assessed may be, e.g., a gene, gene product, reactant or product of a reaction, a pathway, an agent, a composition, a cell, a cell line, a tumor, a subject, a reagent for use in a composition or method, etc., or may be a sequence, structure, or other information or representation that may be manipulated, analyzed, processed, or displayed using a computer. In some embodiments a screen comprises assessing multiple entities (e.g., multiple agents, e.g., multiple test agents) in a coordinated manner, e.g., under common direction or control. A screen may comprise performing the same or essentially the same assay multiple times, e.g., using multiple different test agents. The assays may be performed using the same assay system (e.g., using the same equipment/instrumentation). The assays may be performed using essentially the same assay composition, differing in the identity of the test agent. The assays may be performed using a predetermined set of test agents, e.g., a library of agents.

"Cancer" refers to a class of diseases characterized by the development of abnormal cells (cancer cells) that proliferate uncontrollably and have the ability to infiltrate and destroy normal body tissues. The term "tumor" may be used interchangeably with "cancer" or "neoplasm" herein. Cancers include those diseases characterized by formation of malignant solid tumor masses (e.g., carcinomas, sarcomas) and also hematologic cancers such as leukemias in which there may be no detectable solid tumor mass. It will be understood that the term "cancer", "neoplasm", or "tumor" may be used to refer to a particular solid tumor mass or group of cancer cells in a subject as well as to the disease itself. As used herein, the term cancer includes, but is not limited to, the following types of cancer: breast cancer; biliary tract cancer; bladder cancer; brain cancer (e.g., glioblastomas (e.g., astrocytomas), medulloblastomas); cervical cancer; choriocarcinoma; colon cancer; endometrial cancer; esophageal cancer; gastric cancer; hematological cancers; intraepithelial neoplasms including Bowen's disease and Paget's disease; liver cancer (e.g., hepatocellular carcinoma); lung cancer (e.g., bronchogenic carcinoma, small cell lung cancer (SCLC), non-small cell lung cancer (NSCLC), adenocarcinoma of the lung); lymphomas including Hodgkin's disease and non-Hodgkin's lymphomas; neuroblastoma; melanoma; ocular cancer (e.g., intraocular melanoma, retinoblastoma); oral cancer (e.g., oral squamous cell carcinoma); ovarian cancer (e.g., arising from epithelial cells, stromal cells, germ cells, or mesenchymal cells); pancreatic cancer; prostate cancer; rectal cancer; anal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors; throat cancer (e.g., laryngeal cancer, pharyngeal cancer, nasopharyngeal cancer, oropharyngeal cancer), thyroid cancer (e.g., thyroid adenocarcinoma and medullary carcinoma). "Carcinoma" as used herein, refers to a cancer arising or believed to have arisen from epithelial cells, e.g., cells of the cancer possess various molecular, cellular, and/or histological characteristics typical of epithelial cells.

An "effective amount" or "effective dose" of an agent (or composition containing such agent) refers to the amount sufficient to achieve a desired biological and/or pharmacological effect, e.g., when delivered to a cell or organism according to a selected administration form, route, and/or schedule. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or through use of multiple doses, in various embodiments. A biological effect may be, e.g., reducing expression or activity of one or more gene products, reducing activity of a metabolic pathway or reaction, reducing cell proliferation or survival of cells (e.g., tumor cell proliferation or survival), reducing tumor maintenance, size, growth, or progression.

"Genetic modification" refers to any of various processes that comprise (i) introducing a nucleic acid (e.g., a nucleic acid construct) into a cell or organism, wherein the nucleic acid comprises a portion that is stably or transiently expressed or capable of being stably or transiently expressed in the cell (and/or its descendants) or in at least one cell of the organism (and/or in at least one cell of the organism's descendants), in some cases after having been processed in the cell, e.g., reverse transcribed (in the case of introduced RNA), copied, and/or integrated into the genome of a cell, and/or (ii) producing an alteration in the sequence of the genome of a cell or in at least one cell of an organism by a method comprising introducing a targetable nuclease into a cell or organism and, optionally, introducing a nucleic acid (sometimes referred to as a donor) that serves as a template for homology directed repair/homologous recombination. Typically, a genetic modification is heritable. A nucleic acid or vector may be introduced into cells by transfection, infection, or other methods known in the art. Cells may be contacted with an appropriate reagent (e.g., a transfection reagent) to promote uptake of a nucleic acid or vector by the cells. In some embodiments a genetic modification is stable such that it is inherited by descendants of the cell into which a vector or nucleic acid construct was introduced. A stable genetic modification usually comprises alteration of a cell's genomic DNA, such as integration of exogenous nucleic acid into the genome or deletion of genomic DNA. A nucleic acid or vector may comprise a selectable marker that facilitates identification and/or isolation of genetically modified cells and, if desired, establishment of a stable cell line.

As will be appreciated by those of ordinary skill in the art, the term "genetic modification" can also refer to the particular change(s) in the nucleic acid content or genome sequence of the cell that result from the afore-mentioned process(es). An alteration may comprise an insertion of one or more nucleotide(s), a deletion of one or more nucleotide(s), a substitution of one or more nucleotide(s) by different nucleotide(s), or a combination thereof, in or into the genome. The term "genetic modification" as used herein excludes naturally occurring phenomena in which a nucleic acid enters a cell and/or in which the nucleic acid sequence of a genome is altered without intervention of man. Also excluded are selection techniques and physical and chemical mutagenesis techniques that do not involve introducing a nucleic acid or protein (e.g., a nuclease) into a cell or organism.

A "genetically modified cell" refers to an original cell in which a genetic modification has been made as well as descendants of the cell that inherit the genetic alteration(s). Thus a genetically modified cell used in methods or compositions described herein may be a descendant of an original genetically modified cell.

A "genetically modified organism" refers to a multicellular organism, at least some of whose cells (e.g., all or substantially all of the organism's cells) comprise a heritable genetic modification.

"Modulate" as used herein means to decrease (e.g., inhibit, reduce) or increase (e.g., stimulate, activate) a level, response, property, activity, pathway, or process. A "modulator" is an agent capable of modulating a level, response, property, activity, pathway, or process. A modulator may be an inhibitor or activator.

The term "nucleic acid" refers to polynucleotides such as deoxyribonucleic acid (DNA) and ribonucleic acid (RNA). The terms "nucleic acid" and "polynucleotide" are used interchangeably herein and should be understood to include double-stranded polynucleotides, single-stranded (such as sense or antisense) polynucleotides, and partially double-stranded polynucleotides. A nucleic acid often comprises standard nucleotides typically found in naturally occurring DNA or RNA (which can include modifications such as methylated nucleobases), joined by phosphodiester bonds. In some embodiments a nucleic acid may comprise one or more non-standard nucleotides, which may be naturally occurring or non-naturally occurring (i.e., artificial; not found in nature) in various embodiments and/or may contain a modified sugar or modified backbone linkage. Nucleic acid modifications (e.g., base, sugar, and/or backbone modifications), non-standard nucleotides or nucleosides, etc., such as those known in the art as being useful in the context of RNA interference (RNAi), aptamer, CRISPR technology, polypeptide production, reprogramming, or antisense-based molecules for research or therapeutic purposes may be incorporated in various embodiments. Such modifications may, for example, increase stability (e.g., by reducing sensitivity to cleavage by nucleases), decrease clearance in vivo, increase cell uptake, or confer other properties that improve the translation, potency, efficacy, specificity, or otherwise render the nucleic acid more suitable for an intended use. Various non-limiting examples of nucleic acid modifications are described in, e.g., Deleavey G F, et al., Chemical modification of siRNA. Curr. Protoc. Nucleic Acid Chem. 2009; 39:16.3.1-16.3.22; Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008; U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929, 226; 5,977,296; 6,140,482; 6,455,308 and/or in PCT application publications WO 00/56746 and WO 01/14398. Different modifications may be used in the two strands of a double-stranded nucleic acid. A nucleic acid may be modified uniformly or on only a portion thereof and/or may contain multiple different modifications. Where the length of a nucleic acid or nucleic acid region is given in terms of a number of nucleotides (nt) it should be understood that the number refers to the number of nucleotides in a single-stranded nucleic acid or in each strand of a double-stranded nucleic acid unless otherwise indicated. An "oligonucleotide" is a relatively short nucleic acid, typically between about 5 and about 100 nt long.

"Nucleic acid construct" refers to a nucleic acid that is generated by man and is not identical to nucleic acids that occur in nature, i.e., it differs in sequence from naturally occurring nucleic acid molecules and/or comprises a modification that distinguishes it from nucleic acids found in nature. A nucleic acid construct may comprise two or more nucleic acids that are identical to nucleic acids found in nature, or portions thereof, but are not found as part of a single nucleic acid in nature.

The term "polypeptide" refers to a polymer of amino acids linked by peptide bonds. A protein is a molecule comprising one or more polypeptides. A peptide is a relatively short polypeptide, typically between about 2 and 100 amino acids (aa) in length, e.g., between 4 and 60 aa; between 8 and 40 aa; between 10 and 30 aa. The terms "protein", "polypeptide", and "peptide" may be used interchangeably. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins by mammals and are encoded by the genetic code. A "non-standard amino acid" is an amino acid that is not commonly utilized in the synthesis of proteins by mammals. Non-standard amino acids include naturally occurring amino acids (other than the 20 standard amino acids) and non-naturally occurring amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, etc. Modifications may occur anywhere in a polypeptide, e.g., the peptide backbone, the amino acid side-chains and the amino or carboxyl termini. A given polypeptide may contain many types of modifications. Polypeptides may be branched or they may be cyclic, with or without branching. Polypeptides may be conjugated with, encapsulated by, or embedded within a polymer or polymeric matrix, dendrimer, nanoparticle, microparticle, liposome, or the like. Modification may occur prior to or after an amino acid is incorporated into a polypeptide in various embodiments. Polypeptides may, for example, be purified from natural sources, produced in vitro or in vivo in suitable expression systems using recombinant DNA technology (e.g., by recombinant host cells or in transgenic animals or plants), synthesized through chemical means such as conventional solid phase peptide synthesis, and/or methods involving chemical ligation of synthesized peptides (see, e.g., Kent, S., J Pept Sci., 9(9):574-93, 2003 or U.S. Pub. No. 20040115774), or any combination of the foregoing.

The term "RNA interference" (RNAi) encompasses processes in which a molecular complex known as an RNA-induced silencing complex (RISC) reduces gene expression in a sequence-specific manner in, e.g., eukaryotic cells, e.g., vertebrate cells, or in an appropriate in vitro system. RISC may incorporate a short nucleic acid strand (e.g., about 16-about 30 nucleotides (nt) in length) that pairs with and directs or "guides" sequence-specific degradation or translational repression of RNA (e.g., mRNA) to which the strand has complementarity. The short nucleic acid strand may be referred to as a "guide strand" or "antisense strand". An RNA strand to which the guide strand has complementarity may be referred to as a "target RNA". A guide strand may initially become associated with RISC components (in a complex sometimes termed the RISC loading complex) as part of a short double-stranded RNA (dsRNA), e.g., a short interfering RNA (siRNA). The other strand of the short dsRNA may be referred to as a "passenger strand" or "sense strand". The complementarity of the structure formed by hybridization of a target RNA and the guide strand may be such that the strand can (i) guide cleavage of the target RNA in the RNA-induced silencing complex (RISC) and/or (ii) cause translational repression of the target RNA. Reduction of expression due to RNAi may be essentially complete (e.g., the amount of a gene product is reduced to background levels) or may be less than complete in various embodiments. For example, mRNA and/or protein level may be reduced by 50%, 60%, 70%, 75%, 80%, 85%, 90%, 95%, or more, in various embodiments. As known in the art, the complementarity between the guide strand and a target RNA need not be perfect (100%) but need only be sufficient to result in inhibition of gene expression. For example, in some embodiments 1, 2, 3, 4, 5, or more nucleotides of a guide strand may not be matched to a target RNA. "Not matched" or "unmatched" refers to a nucleotide that is mismatched (not complementary to the nucleotide located opposite it in a duplex, i.e., wherein Watson-Crick base pairing does not take place) or forms at least part of a bulge. Examples of mismatches include, without limitation, an A opposite a G or A, a C opposite an A or C, a U opposite a C or U, a G opposite a G. A bulge refers to a sequence of one or more nucleotides in a strand within a generally duplex region that are not located opposite to nucleotide(s) in the other strand. "Partly complementary" refers to less than perfect complementarity. In some embodiments a guide strand has at least about 80%, 85%, or 90%, e.g., least about 91%, 92%, 93%, 94%, 95%, 96%, 97%, 98%, 99%, or 100% sequence complementarity to a target RNA over a continuous stretch of at least about 15 nt, e.g., between 15 nt and 30 nt, between 17 nt and 29 nt, between 18 nt and 25 nt, between 19 nt and 23 nt, of the target RNA. In some embodiments at least the seed region of a guide strand (the nucleotides in positions 2-7 or 2-8 of the guide strand) is perfectly complementary to a target RNA. In some embodiments, a guide strand and a target RNA sequence may form a duplex that contains no more than 1, 2, 3, or 4 mismatched or bulging nucleotides over a continuous stretch of at least 10 nt, e.g., between 10-30 nt. In some embodiments a guide strand and a target RNA sequence may form a duplex that contains no more than 1, 2, 3, 4, 5, or 6 mismatched or bulging nucleotides over a continuous stretch of at least 12 nt, e.g., between 10-30 nt. In some embodiments, a guide strand and a target RNA sequence may form a duplex that contains no more than 1, 2, 3, 4, 5, 6, 7, or 8 mismatched or bulging nts over a continuous stretch of at least 15 nt, e.g., between 10-30 nt. In some embodiments, a guide strand and a target RNA sequence may form a duplex that contains no mismatched or bulging nucleotides over a continuous stretch of at least 10 nt, e.g., between 10-30 nt. In some embodiments, between 10-30 nt is 10, 11, 12, 13, 14, 15, 16, 17, 18, 19, 20, 21, 22, 23, 24, 25, 26, 27, 28, 29, or 30 nt.

As used herein, the term "RNAi agent" encompasses nucleic acids that can be used to achieve RNAi in eukaryotic cells. Short interfering RNA (siRNA), short hairpin RNA (shRNA), and microRNA (miRNA) are examples of RNAi agents. siRNAs typically comprise two separate nucleic acid strands that are hybridized to each other to form a structure that contains a double stranded (duplex) portion at least 15 nt in length, e.g., about 15-about 30 nt long, e.g., between 17-27 nt long, e.g., between 18-25 nt long, e.g., between 19-23 nt long, e.g., 15, 16, 17, 18, 19, 20, 21, 22, 23, 24, 25, 26, 27, 28, 29, or 30 nucleotides. In some embodiments the strands of an siRNA are perfectly complementary to each other within the duplex portion. In some embodiments the duplex portion may contain one or more unmatched nucleotides, e.g., one or more mismatched (non-complementary) nucleotide pairs or bulged nucleotides. In some embodiments either or both strands of an siRNA may contain up to about 1, 2, 3, or 4 unmatched nucleotides within the duplex portion. In some embodiments a strand may have a length of between 15-35 nt, e.g., between 17-29 nt, e.g., 19-25 nt, e.g., 21-23 nt. Strands may be equal in length or may have different lengths in various embodiments. In some embodiments strands may differ by between 1-10 nt in length. A strand may have a 5' phosphate group and/or a 3' hydroxyl (—OH) group. Either or both strands of an siRNA may comprise a 3' overhang of, e.g., about 1-10 nt (e.g., 1-5 nt, e.g., 2 nt). Overhangs may be the same length or different in lengths in various embodiments. In some embodiments an overhang may comprise or consist of deoxyribonucleotides, ribonucleotides, or modified nucleotides or modified ribonucleotides such as 2'-O-methylated nucleotides, or 2'-O-methyl-uridine. An overhang may be perfectly complementary, partly complementary, or not complementary to a target RNA in a hybrid formed by the guide strand and the target RNA in various embodiments.

shRNAs are nucleic acid molecules that comprise a stem-loop structure and a length typically between about 40-150 nt, e.g., about 50-100 nt, e.g., 60-80 nt. A "stem-loop structure" (also referred to as a "hairpin" structure) refers to a nucleic acid having a secondary structure that includes a region of nucleotides which are known or predicted to form a double strand (stem portion; duplex) that is linked on one side by a region of (usually) predominantly single-stranded nucleotides (loop portion). Such structures are well known in the art and the term is used consistently with its meaning in the art. A guide strand sequence may be positioned in either arm of the stem, i.e., 5' with respect to the loop or 3' with respect to the loop in various embodiments. As is known in the art, the stem structure does not require exact base-pairing (perfect complementarity). Thus, the stem may include one or more unmatched residues or the base-pairing may be exact, i.e., it may not include any mismatches or bulges. In some embodiments the stem is between 15-30 nt, e.g., between 17-29 nt, e.g., 19-25 nt. In some embodiments the stem is between 15-19 nt. In some embodiments the stem is between 19-30 nt. The primary sequence and number of nucleotides within the loop may vary. Examples of loop sequences include, e.g., UGGU; ACUCGAGA; UUCAAGAGA. In some embodiments a loop sequence found in a naturally occurring miRNA precursor molecule (e.g., a pre-miRNA) may be used. In some embodiments a loop sequence may be absent (in which case the termini of the duplex portion may be directly linked). In some embodiments a loop sequence may be at least partly self-complementary. In some embodiments the loop is between 1 and 20 nt in length, e.g., 1-15 nt, e.g., 4-9 nt. The shRNA structure may comprise a 5' or 3' overhang. As known in the art, an shRNA may undergo intracellular processing, e.g., by the ribonuclease (RNase) III family enzyme known as Dicer, to remove the loop and generate an siRNA.

Mature endogenous miRNAs are short (typically 18-24 nt, e.g., about 22 nt), single-stranded RNAs that are generated by intracellular processing from larger, endogenously encoded precursor RNA molecules termed miRNA precursors (see, e.g., Bartel, D., Cell. 116(2):281-97 (2004); Bartel D P. Cell. 136(2):215-33 (2009); Winter, J., et al., Nature Cell Biology 11: 228-234 (2009). Artificial miRNA may be designed to take advantage of the endogenous RNAi pathway in order to silence a target RNA of interest. The sequence of such artificial miRNA may be selected so that one or more bulges is present when the artificial miRNA is hybridized to its target sequence, mimicking the structure of naturally occurring miRNA:mRNA hybrids. Those of ordinary skill in the art are aware of how to design artificial miRNA.

An RNAi agent that contains a strand sufficiently complementary to an RNA of interest so as to result in reduced expression of the RNA of interest (e.g., as a result of degradation or repression of translation of the RNA) in a cell or in an in vitro system capable of mediating RNAi and/or that comprises a sequence that is at least 80%, 90%, 95%, or more (e.g., 100%) complementary to a sequence comprising at least 10, 12, 15, 17, or 19 consecutive nucleotides of an RNA of interest may be referred to as being "targeted to" the RNA of interest. An RNAi agent targeted to an RNA transcript may also considered to be targeted to a gene from which the transcript is transcribed.

In some embodiments an RNAi agent is a vector (e.g., an expression vector) suitable for causing intracellular expression of one or more transcripts that give rise to a siRNA, shRNA, or miRNA in the cell. Such a vector may be referred to as an "RNAi vector". An RNAi vector may comprise a template that, when transcribed, yields transcripts that may form a siRNA (e.g., as two separate strands that hybridize to each other), shRNA, or miRNA precursor (e.g., pri-miRNA or pre-mRNA).

An RNAi agent may be produced in any of variety of ways in various embodiments. For example, nucleic acid strands may be chemically synthesized (e.g., using standard nucleic acid synthesis techniques) or may be produced in cells or using an in vitro transcription system. Strands may be allowed to hybridize (anneal) in an appropriate liquid composition (sometimes termed an "annealing buffer"). An RNAi vector may be produced using standard recombinant nucleic acid techniques.

A "sample" may be any biological specimen that contains cells, tissue, or cellular material (e.g., material derived from cells, such as a cell lysate or fraction thereof). A sample may be obtained from (i.e., originates from, was initially removed from) a subject. Methods of obtaining samples are known in the art and include, e.g., tissue biopsy, such as excisional biopsy, incisional biopsy, or core biopsy; fine needle aspiration biopsy; brushings; lavage; or collecting body fluids that may contain cells, such as blood, sputum, lymph, mucus, saliva, or urine. In some embodiments a sample contains at least some intact cells at the time it is removed from a subject. In some embodiments a sample retains at least some of the microarchitecture of a tissue from which it was removed. A sample may be subjected to one or more processing steps after having been obtained from a subject and/or may be split into one or more portions. The term "sample" encompasses processed samples, portions of samples, etc., and such samples are considered to have been obtained from the subject from whom the initial sample was removed. In some embodiments a sample may be obtained from an individual who has been diagnosed with or is suspected of having a tumor, e.g., a brain tumor. A tumor sample is a sample obtained from or comprising tumor cells or a tumor. A tumor sample may have been obtained from a tumor prior to or after removal of the tumor from a subject. A sample, e.g., a sample used in a method or composition disclosed herein, may have been procured directly from a subject, or indirectly, e.g., by receiving the sample from one or more persons who procured the sample directly from the subject, e.g., by performing a biopsy, surgery, or other procedure on the subject.

The term "small molecule" refers to an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

A "subject" may be any vertebrate organism in various embodiments. A subject may be individual to whom an agent is administered, e.g., for experimental, diagnostic, and/or therapeutic purposes or from whom a sample is obtained or on whom a procedure is performed. In some embodiments a subject is a mammal, e.g. a human, non-human primate, rodent (e.g., mouse, rat, rabbit), ungulate (e.g., ovine, bovine, equine, caprine species), canine, or feline. In some embodiments, a subject is an adult. For purposes hereof a human at least 18 years of age is considered an adult.

"Treat", "treating" and similar terms refer to providing medical and/or surgical management of a subject. Treatment may include, but is not limited to, administering an agent or composition (e.g., a pharmaceutical composition) to a subject. Treatment is typically undertaken in an effort to alter the course of a disease (which term is used to indicate any disease, disorder, or undesirable condition warranting therapy) in a manner beneficial to the subject. The effect of treatment may include reversing, alleviating, reducing severity of, delaying the onset of, curing, inhibiting the progression of, and/or reducing the likelihood of occurrence or recurrence of the disease or one or more symptoms or manifestations of the disease. A therapeutic agent may be administered to a subject who has a disease or is at increased risk of developing a disease relative to a member of the general population. In some embodiments a therapeutic agent may be administered to a subject who has had a disease but no longer shows evidence of the disease. The agent may be administered e.g., to reduce the likelihood of recurrence of evident disease. A therapeutic agent may be administered prophylactically, i.e., before development of any symptom or manifestation of a disease. "Prophylactic treatment" refers to providing medical and/or surgical management to a subject who has not developed a disease or does not show evidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease.

A "variant" of a particular polypeptide or polynucleotide has one or more alterations (e.g., additions, substitutions, and/or deletions, which may be referred to collectively as "mutations") with respect to the polypeptide or polynucleotide, which may be referred to as the "original polypeptide" or "original polynucleotide", respectively. An addition may be an insertion or may be at either terminus. A variant may be shorter or longer than the original polypeptide or polynucleotide. The term "variant" encompasses "fragments". A "fragment" is a continuous portion of a polypeptide or polynucleotide that is shorter than the original polypeptide. In some embodiments a variant comprises or consists of a fragment. In some embodiments a fragment or variant is at least 20%, 30%, 40%, 50%, 60%, 70%, 80%, 90%, 95%, 96%, 97%, 98%, 99%, or more as long as the original polypeptide or polynucleotide. A fragment may be an N-terminal, C-terminal, or internal fragment. In some embodiments a variant polypeptide comprises or consists of at least one domain of an original polypeptide. In some embodiments a variant polynucleotide hybridizes to an original polynucleotide under stringent conditions, e.g., high stringency conditions, for sequences of the length of the original polypeptide. In some embodiments a variant polypeptide or polynucleotide comprises or consists of a polypeptide or polynucleotide that is at least 50%, 60%, 70%, 80%, 90%, 95%, 96%, 97%, 98%, 99%, or more identical in sequence to the original polypeptide or polynucleotide over at least 20%, 30%, 40%, 50%, 60%, 70%, 80%, 90%, 95%, 96%, 97%, 98%, 99%, or 100% of the original polypeptide or polynucleotide. In some embodiments a variant polypeptide comprises or consists of a polypeptide that is at least 50%, 60%, 70%, 80%, 90%, 95%, 96%, 97%, 98%, 99%, or more identical in sequence to the original polypeptide over at least 20%, 30%, 40%, 50%, 60%, 70%, 80%, 90%, 95%, 96%, 97%, 98%, 99%, or 100% of the original polypeptide, with the proviso that, for purposes of computing percent identity, a conservative amino acid substitution is considered identical to the amino acid it replaces. In some embodiments a variant polypeptide comprises or consists of a polypeptide that is at least 50%, 60%, 70%, 80%, 90%, 95%, 96%, 97%, 98%, 99%, or more identical to the original polypeptide over at least 20%, 30%, 40%, 50%, 60%, 70%, 80%, 90%, 95%, 96%, 97%, 98%, 99%, or 100% of the original polypeptide, with the proviso that any one or more amino acid substitutions (up to the total number of such substitutions) may be restricted to conservative substitutions. In some embodiments a percent identity is measured over at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments the sequence of a variant polypeptide comprises or consists of a sequence that has N amino acid differences with respect to an original sequence, wherein N is any integer between 1 and 10 or between 1 and 20 or any integer up to 1%, 2%, 5%, or 10% of the number of amino acids in the original polypeptide, where an "amino acid difference" refers to a substitution, insertion, or deletion of an amino acid. In some embodiments a difference is a conservative substitution. Conservative substitutions may be made, e.g., on the basis of similarity in side chain size, polarity, charge, solubility, hydrophobicity, hydrophilicity and/or the amphipathic nature of the residues involved.

In some embodiments a variant is a functional variant, i.e., the variant at least in part retains at least one activity of the original polypeptide or polynucleotide. In some embodiments a variant at least in part retains more than one or substantially all known biologically significant activities of the original polypeptide or polynucleotide. An activity may be, e.g., a catalytic activity, binding activity, ability to perform or participate in a biological function or process, etc. In some embodiments an activity of a variant may be at least 10%, 20%, 30%, 40%, 50%, 60%, 70%, 80%, 90%, 95%, or more, of the activity of the original polypeptide or polynucleotide, up to approximately 100%, approximately 125%, or approximately 150% of the activity of the original polypeptide or polynucleotide, in various embodiments. In some embodiments a variant, e.g., a functional variant, comprises or consists of a polypeptide at least 95%, 96%, 97%, 98%, 99%. 99.5% or 100% identical to an original polypeptide or polynucleotide over at least 70%, 75%, 80%, 85%, 90%, 95%, 96%, 97%, 98%, or 99% or 100% of the original polypeptide or polynucleotide. In some embodiments an alteration, e.g., a substitution or deletion, e.g., in a functional variant, does not alter or delete an amino acid or nucleotide that is known or predicted to be important for an activity, e.g., a known or predicted catalytic residue or residue involved in binding a substrate or cofactor. In some embodiments nucleotide(s), amino acid(s), or region(s) exhibiting lower degrees of conservation across species as compared with other amino acids or regions may be selected for alteration. As will be understood, variants can be created by introducing one or more nucleotide alterations, e.g., one or more substitution(s), addition(s) and/or deletion(s) into a nucleotide sequence encoding a polypeptide, such that one or more amino acid alterations, e.g., substitution(s), addition(s) and/or deletion(s) are introduced into the encoded polypeptide. Alterations can be introduced by standard techniques, such as site-directed mutagenesis, PCR-mediated mutagenesis, etc. Variants may be tested in one or more suitable assays to assess activity.

The term "vector" refers to a nucleic acid, virus, or portion thereof that is capable of mediating entry of, e.g., transferring, transporting, etc., a nucleic acid of interest between different genetic environments or into a cell. The nucleic acid of interest may be linked to, e.g., inserted into, the vector using, e.g., restriction and ligation. Vectors include, for example, DNA or RNA plasmids, cosmids, naturally occurring or modified viral genomes or portions thereof, nucleic acids that can be packaged into viral capsids, mini-chromosomes, artificial chromosomes, etc. Plasmid vectors typically include an origin of replication (e.g., for replication in prokaryotic cells). A plasmid may include part or all of a viral genome (e.g., a viral promoter, enhancer, processing or packaging signals, and/or sequences sufficient to give rise to a nucleic acid that can be integrated into the host cell genome and/or to give rise to infectious virus). Viruses or portions thereof that can be used to introduce nucleic acids into cells may be referred to as viral vectors. Viral vectors include, e.g., adenoviruses, adeno-associated viruses, retroviruses (e.g., lentiviruses), vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-competent or replication-defective. In some embodiments, e.g., where sufficient information for production of infectious virus is lacking, it may be supplied by a host cell or by another vector introduced into the cell, e.g., if production of virus is desired. In some embodiments such information is not supplied, e.g., if production of virus is not desired. A nucleic acid to be transferred may be incorporated into a naturally occurring or modified viral genome or a portion thereof or may be present within a viral capsid as a separate nucleic acid molecule. A vector may contain one or more nucleic acids encoding a marker suitable for identifying and/or selecting cells that have taken up the vector. Markers include, for example, various proteins that increase or decrease either resistance or sensitivity to antibiotics or other agents (e.g., a protein that confers resistance to an antibiotic such as puromycin, hygromycin or blasticidin), enzymes whose activities are detectable by assays known in the art (e.g., β-galactosidase or alkaline phosphatase), and proteins or RNAs that detectably affect the phenotype of cells that express them (e.g., fluorescent proteins). Vectors often include one or more appropriately positioned sites for restriction enzymes, which may be used to facilitate insertion into the vector of a nucleic acid, e.g., a nucleic acid to be expressed. An expression vector is a vector into which a desired nucleic acid has been inserted or may be inserted such that it is operably linked to regulatory elements (also termed "regulatory sequences", "expression control elements", or "expression control sequences") and may be expressed as an RNA transcript (e.g., an mRNA that can be translated into protein or a noncoding RNA such as an shRNA or miRNA precursor). Expression vectors include regulatory sequence(s), e.g., expression control sequences, sufficient to direct transcription of an operably linked nucleic acid under at least some conditions; other elements required or helpful for expression may be supplied by, e.g., the host cell or by an in vitro expression system. Such regulatory sequences typically include a promoter and may include enhancer sequences or upstream activator sequences. In some embodiments a vector may include sequences that encode a 5' untranslated region and/or a 3' untranslated region, which may comprise a cleavage and/or polyadenylation signal, and/or a vector may include a terminator. In general, regulatory elements may be contained in a vector prior to insertion of a nucleic acid whose expression is desired or may be contained in an inserted nucleic acid or may be inserted into a vector following insertion of a nucleic acid whose expression is desired. As used herein, a nucleic acid and regulatory element(s) (e.g., a promoter) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of ordinary skill in the art will be aware that the precise nature of the regulatory sequences useful for gene expression may vary between species or cell types, but may in general include, as appropriate, sequences involved with the initiation of transcription, RNA processing, or initiation of translation. The choice and design of an appropriate vector and regulatory element(s) is within the ability and discretion of one of ordinary skill in the art. For example, one of skill in the art will select an appropriate promoter (or other expression control sequences) for expression in a desired species (e.g., a mammalian species) or cell type. A vector may contain a promoter capable of directing expression in mammalian cells, such as a suitable viral promoter, e.g., from a cytomegalovirus (CMV), retrovirus, simian virus (e.g., SV40), papilloma virus, herpes virus or other virus that infects mammalian cells, or a mammalian promoter from, e.g., a gene such as EF1alpha, ubiquitin (e.g., ubiquitin B or C), globin, actin, phosphoglycerate kinase (PGK), etc., or a composite promoter such as a CAG promoter (combination of the CMV early enhancer element and chicken beta-actin promoter). In some embodiments a human promoter may be used. In some embodiments, a promoter that ordinarily directs transcription by a eukaryotic RNA polymerase I (a "pol I promoter"), e.g., (a promoter for transcription of ribosomal RNA (other than 5S rRNA) or a functional variant thereof) may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase III (a "pol III promoter"), e.g., a promoter for transcription of U6, H1, 7SK or tRNA or a functional variant thereof is used. One of ordinary skill in the art will select an appropriate promoter for directing transcription of a sequence of interest. Examples of expression vectors that may be used in mammalian cells include, e.g., the pcDNA vector series, pSV2 vector series, pCMV vector series, pRSV vector series, pEF1 vector series, Gateway® vectors, etc. Examples of virus vectors that may be used in mammalian cells include, e.g., adenoviruses, adeno-associated viruses, poxviruses such as vaccinia viruses and attenuated poxviruses, retroviruses (e.g., lentiviruses), Semliki Forest virus, Sindbis virus, etc. In some embodiments, regulatable (e.g., inducible or repressible) expression control element(s), e.g., a regulatable promoter, is/are used so that expression can be regulated, e.g., turned on or increased or turned off or decreased. For example, the tetracycline-regulatable gene expression system (Gossen & Bujard, Proc. Natl. Acad. Sci. 89:5547-5551, 1992) or variants thereof (see, e.g., Allen, N, et al. (2000) Mouse Genetics and Transgenics: 259-263; Urlinger, S, et al. (2000). Proc. Natl. Acad. Sci. U.S.A. 97 (14): 7963-8; Zhou, X., et al (2006). Gene Ther. 13 (19): 1382-1390 for examples) can be used. Other inducible/repressible systems that may be used in various embodiments include those that can be regulated by artificial or naturally occurring hormone receptor ligands (e.g., steroid receptor ligands such as naturally occurring or synthetic estrogen receptor or glucocorticoid receptor ligands), metal-regulated systems (e.g., metallothionein promoter), and light-regulated systems. In some embodiments, tissue-specific or cell type specific regulatory element(s) may be used, e.g., in order to direct expression in one or more selected tissues or cell types. A tissue-specific or cell type specific regulatory element generally directs expression at a higher level in one or more tissues or cell types than in many or most other tissues or cell types (e.g., other cell types in the body or in an artificial environment). In some cases a cell type specific regulatory element directs detectable levels of expression only in a particular cell type of interest. However, useful cell type regulatory elements may not be and often are not absolutely specific for a particular cell type. In some embodiments a cell type specific regulatory element may direct expression of an operably linked nucleic acid at a level at least 2-, 5-, 10, 25, 50, or 100-fold greater in a particular cell type than the level at which it would direct expression of the same nucleic acid in a reference population of cells. One of ordinary skill in the art will be aware of tissue and cell type specific regulatory elements and will be able to select an appropriate element to achieve a useful level of expression in one or more selected tissues or cell types in which expression is desired while avoiding substantial levels of expression that might otherwise occur in tissues or cell types in which expression is not desired.

As used herein "level", refers to a measure of the amount of, or a concentration of something, e.g., a biomolecule such as a mRNA or protein or protein complex.

As used herein "expression level" or "level of expression", refers to a measure of the amount of, or a concentration of an expression product, such as a transcription product, for instance an mRNA, or a translation product, for instance a protein or polypeptide.

As used herein "activity" refers to a biological effect or function that is produced or carried out by a product or substance, e.g., an expression product, small molecule, or the like.

As used herein "level of activity" refers to a measure of a biological effect or function of a product or substance, e.g., an expression product, small molecule, or the like. Activity of a molecule or complex typically refers to activity on a per molecule basis or per complex basis. It will be understood that a reduction in expression level typically results in a decrease in total level of activity.

As used herein, a "reduced level" of expression or activity is a level of expression or activity that is detectably lower than a reference level. In some embodiments, a reduced level of expression or activity is between 10% and 95% of a reference level, although lesser and greater reductions are contemplated in some embodiments. In some embodiments expression or activity is reduced by about 75%, about 80%, about 85%, about 90%, about 95%, about 98%, or about 100%. In some embodiments a reduced level of expression or activity is between 0% and 5% of a reference level. In some embodiments a reduced level of expression or activity is between 5% and 15% of a reference level. In some embodiments a reduced level of expression or activity is between 15% and 95%, e.g., between 20% and 80%, between 25% and 75%, between 30% and 70%, or between 40% and 60% of a reference level. In some embodiments a reduced level of expression or activity is between 25% and 50% or between 50% and 75% of a reference level. In some embodiments a reduced level of expression or activity is about 1%, about 5%, about 10%, about 20%, about 25%, about 30%, about 35%, about 40%, about 45%, about 50%, about 55%, about 60%, about 65%, about 70%, about 75%, about 80%, about 85%, about 90%, about 95%, about 97%, about 99% or about 100% of a reference level (but less than the reference level).

As used herein, an "increased level" of expression or activity is a level of expression or activity that is detectably higher than a reference level. In some embodiments, an increased level of expression or activity is between 10% and 100% above a reference level, although lesser and greater increases are contemplated in some embodiments. In some embodiments an increased level of expression or activity is between 15% and 95%, e.g., between 20% and 80%, between 25% and 75%, between 30% and 70%, or between 40% and 60% above a reference level. In some embodiments an increased level of expression or activity is between 25% and 50% or between 50% and 75% above a reference level. In some embodiments an increased level of expression or activity is about 10%, about 20%, about 25%, about 30%, about 35%, about 40%, about 45%, about 50%, about 55%, about 60%, about 65%, about 70%, about 75%, about 80%, about 85%, about 90%, about 95%, about 97%, about 99% or about 100% above a reference level. In some embodiments an increased level of expression or activity is increased over a reference level by a factor of at least 2-fold, at least 3-fold, at least 4-fold, at least 5-fold, at least 6-fold, at least 7-fold, at least 8-fold, at least 9-fold, or at least 10-fold.

An "effective amount" or "effective dose" of a compound or other agent (or composition containing such compound or agent) refers to the amount sufficient to achieve a desired biological and/or pharmacological effect, e.g., when delivered to a cell or organism according to a selected administration form, route, and/or schedule. As will be appreciated by those of ordinary skill in this art, the absolute amount of a particular compound, agent, or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or the desired effect may be achieved by use of multiple doses. An effective amount of a composition may be an amount sufficient to reduce the severity of or prevent one or more symptoms or signs of a disorder.

"Contacting", "contacting a cell" and similar terms as used herein, refer to any means of introducing an agent (e.g., a nucleic acid, peptide, antibody, small molecule, etc.) into a target cell, including chemical and physical means, whether directly or indirectly or whether the agent physically contacts the cell directly or is introduced into an environment in which the cell is present. Contacting is intended to encompass methods of exposing a cell, delivering to a cell, or "loading" a cell with an agent by viral or non-viral vectors, wherein such agent is bioactive upon delivery or wherein such agent is processed intracellularly to an active form. The method of delivery will be chosen for the particular agent and use (e.g., cancer being treated). Parameters that affect delivery, as is known in the medical art, can include, inter alia, the cell type affected, and cellular location. In some embodiments, contacting includes administering the agent to a subject.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, ncbi.nlm.nih.gov/omim/ and in Online Mendelian Inheritance in Animals (OMIA), a database of genes, inherited disorders and traits in animal species (other than human and mouse), at omi-a.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Modulating Mitochondrial Transport of Serine and/or Mitochondrial Transport of Cysteine Disclosed herein are methods for modulating mitochondrial transport of serine within a cell. Also disclosed herein are methods for modulating mitochondrial transport of cysteine. In some embodiments, the methods comprise modulating expression or activity of one or more sideroflexins. The one or more sideroflexins may be selected from the group consisting of SFXN1 (Gene ID: 94081), SFXN2 (Gene ID: 118980), SFXN3 (Gene ID: 81855), SFXN4 (Gene ID: 119559), and SFXN5 (Gene ID: 94282). In some aspects, the one or more sideroflexins is SFXN1. In other aspects, the one or more sideroflexins is SFXN2. In other aspects, the one or more sideroflexins is SFXN3. In some aspects, the one or more sideroflexins is SFXN4. In other aspects, the one or more sideroflexins is SFXN5. In still other aspects, the one or more sideroflexins is SFXN1 and SFXN3. A sideroflexin may be mammal (e.g., human) sideroflexin.

In some embodiments, modulating expression or activity of one or more sideroflexins in a cell comprises inhibiting or decreasing expression or activity of one or more sideroflexins. In other embodiments, modulating expression or activity of one or more sideroflexins in a cell comprises promoting or increasing expression or activity of one or more sideroflexins.

A cell can comprise any of a variety of different genetic modifications that reduce the level of expression or activity of a sideroflexin. In some embodiments, a genetically modified cell comprises a nucleic acid construct comprising a promoter operably linked to a nucleic acid that encodes a polynucleotide or polypeptide that inhibits expression or activity of a sideroflexin. In some embodiments the polynucleotide that causes a cell to have a reduced level of expression of a sideroflexin is an RNAi agent. In some embodiments the RNAi agent is a short hairpin RNA (shRNA), short interfering RNA (siRNA), or microRNA (miRNA).

In some embodiments an RNAi agent causes a reduction in the level of expression of a sideroflexin. The sequence and/or concentration of the RNAi agent used may be chosen such that the RNAi agent inhibits expression of the sideroflexin by a selected amount. One of ordinary skill in the art appreciates that the extent to which an RNAi agent inhibits expression of a target gene may vary depending, e.g., on the sequence of the RNAi agent and the concentration of the RNAi agent. One or more RNAi agents and/or concentrations may be tested to identify an agent that inhibits expression by a selected amount when used at a particular concentration. One of ordinary skill in the art can design suitable RNAi agents.

In some embodiments a polynucleotide that inhibits expression of a sideroflexin is an antisense nucleic acid. Antisense nucleic acids are single-stranded nucleic acids that are capable of hybridizing to a RNA target. Such hybridization may result in, e.g., degradation of mRNA by RNase H or blockage of mRNA translation. The polynucleotide may comprise a sequence at least about 80%, 85%, 90%, 95%, 99%, or 100% complementary to a RNA target over at least 10, 12, 14, 16, 18, 20, 22, 24, 26, 28, or 30 nucleotides (nt). In some embodiments, the sequence may be selected to minimize off-target effects. For example, a sequence that has less than about 70%, 75%, 80%, 85%, 90%, 95%, 99%, or 100% complementarity to known or predicted mRNAs (other than the target) of a species to which the antisense agent is to be administered over at least 10, 12, 14, 16, 18, 20, 22, 24, 26, 28, or 30 nt may be selected. In some embodiments the antisense nucleic acid hybridizes to a coding region, an intron, or a 5' or 3' untranslated region of a mRNA. One of ordinary skill in the art will be able to select a suitable antisense nucleic acid for inhibition of expression of a sideroflexin of interest.

In some embodiments an inhibitory nucleic acid (e.g., a shRNA or miRNA) that reduces expression of a sideroflexin is expressed intracellularly. The level of inhibition produced by the nucleic acid may vary depending on its level of expression. In some embodiments the level of expression of the inhibitory nucleic acid may be determined by the promoter that drives expression of the inhibitory nucleic acid. For example, a promoter that results in a moderate level of expression can be selected. One of ordinary skill in the art will appreciate that a variety of different promoters can be used to express a nucleic acid in a cell and will be able to select an appropriate promoter to result in a selected level of expression of the nucleic acid.

In some embodiments an agent that inhibits expression of a sideroflexin comprises a transcriptional repressor, e.g., an artificial transcriptional repressor that reduces transcription of RNA that encodes the sideroflexin. One of ordinary skill in the art is aware of suitable types of artificial transcriptional repressors capable of inhibiting expression of a gene of interest and methods for designing such agents. In some embodiments an artificial transcriptional repressor comprises a polypeptide comprising a sequence-specific DNA binding domain that binds to a suitable region of the gene of interest, e.g., a promoter, enhancer, or transcription start site of a gene of interest, resulting in transcriptional repression. DNA binding domains that bind to a desired target sequence may be designed based on the DNA binding domains of zinc finger proteins or transcription activator-like effectors (TALEs) using methods known in the art. In some embodiments an artificial transcriptional repressor comprises a polypeptide comprising a catalytically inactive targetable nuclease, e.g., a catalytically inactive Cas protein. Cas proteins (e.g., Cas9) are nucleases that can associate with a guide RNA (gRNA) that localizes the Cas protein to a selected DNA target site by complementary base pairing. Cas proteins are found in a variety of bacterial species including S. pyogenes, S. thermophiles, and N. meningitidis dCas proteins can be rendered catalytically inactive by appropriate amino acid substitution (e.g., D10A and H840A in S. pyogenes Cas9), thereby generating a Cas protein (sometimes referred to as dCas) that has no endonuclease activity but maintains its RNA-guided DNA-binding (associating) capacity. In some embodiments, the polypeptide comprising a DNA binding domain or dCas may further comprise a transcriptional repression domain such as the Krüppel-associated box (KRAB) repressor domain or other repressor domain known in the art. Non-limiting discussion of the design of artificial transcriptional repressors, is found in Kabadi, A M and Gersbach, C M, Methods. 2014; 69(2): 188-197; Gilbert, L A, et al., Cell. 2013; 154(2):442-51. For purposes of description herein, it is sometimes assumed that a targetable nuclease is Cas9, but the disclosure provides embodiments in which any targetable nuclease may be used. For purposes of description herein, it is sometimes assumed that a catalytically inactive targetable nuclease is dCas9, but the disclosure provides embodiments in which any catalytically inactive targetable nuclease may be used. One of ordinary skill in the art is aware of appropriate amino acid alterations (e.g., substitutions) to render a targetable nuclease catalytically inactive.

In some embodiments, a polypeptide comprising a sequence-specific DNA binding domain or catalytically inactive targetable nuclease (e.g., dCas) may further comprise an effector domain that modifies DNA, e.g., by methylation, so as to modulate (e.g., reduce) expression of a gene. For example, a polypeptide comprising (i) a catalytically inactive targetable nuclease (e.g., a catalytically inactive Cas protein (e.g., dCas9)) and (ii) an effector domain having DNA methylation activity (e.g., Dnmt1, Dnmt3a, Dnmt3b, CpG Methyltransferase M.SssI, and/or M.EcoHK31I) may be used to methylate a portion of a promoter region of a gene, e.g., sideroflexin, in order to reduce expression of the gene. One of ordinary skill in the art appreciates that the polypeptide and/or guide RNA or one or more nucleic acids encoding the polypeptide and/or guide RNA may be introduced into a cell or subject to modulate activity and/or expression of one or more genes, e.g., one or more sideroflexins.

In some aspects, genetic modification using targetable nucleases is used to modulate the expression or activity of one or more sideroflexins. The term "targetable nuclease" refers to a nuclease that can be programmed to produce site-specific DNA breaks, e.g., double-stranded breaks (DSBs), at a selected site in DNA or, as appropriate, to localize to a selected site in DNA without causing DNA breaks and, optionally, bring a tethered effector domain into proximity to the site. Such a site may be referred to as a "target site". The target site can be selected by appropriate design of the targetable nuclease or by providing a guide molecule (e.g., a guide RNA, e.g., sgRNA) that directs the nuclease to the target site. Examples of targetable nucleases include zinc finger nucleases (ZFNs), transcription activator-like effector nucleases (TALENs), and RNA-guided nucleases (RGNs) such as the Cas proteins of the CRISPR/Cas Type II system (e.g., Cas9) or the effector proteins of the CRISPR/Cas Type V system (e.g., Cpf1 or C2c1), and engineered meganucleases. CRISPR/Cas systems are particularly convenient. A break created by a targetable nuclease can be repaired by non-homologous end joining, which can result in small deletions or by homology directed repair/homologous recombination in the presence of a suitable repair template to, e.g., create precise alterations in genomic sequence. Methods of using targetable nucleases, e.g., to perform genome modification, are described in numerous publications, such as *Methods in Enzymology*, Doudna J A, Sontheimer E J. (eds), The use of CRISPR systems (e.g., CRISPR/Cas9), ZFNs, and TALENs in generating site-specific genome alterations. Methods Enzymol. 2014, Vol. 546 (Elsevier); Carroll, D., Genome Editing with Targetable Nucleases, Annu. Rev. Biochem. 2014. 83:409-39, and references in either of these. See also U.S. Pat. Pub. Nos. 20140068797, 20140186919, 20140170753, 20160186208, 20160208243, 20160319260 and/or PCT/US2014/034387 (WO/2014/172470). One of ordinary skill in the art can select or design suitable nuclease, guide RNAs, and repair templates to create a genetic modification of interest.

In some embodiments a targetable nuclease is used to modify one or more sideroflexins, wherein the modification reduces or increases the level of expression or activity of the one or more sideroflexins. In some aspects, the modification reduces the level of expression or activity of the one or more sideroflexins. Any of a variety of genetic modifications could have such an effect, such as deletion of all or part of the gene, introduction of a frameshift mutation or stop codon into the coding region, an insertion or substitution of one or more nucleotides that disrupts a regulatory region (e.g., a promoter) or coding region, etc.

In some embodiments a sideroflexin modulator is an aptamer, antibody, or non-antibody polypeptide that binds to a sideroflexin, e.g., SFXN1, SFXN2, SFXN3, SFXN4, or SFXN5, in various embodiments. In some embodiments a sideroflexin modulator (e.g., inhibitor) comprises a single chain antibody or nanobody. In some embodiments a humanized antibody or antibody fragment may be used, e.g., for therapeutic purposes.

In some embodiments one or more non-antibody peptides or polypeptides that bind to targets with affinity and specificity comparable to that of antibodies may be used as modulators of sideroflexin. Peptides that bind to a target of interest (e.g., SFXN1, SFXN2, SFXN3, SFXN4, or SFXN5) may be identified using a variety of different procedures, such as two hybrid assays (e.g., in yeast or mammalian cells) or various display technologies such as phage display, yeast display, ribosome display, bacterial display, or mRNA display technologies, etc. In some embodiments a peptide may be selected from a peptide library, which may be, e.g., a display library or a chemically synthesized library. One or more rounds of selection (e.g., panning) may be performed to identify one or more peptides that, for example, bind to a target with sufficient specificity and affinity to be useful for one or more purposes.

In some embodiments a polypeptide comprises a dominant negative version of a sideroflexin, e.g., a dominant negative version of SFXN1, SFXN2, SFXN3, SFXN4, or SFXN5. In some embodiments a dominant negative version of a protein is a variant that lacks activity or has substantially reduced functional activity relative to normal and antagonizes or interferes with function of the normal version of the protein expressed by a cell. In some embodiments a dominant negative variant is a fragment of a normal protein or has an alteration in one or more amino acids (e.g., a catalytic residue) that reduces or eliminates functional activity. In some embodiments a dominant negative variant lacks at least some amino acid(s) or domain(s) required for normal activity but retains ability to physically interact with (e.g., bind to) a substrate, cofactor, regulator, or binding partner of the normal protein. A dominant negative variant may, for example, compete with a normal version of a protein for interaction with a substrate, cofactor, regulator, or binding partner. A dominant negative variant may be capable of binding a substrate but have reduced ability to catalyze a reaction involving the substrate, as compared with the normal version of the protein. In the case of proteins that normally act as part of a complex (e.g., a dimer) a dominant negative variant may be capable of forming a complex with a normal version of the protein, but the resulting complex lacks activity or has reduced activity relative to a complex formed that comprises the normal protein and not the dominant negative variant.

In some embodiments a sideroflexin modulator is an amino acid. The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified Amino acid analogs are compounds that have the same basic chemical structure as a naturally occurring amino acid, i.e., a carbon bound to hydrogen, a carboxyl group, an amino group, and an R group. Such analogs have modified R or modified peptide backbones, but retain the same basic chemical structure as a naturally occurring amino acid Amino acid mimetics refers to chemical compounds that have a structure that is different from the general chemical structure of an amino acid, but that function in a manner similar to a naturally occurring amino acid. In some aspects a modulator of sideroflexin activity or expression may be serine, glycine, alanine, cysteine, or analogs thereof. In certain aspects a modulator of sideroflexin activity or expression is D-serine or L-serine.

In some embodiments an agent that inhibits expression of a sideroflexin acts post-transcriptionally, e.g., by causing mRNA degradation and/or repressing mRNA translation. One of ordinary skill in the art is aware of suitable types of agents capable of post-transcriptionally inhibiting expression of a gene of interest and methods for designing such agents. For example, shRNA, siRNA, and artificial miRNA can be used as described herein. In some embodiments an agent that inhibits expression of a gene post-transcriptionally comprises a polypeptide comprising a sequence-specific RNA binding domain that binds to a sequence in an mRNA (e.g., in the 5' untranslated region, coding sequence, or 3' UTR) wherein the polypeptide promotes mRNA degradation or represses mRNA translation. In some embodiments the polypeptide binds to the 5' UTR and represses translation, e.g., by preventing ribosome binding. In some embodiments the polypeptide may comprise a domain that recruits a deadenylase that removes at least part of the mRNA's polyA tail, thereby destabilizing the mRNA. In some embodiments the polypeptide comprises tristetraprolin (TTP), also known as zinc finger protein 36 homolog (ZFP36). In some embodiments an RNA binding domain capable of binding to an RNA sequence is designed based on pentatricopeptide repeat or Pumilio/fem-3 mRNA binding factor (PUF) proteins, which can be rationally modified for predictable RNA recognition. Non-limiting discussion of various types of polypeptides that can be used as post-transcriptional repressors is found in Abil, Z., et al. Journal of Biological Engineering, 2014, 8:7; Cao, J., et al., Nucl. Acids Res. (30 Apr. 2015) 43 (8): 4353-4362, and references therein.

A transcriptional repressor or post-transcriptional repressor may be expressed intracellularly, e.g., by introducing a nucleic acid that encodes it into the cell. In embodiments in which an artificial transcriptional repressor comprising a dCas protein, an appropriate gRNA may also be expressed in or otherwise introduced into the cells. In some embodiments the cell is genetically modified to stably express the transcriptional repressor or post-transcriptional repressor. In some embodiments in which dCas is used, the cell is genetically modified to stably express one or more gRNA. In some embodiments the cell transiently expresses the transcriptional repressor or post-transcriptional repressor. In some embodiments in which dCas is used, the cell transiently expresses stably one or more gRNA. The amount by which a transcriptional or post-transcriptional repressor reduces expression of a target gene may vary depending on the level of expression of the transcriptional or post-transcriptional repressor, which can be selected to produce a desired reduction in expression of a gene of interest.

In some embodiments expression of one or more sideroflexins is regulated by a Myc transcription factor. In some aspects SFXN1, SFXN2, and/or SFXN3 expression is regulated by a Myc transcription factor. In some aspects one or more Myc binding sites are located within the promoter region of a sideroflexin. In some aspects at least 10, at least 15, at least 20, at least 25, at least 30, or at least 35 Myc binding sites are located within the promoter region of a sideroflexin (e.g., SFXN1, SFXN2, SFXN3). In some embodiments expression of one or more sideroflexins may be modulated by modulating the expression or activity of Myc. For example, in some embodiments, inhibiting expression of one or more SFNXs comprises inhibiting expression or activity of Myc. In some embodiments expression of one or more sideroflexins may be modulated by deleting or modifying one or more Myc binding sites in a sideroflexin promoter.

In some embodiments the level of expression or activity of a sideroflexin is reduced by an amount relative to a reference level. In other embodiments the level of expression or activity of a sideroflexin is increased by an amount relative to a reference level. As used herein "reference level" refers to a control level. A control level may be the level that was present before a manipulation or procedure that resulted in change in expression or activity, e.g., a level present in the absence of a test agent or therapeutic agent. In some embodiments a reference level is a level present in normal, healthy cells that have not been genetically modified or exposed to a test agent.

In some embodiments modulating the level of expression or activity of sideroflexin, thereby modulates mitochondrial transport of serine in a cell. In some embodiments modulating the level of expression or activity of sideroflexin, thereby modulates mitochondrial transport of cysteine in a cell. In some aspects the cell is a cancer cell. In certain embodiments the cell is a blood cancer cell. The cell may be a leukemia cell, a lymphoma cell, or a multiple myeloma cell. In some aspects, the cell may be a carcinoma cell or a sarcoma cell. In some embodiments the cell is a brain tumor cell, a bladder tumor cell, a breast tumor cell, a cervical tumor cell, a colorectal tumor cell, an embryonal tumor cell, a gastric tumor cell, a germ cell tumor cell, a head and neck tumor cell, a hematologic tumor cell, a kidney tumor cell, a melanoma cell, a mesothelial tumor cell, an ovarian tumor cell, or a yolk sac tumor cell. In certain embodiments the cell is a breast cancer cell. In other embodiments the cell is a leukemia cell. In some embodiments the cell exhibits increased expression or activity of a Myc transcription factor.

In some embodiments a method that comprises modulating mitochondrial transport of serine in a cell further comprises modulating (e.g., inhibiting) expression or activity of SHMT1 and/or SHMT2. In some embodiments a method that comprises modulating mitochondrial transport of serine in a cell further comprises modulating (e.g., inhibiting) expression or activity of MTHFD2. Methods that comprise modulating mitochondrial transport of serine in a cell may further comprise inhibiting expression or activity of SHMT1 and/or SHMT2 and inhibiting expression or activity of MTHFD2. In some embodiments the inhibition of mitochondrial transport of serine in the cell thereby inhibits one-carbon metabolism in the cell. In some embodiments a method that comprises modulating mitochondrial transport of serine in a cell further comprises modulating mitochondrial transport of cysteine in a cell. In some embodiments the inhibition of mitochondrial transport of cysteine in the cell thereby modulating redox status/antioxidant defense in the cell.

Methods of Screening for Modulators of Sideroflexin

Methods of screening one or more test agents to identify a modulator of one or more sideroflexins (e.g., SFXN1, SFXN2, SFXN3, SFXN4, and/or SFXN5) are described herein. The methods comprise identifying an agent that modulates the expression or activity of a sideroflexin (e.g., SFXN1). In some embodiments identifying an agent that modulates the expression or activity of a sideroflexin comprises contacting a test agent with a sideroflexin, measuring the effect of the test agent on the level of expression or activity of the sideroflexin, and identifying the agent as a modulator of expression or activity of the sideroflexin if the level of expression or activity of the sideroflexin differs from what would be expected in the absence of the test agent.

In some aspects the method comprises identifying an agent that reduces the level of expression or activity of sideroflexin (e.g., is an inhibitor of sideroflexin). In other aspects the method comprises identifying an agent that enhances or increases the level of expression or activity of sideroflexin (e.g., is an activator or enhancer of sideroflexin).

In some embodiments the methods of screening test agents described herein further comprise contacting the identified modulator with a test cell and measuring proliferation and/or survival of the contacted test cell as compared to a control cell not contacted with the identified modulator. In some embodiments the test cell and control cell are non-cancerous cells. In some embodiments the test cell and control cell are cancer cells. In some embodiments the methods may further comprise contacting the identified modulator, e.g., inhibitor, with a cancer cell and measuring proliferation and/or survival of the contacted cancer cell as compared to a non-cancerous cell not contacted with the identified modulator. In some embodiments a method comprises identifying an agent that selectively inhibits proliferation and/or survival of cancer cells as compared to non-cancerous cells.

In some aspects the test agent is contacted with a cell (e.g., a cancer cell) comprising a sideroflexin in the first step of the described method. The test agent may be contacted with a sideroflexin in a cell free assay. In other aspects the test agent may be contacted with a sideroflexin in a liposome. In some aspects the test agent is a small molecule or nucleic acid. In other aspects the test agent is an amino acid (e.g., D-serine or L-serine or an analog of L-serine or D-serine). In some embodiments the test agent is a one-carbon amino acid.

In some embodiments an identified modulator of sideroflexin, e.g., a sideroflexin inhibitor, acts as an anti-cancer agent.

In some embodiments a method of screening one or more test agents to identify a candidate anti-cancer agent comprise contacting a test agent with a cell (e.g., a cancer cell) comprising a sideroflexin (e.g., SFXN1), measuring the survival or proliferation of the contacted cell, and identifying the test agent as a candidate anti-cancer agent if the survival or proliferation of the contacted cell is decreased as compared to the survival or proliferation of a control cell not comprising sideroflexin contacted with the test agent. In some embodiments the test agent may be transported into mitochondria by a sideroflexin (e.g., SFXN1) wherein it exerts toxic activity within the mitochondria.

In some embodiments a method of screening one or more test agents to identify a modulator of a sideroflexin (e.g., SFXN1) comprises a high-throughput transport assay (e.g., in vitro transport assay). In some aspects an artificial membrane (e.g., a liposome) may be utilized. In other aspects a bacterial system may be utilized (e.g., Gram-negative bacteria such as *E. coli* or Gram-positive bacteria such as *B. subtilis* or *Lactococcus lactis*). In some embodiments a sideroflexin may be reconstituted into a liposome and one or more test agents are applied to the sideroflexin. In some embodiments bacterial *Lactococcus lactis* cells are grown to express a sideroflexin and the cells are contacted with one or more test agents. In some aspects the serine transport activity of the sideroflexin (e.g., uptake of serine into the liposome or the cell by the sideroflexin) is measured. In some aspects the cysteine transport activity of the sideroflexin (e.g., transport of the cysteine into the liposome or the cell by the sideroflexin) is measured.

In some embodiments serine uptake is coupled to an enzymatic reaction that produces a detectable product, e.g., a fluorescent product, for detection. In some embodiments D-serine oxidase is used as an enzyme. D-serine oxidase may produce $H_2O_2$ when acting on serine, which can be detected in various ways known to those of skill in the art, such as using fluorescence probes as described in Lampard E V, et al. ChemistryOpen. 2018 Jan. 26; 7(3):262-265. doi: 10.1002/open.201700189. eCollection (2018) Boronate-Based Fluorescence Probes for the Detection of Hydrogen Peroxide, incorporated herein by reference. In some embodiments a fluorescent serine detector molecule may be used, such as those described by Liu et al., Organic Letters. 2010; 12(18): 4172-4175, Highly Enantioselective Fluorescent Recognition of Serine and Other Amino Acid Derivatives, incorporated herein in its entirety. For example, a fluorescent serine detector molecule may be enclosed within a system (e.g., liposome or bacterial system) with a sideroflexin. A test agent may be added to the system, but is separated from the detector molecule (e.g., by the liposome membrane). Serine may be added to the system at the same time as the test agent or after the test agent is added. In some aspects, transport of the serine by the sideroflexin may be measured. If the test agent blocks serine transport (e.g., inhibits sideroflexin activity) the system (e.g., liposome) fails to become fluorescent.

In some embodiments serine transport activity of the sideroflexin (e.g., uptake of serine into the liposome or the cell by the sideroflexin) is measured using an assay of D-amino oxidase (DAAO) activity, such as those described by Rosini, et al., Frontiers in Molecular Biosciences. 2018; 4(102): 1-15, Assays of D-Amino Acid Oxidase Activity, incorporated herein by reference. In some embodiments a system (e.g., a liposome) comprises an enzyme and one or more reagents necessary for the enzyme to catalyze the dehydrogenation of D-serine separated from other aspects of the system by a barrier (e.g., by a liposome membrane or a lipid layer). In some aspects a sideroflexin (e.g., SFXN1) is incorporated in the barrier (e.g., a liposome membrane or lipid layer). In some aspects a test agent is added to the system. D-serine may be added to the system after addition of the test agent or at the same time as adding the test agent. If the test agent blocks transport of D-serine (e.g., is an inhibitor of a sideroflexin), the assay will fail to detect a signal or the signal will be reduced as compared to a signal from a system not contacted with a test agent. If the test agent fails to block transport of D-serine, the assay will detect a signal greater than a signal from a system not contacted with a test agent. In some embodiments the assay used to detect DAAO activity is a colorimetric assay or a fluorometric assay. In some embodiments a test agent identified as an inhibitor of D-serine transport is further assessed with respect to L-serine transport. In some aspects a secondary assay is performed to confirm the test agent identified as an inhibitor of D-serine transport also inhibits L-serine transport.

In some embodiments a cell system is created for screening one or more test agents to identify a modulator of a sideroflexin (e.g., SFXN1). In some aspects cell lines are created that express a single selected sideroflexin selected from the group consisting of SFXN1, SFXN2, SFXN3, and SFXN5, and may in some embodiments further express SFXN4. The cell lines may be generated by knocking out or inhibiting expression of the non-selected sideroflexins, and optionally, overexpressing the selected sideroflexin. Such modifications may be made utilizing any known methods available to those of skill in the art, including those described herein. In some embodiments the generated cell lines are cultured in glycine-deficient media and cell growth and proliferation are measured. In some embodiments glycine-deficient media is formulated without the addition of glycine. In some embodiments glycine-deficient media lacks detectable levels of glycine. In some embodiments a medium that has less than about 0.0001 g/L glycine may be used. In some aspects the cultured cells are contacted with one or more test agents and cell growth and proliferation is measured and compared to uncontacted cultured cells. In some aspects the effect of the agent on cell viability or proliferation may be measured using any suitable method known in the art or using an assay described herein. The one or more test agents are identified as inhibitors of the selected sideroflexin if cell growth and/or cell proliferation of the contacted cultured cells is inhibited. In some embodiments the generated cell lines are cultured in glycine-containing media and contacted with an identified inhibitor of the sideroflexin, thereby confirming the identified inhibitor is acting against the sideroflexin. In some embodiments a cell in which SFXN1 is expressed and SFXN2, SFXN3, and SFXN5 are knocked out may be used to identify an agent that inhibits expression or activity of SFXN1. In some embodiments SFXN4 is also knocked out. In some embodiments SFXN4 is not knocked out. In some embodiments a cell in which SFXN3 is expressed and SFXN1, SFXN2, and SFXN5 are knocked out may be used to identify an agent that inhibits expression or activity of SFXN3. In some embodiments SFXN4 is also knocked out. In some embodiments SFXN4 is not knocked out.

In certain embodiments of any method described herein, the survival or proliferation of cells, e.g., test cells and/or control cells, is determined by an assay selected from: a cell counting assay, a replication labeling assay, a cell membrane integrity assay, a cellular ATP-based viability assay, a mitochondrial reductase activity assay, a caspase activity assay, an Annexin V staining assay, a DNA content assay, a DNA degradation assay, and a nuclear fragmentation assay. Exemplary assays include BrdU, EdU, or H3-Thymidine incorporation assays; DNA content assays using a nucleic acid dye, such as Hoechst Dye, DAPI, actinomycin D, 7-aminoactinomycin D or propidium iodide; cellular metabolism assays such as AlamarBlue, MTT, XTT, and CellTitre Glo; nuclear fragmentation assays; cytoplasmic histone associated DNA fragmentation assay; PARP cleavage assay; TUNEL staining; and Annexin staining. In some embodiments, gene expression analysis (e.g., microarray, cDNA array, quantitative RT-PCR, RNAse protection assay, RNA-Seq) may be used to measure the expression of genes whose products mediate or are correlated with cell cycle, cell survival (or cell death, e.g., apoptosis), and/or cell proliferation, as an indication of the effect of an agent on cell viability or proliferation. Alternately or additionally, expression of proteins encoded by such genes may be measured. In other embodiments, the activity of a gene, such as those disclosed herein, can be assayed in a compound screen. In some embodiments, cells are modified to comprise an expression vector that includes a regulatory region of a gene whose products mediate or are correlated with cell cycle, cell survival (or cell death), and/or cell proliferation operably linked to a sequence that encodes a reporter gene product (e.g., a luciferase enzyme), wherein expression of the reporter gene is correlated with transcriptional activity of the gene. In such embodiments assessment of reporter gene expression (e.g., luciferase activity) provides an indirect method for assessing cell survival or proliferation. Those of ordinary skill in the art are aware of genes whose products mediate or are correlated with cell cycle, cell survival (or cell death), and/or cell proliferation.

In some embodiments the activity of an agent (e.g., a test agent) can be tested by contacting test cells and control cells that are in a co-culture. Co-cultures enable selective evaluation of the properties (e.g., survival or proliferation) of two or more populations of cells (e.g., test and control cells) in contact with an agent in a common growth chamber. Typically, each population of cells grown a co-culture will have an identifying characteristic that is detectable and distinct from an identifying characteristic of the other population(s) of cells in the co-culture. In some embodiments, the identifying characteristic comprises a level of expression of a fluorescent protein or other reporter protein or a protein expressed at the cell surface that could be detected using an antibody. Numerous fluorescent proteins are known in the art and may be used. Such proteins include, e.g., green, blue, yellow, red, orange, and cyan fluorescent proteins (FP). In some embodiments, test cells and control cells express different, distinguishable FPs, e.g., a red FP and a green FP, or other pairs of FPs that have different emission spectra. Other reporter proteins include, e.g., enzymes such as luciferase, beta-galactosidase, alkaline phosphatase, etc. However, other identifying characteristics known in the art may be suitable, provided that the identifying characteristic enables measurement (e.g., by FACS or other suitable assay method) of the level of survival or proliferation of each of the two or more populations of cells in the co-culture. A cell can be modified to have an identifying characteristic using methods known in the art, e.g., by introducing into the cell a nucleic acid construct encoding an FP (or other detectable protein) operably linked to a promoter. In some embodiments, a nucleic acid construct that encodes an RNAi agent that reduces expression of a sideroflexin and a nucleic acid construct that encodes a FP or other detectable protein are incorporated into the same vector. In some embodiments, they may be in different vectors. In some embodiments, the construct(s) may be integrated into the genome of the cell.

Compositions, e.g., co-cultures, comprising at least some test cells (e.g., between 1% and 99% test cells) and at least some control cells (e.g., between 1% and 99% control cells), are disclosed herein. In some embodiments the percentage of test cells is between 10% and 90%. In other embodiments the percentage of test cells is between 20% and 80%. In some embodiments the percentage of test cells is between 30% and 70%. In some embodiments the percentage of test cells is between 40% and 60%, e.g., about 50%. In some embodiments the composition further comprises a test agent.

In some embodiments, test cells and control cells are maintained in separate vessels (e.g., separate wells of a microwell plate) under substantially identical conditions.

Assay systems comprising test cells, control cells, and one or more test compounds, e.g., 10, 100, 1000, 10,000, or more test agents, wherein the cells and test agents are arranged in one or more vessels in a manner suitable for assessing effect of the test compound(s) on the cells, are aspects of the invention. Typically the vessels contain a suitable tissue culture medium, and the test compounds are present in the tissue culture medium. One of skill in the art can select a medium and culture environment appropriate for culturing a particular cell type.

In various embodiments the number of test agents is at least 10; 100; 1000; 10,000; 100,000; 250,000; 500,000 or more. In some embodiments test agents are tested in individual vessels, e.g., individual wells of a multiwell plate (sometimes referred to as microwell or microtiter plate or dish). In some embodiments a multiwell plate of use in performing an assay or culturing or testing cells or agents has 6, 12, 24, 96, 384, or 1536 wells. Cells (test cells and/or control cells) can be contacted with one or more test agents for varying periods of time and/or at different concentrations. In certain embodiments cells are contacted with test agent(s) for between 1 hour and 20 days, e.g., for between 12 and 48 hours, between 48 hours and 5 days, e.g., about 3 days, between 2 and 5 days, between 5 days and 10 days, between 10 days and 20 days, or any intervening range or particular value. Cells can be contacted with a test agent during all or part of a culture period. Cells can be contacted transiently or continuously. Test agents can be added to culture media at the time of replenishing the media and/or between media changes. If desired, test agent can be removed prior to assessing growth and/or survival. In some embodiments a test agent is tested at 1, 2, 3, 5, 8, 10 or more concentrations. Concentrations of test agent may range, for example, between about 1 nM and about 100 μM. For example, concentrations 1 nM, 10 nM, 50 nM, 100 nM, 500 nM, 1 μM, 5 μM, 10 μM, 50 μM, 100 μM (or any subset of the foregoing) may be used.

In some embodiments of any aspect or embodiment in the present disclosure relating to cells, a population of cells, cell sample, or similar terms, the number of cells is between 10 and $10^{13}$ cells. In some embodiments the number of cells may be at least about $10^3$, $10^4$, $10^5$, $10^6$, $10^7$, $10^8$, $10^9$, $10^{10}$, $10^{11}$, $10^{12}$ cells, or more. In some embodiments, the number of cells is between $10^5$ and $10^{12}$ cells, e.g., at least $10^6$, $10^7$, $10^8$, $10^9$, $10^{10}$, $10^{11}$, up to about $10^{12}$ or about $10^{13}$. In some embodiments a screen is performed using multiple populations of cells and/or is repeated multiple times. In some embodiments, the number of cells is between $10^5$ and $10^{12}$ cells, e.g., at least $10^6$, $10^7$, $10^8$, $10^9$, $10^{10}$, $10^{11}$, up to about $10^{12}$. In some embodiments smaller numbers of cells are of use, e.g., between $1-10^4$ cells. In some embodiments a population of cells is contained in an individual vessel, e.g., a culture vessel such as a culture plate, flask, or well. In some embodiments a population of cells is contained in multiple vessels. In some embodiments two or more cell populations are pooled to form a larger population.

In some embodiments, each of one or more test cells is contacted with a different concentration of, and/or for a different duration with, a test agent than at least one other test cell; and/or each of the one or more control cells is contacted with a different concentration of, and/or for a different duration with, the test agent than at least one other control cell.

In some embodiments, a method may comprise generating a dose response curve for an agent, test cells, and/or control cells, wherein the dose response curve for test cells indicates the level of inhibition of survival or proliferation of the one or more test cells by the agent at a plurality of doses and wherein the dose response curve for control cells indicates the level of inhibition of survival or proliferation of the one or more control cells by the agent at a plurality of doses. In some embodiments, a method may comprise generating a dose response curve that indicates the relative level of inhibition of survival or proliferation of test cells versus control cells at a plurality of doses.

In some embodiments, a method may further comprise determining (e.g., by analyzing a dose response curve) an IC50, EC50, or both, for an agent. In some embodiments an agent is identified for which the IC50 value, the EC50 value, or both, for the agent on the one or more test cells is statistically significantly less than the IC50 value for the agent on the one or more control cells. In some embodiments, an agent is identified for which the IC50 value, the EC50 value, or both, for the agent on the one or more test cells is statistically significantly less than the EC50 value for the agent on the one or more control cells.

In some embodiments, a high throughput screen (HTS) is performed. A high throughput screen can utilize cell-free or cell-based assays. High throughput screens often involve testing large numbers of compounds with high efficiency, e.g., in parallel. For example, tens or hundreds of thousands of compounds can be routinely screened in short periods of time, e.g., hours to days. Often such screening is performed in multiwell plates containing, at least 96 wells or other vessels in which multiple physically separated cavities or depressions are present in a substrate. High throughput screens often involve use of automation, e.g., for liquid handling, imaging, data acquisition and processing, etc. Certain general principles and techniques that may be applied in embodiments of a HTS of the present invention are described in Macarrón R & Hertzberg R P. Design and implementation of high-throughput screening assays. Methods Mol Biol., 565:1-32, 2009 and/or An WF & Tolliday N J., Introduction: cell-based assays for high-throughput screening. Methods Mol Biol. 486:1-12, 2009, and/or references in either of these. Useful methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser.

The term "hit" generally refers to an agent that achieves an effect of interest in a screen or assay, e.g., an agent that has at least a predetermined level of modulating effect on cell survival, cell proliferation, gene expression, protein activity, or other parameter of interest being measured in the screen or assay. Test agents that are identified as hits in a screen may be selected for further testing, development, or modification. In some embodiments a test agent is retested using the same assay or different assays. For example, a candidate anticancer agent may be tested against multiple different cancer cell lines or in an in vivo tumor model to determine its effect on cancer cell survival or proliferation, tumor growth, etc. Additional amounts of the test agent may be synthesized or otherwise obtained, if desired. Physical testing or computational approaches can be used to determine or predict one or more physicochemical, pharmacokinetic and/or pharmacodynamic properties of compounds identified in a screen. For example, solubility, absorption, distribution, metabolism, and excretion (ADME) parameters can be experimentally determined or predicted. Such information can be used, e.g., to select hits for further testing, development, or modification. For example, small molecules having characteristics typical of "drug-like" molecules can be selected and/or small molecules having one or more unfavorable characteristics can be avoided or modified to reduce or eliminated such unfavorable characteristic(s).

Additional compounds, e.g., analogs, that have a desired activity can be identified or designed based on compounds identified in a screen. In some embodiments structures of hit compounds are examined to identify a pharmacophore, which can be used to design additional compounds. An additional compound may, for example, have one or more altered, e.g., improved, physicochemical, pharmacokinetic (e.g., absorption, distribution, metabolism and/or excretion) and/or pharmacodynamic properties as compared with an initial hit or may have approximately the same properties but a different structure. For example, a compound may have higher affinity for the molecular target of interest, lower affinity for a non-target molecule, greater solubility (e.g., increased aqueous solubility), increased stability, increased bioavailability, oral bioavailability, and/or reduced side effect(s), modified onset of therapeutic action and/or duration of effect. An improved property is generally a property that renders a compound more readily usable or more useful for one or more intended uses. Improvement can be accomplished through empirical modification of the hit structure (e.g., synthesizing compounds with related structures and testing them in cell-free or cell-based assays or in non-human animals) and/or using computational approaches. Such modification can make use of established principles of medicinal chemistry to predictably alter one or more properties. An analog that has one or more improved properties may be identified and used in a composition or method described herein. In some embodiments a molecular target of a hit compound is identified or known. In some embodiments, additional compounds that act on the same molecular target may be identified empirically (e.g., through screening a compound library) or designed.

Data or results from testing an agent or performing a screen may be stored or electronically transmitted. Such information may be stored on a tangible medium, which may be a computer-readable medium, paper, etc. In some embodiments a method of identifying or testing an agent comprises storing and/or electronically transmitting information indicating that a test agent has one or more propert(ies) of interest or indicating that a test agent is a "hit" in a particular screen, or indicating the particular result achieved using a test agent. A list of hits from a screen may be generated and stored or transmitted. Hits may be ranked or divided into two or more groups based on activity, structural similarity, or other characteristics Once a candidate agent is identified, additional agents, e.g., analogs, may be generated based on it. An additional agent, may, for example, have increased cancer cell uptake, increased potency, increased stability, greater solubility, or any improved property. In some embodiments a labeled form of the agent is generated. The labeled agent may be used, e.g., to directly measure binding of an agent to a molecular target in a cell. In some embodiments, a molecular target of an agent identified as described herein may be identified. An agent may be used as an affinity reagent to isolate a molecular target. An assay to identify the molecular target, e.g., using methods such as mass spectrometry, may be performed. Once a molecular target is identified, one or more additional screens may be performed to identify agents that act specifically on that target.

Any of a wide variety of agents may be used as a test agent in various embodiments. For example, a test agent may be a small molecule, polypeptide, peptide, amino acid, nucleic acid, oligonucleotide, lipid, carbohydrate, or hybrid molecule. In some embodiments a nucleic acid used as a test agent comprises a siRNA, shRNA, antisense oligonucleotide, aptamer, or random oligonucleotide. In some embodiments a test agent is cell permeable or provided in a form or with an appropriate carrier or vector to allow it to enter cells.

Agents can be obtained from natural sources or produced synthetically. Agents may be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. A compound library may comprise natural products and/or compounds generated using non-directed or directed synthetic organic chemistry. In some embodiments a library is a small molecule library, peptide library, peptoid library, cDNA library, oligonucleotide library, or display library (e.g., a phage display library). In some embodiments a library comprises agents of two or more of the foregoing types. In some embodiments oligonucleotides in an oligonucleotide library comprise siRNAs, shRNAs, antisense oligonucleotides, aptamers, or random oligonucleotides.

A library may comprise, e.g., between 100 and 500,000 compounds, or more. In some embodiments a library comprises at least 10,000, at least 50,000, at least 100,000, or at least 250,000 compounds. In some embodiments compounds of a compound library are arrayed in multiwell plates. They may be dissolved in a solvent (e.g., DMSO) or provided in dry form, e.g., as a powder or solid. Collections of synthetic, semi-synthetic, and/or naturally occurring compounds may be tested. Compound libraries can comprise structurally related, structurally diverse, or structurally unrelated compounds. Compounds may be artificial (having a structure invented by man and not found in nature) or naturally occurring. In some embodiments compounds that have been identified as "hits" or "leads" in a drug discovery program and/or analogs thereof. In some embodiments a library may be focused (e.g., composed primarily of compounds having the same core structure, derived from the same precursor, or having at least one biochemical activity in common). Compound libraries are available from a number of commercial vendors such as Tocris BioScience, Nanosyn, BioFocus, and from government entities such as the U.S. National Institutes of Health (NIH). In some embodiments a test agent is not an agent that is found in a cell culture medium known or used in the art, e.g., for culturing vertebrate, e.g., mammalian cells, e.g., an agent provided for purposes of culturing the cells. In some embodiments, if the agent is one that is found in a cell culture medium known or used in the art, the agent may be used at a different, e.g., higher, concentration when used as a test agent in a method or composition described herein.

In some aspects methods described herein may comprise measuring the effect of an agent (e.g., a test agent) on the activity or expression level of a sideroflexin in a cell. In some embodiments native gel electrophoresis may be used to measure the level of sideroflexin. In some aspects the ability of sideroflexin to transport or transfer serine is measured. Transport and transfer are used interchangeably throughout the application in the context of sideroflexin activity. In some aspects the ability of sideroflexin to permit survival and/or proliferation of a cell in glycine-deficient medium is measured. In some embodiments two or more properties of a sideroflexin are measured.

In some embodiments the methods comprise identifying an agent that modulates the expression or activity of a sideroflexin (e.g., SFXN1) using a reporter assay. In some embodiments, a sideroflexin enhancer (e.g., a SFXN1 enhancer) is operably linked to a sequence that encodes a reporter gene product (e.g., a luciferase enzyme). In some aspects the expression of the reporter gene is correlated with activity of the sideroflexin. In some aspects a cell containing the sideroflexin enhancer operably linked to a sequence that encodes the reporter gene product is contacted with a test agent and the expression of the reporter gene is measured. In some embodiments the test agent is identified as modulator of the sideroflexin if the expression of the reporter gene product in the contacted cell is increased or decreased as compared to expression of a sideroflexin enhancer operably linked to a sequence that encodes a reporter gene product in a cell that is not contacted with a test agent.

Methods and Compositions for Treating Disease

Some aspects of the disclosure are directed to a method of treating a disease in a subject in need thereof, comprising administering a sideroflexin modulator to the subject. In some embodiments the sideroflexin modulator increases expression or activity of a sideroflexin, and the subject would benefit from increased sideroflexin activity. In some embodiments, for example, the subject has a deficiency in mitochondrial serine transport. The subject may have a mutation in one or more sideroflexin genes, e.g., SFXN1, resulting in decreased mitochondrial serine and/or cysteine transport. In some embodiments methods of treating such a mutation comprise correcting the mutation or providing a copy of the gene (e.g., SFXN1) that does not contain the mutation. In some embodiments the subject has a deficiency in serine biosynthesis. In some embodiments the subject has reduced expression or activity of a sideroflexin or an enzyme involved in serine biosynthesis. In some embodiments the subject has a deficiency in mitochondrial cysteine transport.

Some aspects of the disclosure are directed to a method of treating a disease in a subject in need thereof, comprising administering a therapeutically effective amount of an agent identified by the methods disclosed herein. The agent may be a modulator (e.g., an inhibitor or an activator) of sideroflexin activity or expression. In some embodiments the disease is a mitochondrial disease. In other embodiments the disease is a cancer. In some embodiments the disease is a disease characterized by changes to the one-carbon metabolism pathway.

In some embodiments a method of treating a disease in a subject in need thereof comprises inhibiting expression of sideroflexin in a cell (e.g., a cancer cell) of the subject. In other embodiments a method of treating a disease in a subject in need thereof comprises promoting expression of sideroflexin in a cell of the subject. In some embodiments a method of treating a disease in a subject in need thereof comprises inhibiting expression of a first sideroflexin in a cell of the subject, and promoting expression of a second sideroflexin in the cell of the subject, where the second sideroflexin is different than the first sideroflexin.

Methods of treating a disease in a subject in need thereof, as described herein, may further include modulating (e.g., inhibiting) expression or activity of SHMT1 and/or SHMT2 in the cell. In some aspects methods of treating a disease in a subject in need thereof further include modulating (e.g., inhibiting) expression or activity of MTHFD2. In some embodiments methods of treating a disease in a subject in need thereof include inhibiting expression or activity of SHMT1, SHMT2, and MTHFD2 in a cell (e.g., a cancer cell).

In some aspects methods of treating a disease include administering a modulator of at least one sideroflexin in combination with a co-therapy. In some embodiments the co-therapy is administering a chemotherapy treatment or regime (e.g., chemotherapy drugs and/or radiation). In some embodiments the co-therapy is administering an anti-tumor agent. The anti-tumor agent may be selected to target one-carbon metabolism. In some aspects the anti-tumor agent is methotrexate. In some embodiments the co-therapy is administering radiation therapy.

Methods of treating a disease in a subject in need thereof, as described herein, may further include modulating (e.g., inhibiting) serine synthesis in a cell. In some embodiments serine synthesis is inhibited in a cancer cell. In some aspects modulating serine synthesis in a cell includes inhibiting activity or expression of one or more genes of serine biosynthesis (e.g., PHGDH, PSAT1, and/or PSPH). Examples of inhibitors of PHGDH include those described in WO 2017/117532 and WO 2017/156179, which are incorporated herein by reference.

As used herein, a "subject" is a mammal, including but not limited to a primate (e.g., a human), rodent (e.g., mouse or rat) dog, cat, horse, cow, pig, sheep, goat, or chicken. Preferred subjects are human subjects. The human subject may be a pediatric or adult subject.

Whether a subject is deemed "at risk" of having or developing cancer or recurrence of cancer is a determination that may be within the discretion of the skilled practitioner caring for the subject. Any suitable diagnostic test and/or criteria can be used. For example, a subject may be considered "at risk" of having or developing cancer if (i) the subject has a mutation, genetic polymorphism, gene or protein expression profile, and/or presence of particular substances in the blood, associated with increased risk of developing or having cancer relative to other members of the general population not having mutation or genetic polymorphism; (ii) the subject has one or more risk factors such as having a family history of cancer, having been exposed to a carcinogen or tumor-promoting agent or condition, e.g., asbestos, tobacco smoke, aflatoxin, radiation, chronic infection/inflammation, etc., advanced age; (iii) the subject has one or more symptoms of cancer, (iv) the subject has a medical condition that is known to increase the likelihood of cancer, etc. For example, monoclonal gammopathy of undetermined significance (MGUS) is a condition in which a paraprotein is present in the blood but the levels of antibody and the number of plasma cells in the bone marrow are lower than in multiple myeloma and there are no symptoms. MGUS may progress to multiple myeloma, Waldenström's macroglobulinemia, primary amyloidosis, B-cell lymphoma, or chronic lymphocytic leukemia.

As used herein, the type of cancer is not limited. In some embodiments, the cancer is a cancer of a cancer cell type disclosed herein. Cancer includes, but is not limited to: breast cancer; biliary tract cancer; bladder cancer; brain cancer (e.g., glioblastomas, medulloblastomas); cervical cancer; choriocarcinoma; colon cancer; endometrial cancer; esophageal cancer; gastric cancer; hematological neoplasms including acute lymphocytic leukemia and acute myelogenous leukemia; T-cell acute lymphoblastic leukemia/lymphoma; hairy cell leukemia; chronic lymphocytic leukemia, chronic myelogenous leukemia, multiple myeloma; adult T-cell leukemia/lymphoma; intraepithelial neoplasms including Bowen's disease and Paget's disease; liver cancer; lung cancer; lymphomas including Hodgkin's disease and lymphocytic lymphomas; neuroblastoma; melanoma; oral cancer including squamous cell carcinoma; ovarian cancer including ovarian cancer arising from epithelial cells, stromal cells, germ cells and mesenchymal cells; neuroblastoma, pancreatic cancer; prostate cancer; rectal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullary carcinoma.

In some aspects the methods of treating a disease include inhibiting tumor cell survival or proliferation. A tumor is typically characterized by excessive cell proliferation that is not appropriately regulated (e.g., that does not respond normally to physiological influences and signals that would ordinarily constrain proliferation) and may exhibit one or more of the following properties: dysplasia (e.g., lack of normal cell differentiation, resulting in an increased number or proportion of immature cells); anaplasia (e.g., greater loss of differentiation, more loss of structural organization, cellular pleomorphism, abnormalities such as large, hyperchromatic nuclei, high nuclear:cytoplasmic ratio, atypical mitoses, etc.); invasion of adjacent tissues (e.g., breaching a basement membrane); and/or metastasis. It will be appreciated that a variety of different tumor types can arise in certain organs, which may differ with regard to, e.g., clinical and/or pathological features and/or molecular markers. Tumors arising in a variety of different organs are discussed, e.g., in DeVita, supra or in the WHO Classification of Tumours series, 4th ed, or 3rd ed (Pathology and Genetics of Tumours series), by the International Agency for Research on Cancer (IARC), WHO Press, Geneva, Switzerland, all volumes of which are incorporated herein by reference.

In some embodiments a cancer cell (e.g., a tumor cell) is a brain tumor cell, e.g., a glioblastoma cell. In some embodiments a tumor cell is a bladder tumor cell, breast tumor cell, cervical tumor cell, colorectal tumor cell, embryonal tumor cell, gastric tumor cell, germ cell tumor cell, head and neck tumor cell, hematologic tumor cell, kidney tumor cell, melanoma cell, mesothelial tumor cell, ovarian tumor cell, yolk sac tumor cell, or sarcoma cell. In some embodiments a breast tumor cell is a triple negative breast tumor cell. As known in the art, a "triple negative" breast tumor is a breast tumor that does not express estrogen receptor (ER), progesterone receptor (PR), or Her2/neu. In general, triple negative breast tumors typically have a worse prognosis than breast tumor that are not triple negative.

In some aspects a cancer for treatment may exhibit an increased level of expression or activity of at least one sideroflexin. In some embodiments a cancer for treatment may exhibit an increase in mRNA levels of at least one sideroflexin. In some aspects a cancer for treatment may exhibit a 10% to 100%, e.g., 15% to 95%, 20% to 90%, 25% to 85%, 30% to 80%, or 35% to 75% increase in expression or activity of at least one sideroflexin compared to the sideroflexin in normal tissue. In some aspects a cancer for treatment exhibits at least a 1.5-fold, at least a 2-fold, at least a 2.5-fold, at least a 3-fold, at least a 4-fold, or at least a 5-fold increase in mRNA levels of the at least one sideroflexin compared to the sideroflexin in normal tissue. In some embodiments a cancer for treatment exhibits a 1.5-fold to 2.5-fold, e.g., a 1.8-fold to 2-fold increase in mRNA levels of the at least one sideroflexin compared to the sideroflexin in normal tissue. In some aspects the at least one sideroflexin is SFXN1, SFXN2, or SFXN5. In some aspects a cancer for treatment exhibits at least a 1.5-fold, at least a 2-fold, at least a 2.5-fold, at least a 3-fold, at least a 4-fold, or at least a 5-fold increase in protein levels of the at least one sideroflexin compared to the sideroflexin in normal tissue. In some aspects the cancer is breast cancer.

In some aspects a cancer for treatment may exhibit an increased level of expression or activity of the Myc transcription factor. In some aspects the increased level of expression or activity of Myc is due to mutation, amplification, and/or chromosomal translocation. In some aspects a cancer for treatment may exhibit a 10% to 100%, e.g., 15% to 95%, 20% to 90%, 25% to 85%, 30% to 80%, or 35% to 75% increase in expression or activity of Myc compared to Myc in normal tissue. In some aspects a cancer for treatment exhibits at least a 1.5-fold, at least a 2-fold, at least a 2.5-fold, at least a 3-fold, at least a 4-fold, or at least a 5-fold increase in expression or activity of Myc compared to Myc in normal tissue.

As used herein the type of mitochondrial disease is not limited. In some embodiments the mitochondrial disease exhibits changes in the one-carbon metabolism pathway. Non-limiting examples of mitochondrial diseases include mitochondrial myopathy; diabetes (e.g., diabetes mellitus and deafness (DAD)); Leber's hereditary optic neuropathy (LHON); Leigh syndrome, subacute sclerosing encephalopathy; neuropathy, ataxia, retinis, pigmentosa, and ptosis (NARP); myoneurogenic gastrointestinal encephalopathy (MNGIE); myoclonic epilepsy with ragged red fibers (MERRF); mtDNA depletion (e.g., mitochondrial neurogastrointestinal encephalomyopathy (MNGIE)); Huntington's disease; cancer; Alzheimer's disease; Parkinson's disease; bipolar disorder; schizophrenia; agent and senescence; anxiety disorders; cardiovascular disease; sarcopenia; and chronic fatigue syndrome.

As used herein "treatment" or "treating", in reference to a subject, includes amelioration, cure, and/or maintenance of a cure (i.e., the prevention or delay of relapse and/or reducing the likelihood of recurrence) of a disorder (e.g., cancer). Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). Treating encompasses administration of an agent that may not have an effect on the disorder by itself but increases the efficacy of a second agent administered to the subject. A suitable dose and therapeutic regimen may vary depending upon the specific agent used, the mode of delivery of the compound, and whether it is used alone or in combination.

As used herein, in the context of treatment for cancer, a therapeutically effective amount generally refers to an amount of an agent that inhibits formation, progression, proliferation, growth and/or spread (e.g., metastasis) of a cancer cell or cancer and/or enhances the ability of a second agent to inhibit formation, progression, proliferation, growth and/or spread (e.g., metastasis) of a cancer cell or cancer. In some embodiments, a therapeutically effective amount is an amount of an agent sufficient to inhibit proliferation of a cancer cell. A therapeutically effective amount can refer to any one or more of the agents or compositions described herein, or discovered using the methods described herein, that inhibit the survival and/or proliferation of cancer cells.

In some embodiments, a therapeutically effective amount is an amount of an agent sufficient to modulate a level or activity of at least one sideroflexin (e.g., SFXN1, SFXN2, SFXN3, SFXN4, and/or SFXN5) by at least 5%, e.g., by at least 10%, 20%, 30%, 40%, 50%, 60%, 70%, 80%, 90%, or 100%, e.g., by between 25% and 100%.

The dosage, administration schedule and method of administering the agent are not limited. In certain embodiments a reduced dose may be used when two or more agents are administered in combination either concomitantly or sequentially. The absolute amount will depend upon a variety of factors including other treatment(s), the number of doses and the individual patient parameters including age, physical condition, size and weight. These are factors well known to those of ordinary skill in the art and can be addressed with no more than routine experimentation. In some embodiments, a maximum tolerated dose may be used, that is, the highest safe and tolerable dose according to sound medical judgment. Therapeutic doses of anticancer agents are well known in the field of medicine for the treatment of cancer.

As used herein, pharmaceutical compositions comprise one or more agents or compositions that have therapeutic utility, and a pharmaceutically acceptable carrier, e.g., a carrier that facilitates delivery of agents or compositions. Agents and pharmaceutical compositions disclosed herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of condition (e.g., cancer) to be treated, compounds of the invention may, for example, be inhaled, ingested or administered by systemic routes. Thus, a variety of administration modes, or routes, are available. The particular mode selected will typically depend on factors such as the particular compound selected, the particular condition being treated and the dosage required for therapeutic efficacy. The methods described herein, generally speaking, may be practiced using any mode of administration that is medically acceptable, meaning any mode that produces acceptable levels of efficacy without causing clinically unacceptable adverse effects. Preferred modes of administration are parenteral and oral routes. The term "parenteral" includes subcutaneous, intravenous, intramuscular, intraperitoneal, and intrasternal injection, or infusion techniques. In some embodiments, inhaled medications are of particular use because of the direct delivery to the lung, for example in lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. In some embodiments agents are delivered by pulmonary aerosol. Other appropriate routes will be apparent to one of ordinary skill in the art.

Some embodiments comprise administering to a subject a therapeutically effective amount of a sideroflexin inhibitor and an anti-cancer agent (e.g., an anti-tumor agent). "Administered in combination" means that two or more agents are administered to a subject. Such administration is sometimes referred to herein as "combination therapy", "combined administration", or "coadministration". The agents may be administered in the same composition or separately. When they are coadministered, agents may be administered simultaneously or sequentially and in either instance, may be administered separately or in the same composition, e.g., a unit dosage form that includes both a sideroflexin inhibitor and an anti-cancer agent. When administered separately, the agents may be administered in any order, provided that they are given sufficiently close in time to have a desired effect such as, e.g., inhibiting cancer cell proliferation or survival. "Therapeutically effective amounts" of agents administered in combination means that the amounts administered are therapeutically effective at least when the agents are administered in combination or as part of a treatment regimen that includes the agents and one or more additional agents. In some embodiments, administration in combination of first and second agents is performed such that (i) a dose of the second agent is administered before more than 90% of the most recently administered dose of the first agent has been metabolized to an inactive form or excreted from the body; or (ii) doses of the first and second agent are administered within 48 hours of each other, or (iii) the agents are administered during overlapping time periods (e.g., by continuous or intermittent infusion); or (iv) any combination of the foregoing. In some embodiments, three or more agents are administered and the afore-mentioned criteria are met with respect to all agents, or in some embodiments, the criteria are met if each agent is considered a "second agent" with respect to at least one other agent of the combination. In some embodiments, agents may be administered individually at substantially the same time (e.g., within less than 1, 2, 5, or 10 minutes of one another). In some embodiments they may be administered individually within a short time of one another (by which is meant less than 3 hours, sometimes less than 1 hour, sometimes within 10 or 30 minutes apart). In some embodiments, agents may be administered one or more times within 1, 2, 3, 4, 5, or 6 weeks of each other. In certain embodiments of combination therapy, the first agent is administered during the entire course of administration of the second agent; where the first agent is administered for a period of time that is overlapping with the administration of the second agent, e.g. where administration of the first agent begins before the administration of the second agent and the administration of the first agent ends before the administration of the second agent ends; where the administration of the second agent begins before the administration of the first agent and the administration of the second agent ends before the administration of the first agent ends; where the administration of the first agent begins before administration of the second agent begins and the administration of the second agent ends before the administration of the first agent ends; where the administration of the second agent begins before administration of the first agent begins and the administration of the first agent ends before the administration of the second agent ends. In some embodiments, agents may be administered in alternate weeks. The agents may, but need not, be administered by the same route of administration. A treatment course might include one or more treatment cycles, each of which may include one or more doses of a first agent, and one or more doses of a second agent.

Some aspects of the invention are directed to a composition comprising an agent identified by the methods described herein. In some embodiments, the composition further comprises an anti-cancer agent (e.g., an anti-tumor agent).

In addition to the active agent(s), the pharmaceutical compositions typically comprise a pharmaceutically-acceptable carrier. The term "pharmaceutically-acceptable carrier", as used herein, means one or more compatible solid or liquid vehicles, fillers, diluents, or encapsulating substances which are suitable for administration to a human or non-human animal. In preferred embodiments, a pharmaceutically-acceptable carrier is a non-toxic material that does not interfere with the effectiveness of the biological activity of the active ingredients. The term "compatible", as used herein, means that the components of the pharmaceutical compositions are capable of being comingled with an agent, and with each other, in a manner such that there is no interaction which would substantially reduce the pharmaceutical efficacy of the pharmaceutical composition under ordinary use situations. Pharmaceutically-acceptable carriers should be of sufficiently high purity and sufficiently low toxicity to render them suitable for administration to the human or non-human animal being treated.

Some examples of substances which can serve as pharmaceutically-acceptable carriers are pyrogen-free water; isotonic saline; phosphate buffer solutions; sugars such as lactose, glucose, and sucrose; starches such as corn starch and potato starch; cellulose and its derivatives, such as sodium carboxymethylcellulose, ethylcellulose, cellulose acetate; powdered tragacanth; malt; gelatin; talc; stearic acid; magnesium stearate; calcium sulfate; vegetable oils such as peanut oil, cottonseed oil, sesame oil, olive oil, corn oil and oil of theobrama; polyols such as propylene glycol, glycerin, sorbitol, mannitol, and polyethylene glycol; sugar; alginic acid; cocoa butter (suppository base); emulsifiers, such as the Tweens; as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present. It will be appreciated that a pharmaceutical composition can contain multiple different pharmaceutically acceptable carriers.

A pharmaceutically-acceptable carrier employed in conjunction with the compounds described herein is used at a concentration or amount sufficient to provide a practical size to dosage relationship. The pharmaceutically-acceptable carriers, in total, may, for example, comprise from about 60% to about 99.99999% by weight of the pharmaceutical compositions, e.g., from about 80% to about 99.99%, e.g., from about 90% to about 99.95%, from about 95% to about 99.9%, or from about 98% to about 99%.

Pharmaceutically-acceptable carriers suitable for the preparation of unit dosage forms for oral administration and topical application are well-known in the art. Their selection will depend on secondary considerations like taste, cost, and/or shelf stability, which are not critical for the purposes of the subject invention, and can be made without difficulty by a person skilled in the art.

Pharmaceutically acceptable compositions can include diluents, fillers, salts, buffers, stabilizers, solubilizers and other materials which are well-known in the art. The choice of pharmaceutically-acceptable carrier to be used in conjunction with the compounds of the present invention is basically determined by the way the compound is to be administered. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof in certain embodiments. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that a compound can be provided as a pharmaceutically acceptable pro-drug, or an active metabolite can be used. Furthermore it will be appreciated that agents may be modified, e.g., with targeting moieties, moieties that increase their uptake, biological half-life (e.g., pegylation), etc.

The agents may be administered in pharmaceutically acceptable solutions, which may routinely contain pharmaceutically acceptable concentrations of salt, buffering agents, preservatives, compatible carriers, adjuvants, and optionally other therapeutic ingredients.

The agents may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

In some embodiments, agents may be administered directly to a tissue, e.g., a tissue in which the cancer cells are found or one in which a cancer is likely to arise. Direct tissue administration may be achieved by direct injection. The agents may be administered once, or alternatively they may be administered in a plurality of administrations. If administered multiple times, the agents may be administered via different routes. For example, the first (or the first few) administrations may be made directly into the affected tissue while later administrations may be systemic.

For oral administration, compositions can be formulated readily by combining the active agent(s) with pharmaceutically acceptable carriers well known in the art. Such carriers enable the agents to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration. For buccal administration, the compositions may take the form of tablets or lozenges formulated in conventional manner.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In certain embodiments, the vehicle is a biocompatible microparticle or implant that is suitable for implantation into the mammalian recipient. Exemplary bioerodible implants that are useful in accordance with this method are described in PCT International Application Publication No. WO 95/24929, entitled "Polymeric Gene Delivery System", which reports on a biodegradable polymeric matrix for containing a biological macromolecule. The polymeric matrix may be used to achieve sustained release of the agent in a subject. In some embodiments, an agent described herein may be encapsulated or dispersed within a biocompatible, preferably biodegradable polymeric matrix. The polymeric matrix may be in the form of a microparticle such as a microsphere (wherein the agent is dispersed throughout a solid polymeric matrix) or a microcapsule (wherein the agent is stored in the core of a polymeric shell). Other forms of polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents may be delivered using the bio-erodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terephthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bio-erodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the peptide, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation. Liposomes, for example, which may comprise phospholipids or other lipids, are nontoxic, physiologically acceptable carriers that may be used in some embodiments. Liposomes can be prepared according to methods known to those skilled in the art. In some embodiments, for example, liposomes may be prepared as described in U.S. Pat. No. 4,522,811. Liposomes, including targeted liposomes, pegylated liposomes, and polymerized liposomes, are known in the art (see, e.g., Hansen C B, et al., Biochim Biophys Acta. 1239(2):133-44, 1995; Torchilin V P, et al., Biochim Biophys Acta, 1511(2): 397-411, 2001; Ishida T, et al., FEBS Lett. 460(1):129-33, 1999). In some embodiments, a lipid-containing particle may be prepared as described in any of the following PCT application publications, or references therein: WO/2011/127255; WO/2010/080724; WO/2010/021865; WO/2010/014895; WO2010147655.

Use of a long-term sustained release implant may be particularly suitable for prophylactic treatment of subjects at risk of developing a recurrent cancer. Long-term release, as used herein, means that the implant is constructed and arranged to delivery therapeutic levels of the active agent for at least 30 days, and preferably 60 days. Long-term sustained release implants are well-known to those of ordinary skill in the art and include some of the release systems described above.

In some embodiments, it may be advantageous to formulate oral or parenteral compositions in dosage unit form for ease of administration and uniformity of dosage. Unit dosage form as used herein refers to physically discrete units suited as unitary dosages for the subject to be treated; each unit containing a predetermined quantity of active compound calculated to produce the desired therapeutic effect in association with the required pharmaceutical carrier.

If desired, toxicity and therapeutic efficacy of an agent or combination of agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. In some embodiments, a compound that exhibits a high therapeutic index may be selected. The data obtained from cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. For any compound used in a method of treatment, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of a relevant parameter, e.g., cancer cell growth or other symptoms) as determined in cell culture. Such information can be used to more accurately determine useful doses in humans. Levels in plasma can be measured, for example, by high performance liquid chromatography. In some embodiments a compound described herein is used at a dose that has been demonstrated to have acceptable safety in at least one clinical trial or is a dose that is an acceptable dose or within an acceptable dose range as specified on an FDA-approved label for the compound. In some embodiments a compound described herein is used at a dose described in a patent or patent application describing such compound.

Generally, treatment of a subject can include a single treatment or, in many cases, can include a series of treatments. A pharmaceutical composition can be administered at various intervals and over different periods of time as required, e.g., multiple times per day, daily, every other day, once or more a week for between about 1 to 10 weeks, between 2 to 8 weeks, between about 3 to 7 weeks, about 4, 5, or 6 weeks, etc. It will be appreciated that multiple cycles of administration may be performed. Numerous variations are possible. The skilled artisan will appreciate that certain factors can influence the dosage and timing required to effectively treat a subject, including but not limited to the severity of the disease or disorder, previous treatments, the general health and/or age of the subject, and other diseases present.

Some aspects of the disclosure are directed to a composition comprising a sideroflexin modulator. In some embodiments, the sideroflexin modulator is a sideroflexin inhibitor. In some embodiments, the sideroflexin modulator is a sideroflexin enhancer. In some embodiments, the composition further comprises an anti-tumor agent. In some aspects, the anti-tumor agent targets one-carbon metabolism. The anti-tumor agent may be methotrexate.

Example 1

One-carbon metabolism generates the one-carbon units required to synthesize many critical metabolites, including nucleotides. The pathway has cytosolic and mitochondrial branches and a key step is the entry, through an unknown mechanism, of serine into mitochondria, where it is converted into glycine and formate. A CRISPR-based genetic screen was used in human cells to identify genes that are synthetic lethal with serine hydroxymethyl transferase-1 (SHMT1), a cytosolic enzyme of the pathway. This screen yielded SFXN1, a multi-pass inner mitochondrial membrane protein of unknown function. Like cells missing mitochondrial components of one-carbon metabolism, those null for SFXN1 are defective in glycine and purine synthesis. Cells lacking SFXN1 and one of its four homologs, SFXN3, have more severe defects, including being auxotrophic for glycine. Several SFXN family members can complement SFXN1-3 double loss, as can their yeast and *Drosophila* orthologues. Purified SFXN1 directly transports serine in vitro. Thus, SFXN1, and likely its homologues, functions as a mitochondrial serine transporter in one-carbon metabolism.

SFXN1 is Required for the Proliferation of Cells in the Absence of Serine

A CRISPR/Cas genetic screen was performed to identify the mitochondrial serine transporter. In a central reaction of one-carbon metabolism, two nuclear-encoded SHMT enzymes catalyze the interconversion of serine and glycine. SHMT1 was deleted in two human blood cancer cell lines, Jurkat leukemic T cells and K562 erythroleukemic cells to make them completely dependent on mitochondrial import and catabolism of serine as shown previously (10). To further increase the stringency of the screening conditions, the fact that cells with deletions of mitochondrial one-carbon pathway genes depend on extracellular serine for proliferation was used (10). Any component of the mitochondrial one-carbon pathway should be required for growth in the absence of serine and thus be identified in the screen.

Figure 1A:
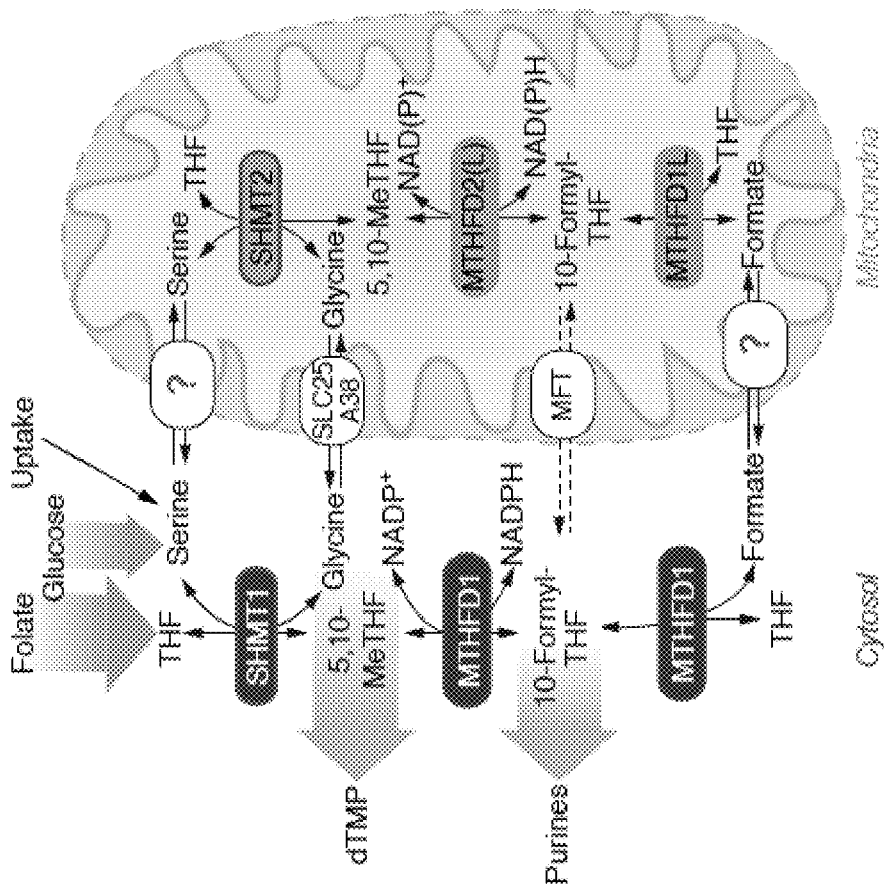
Figure 1C:
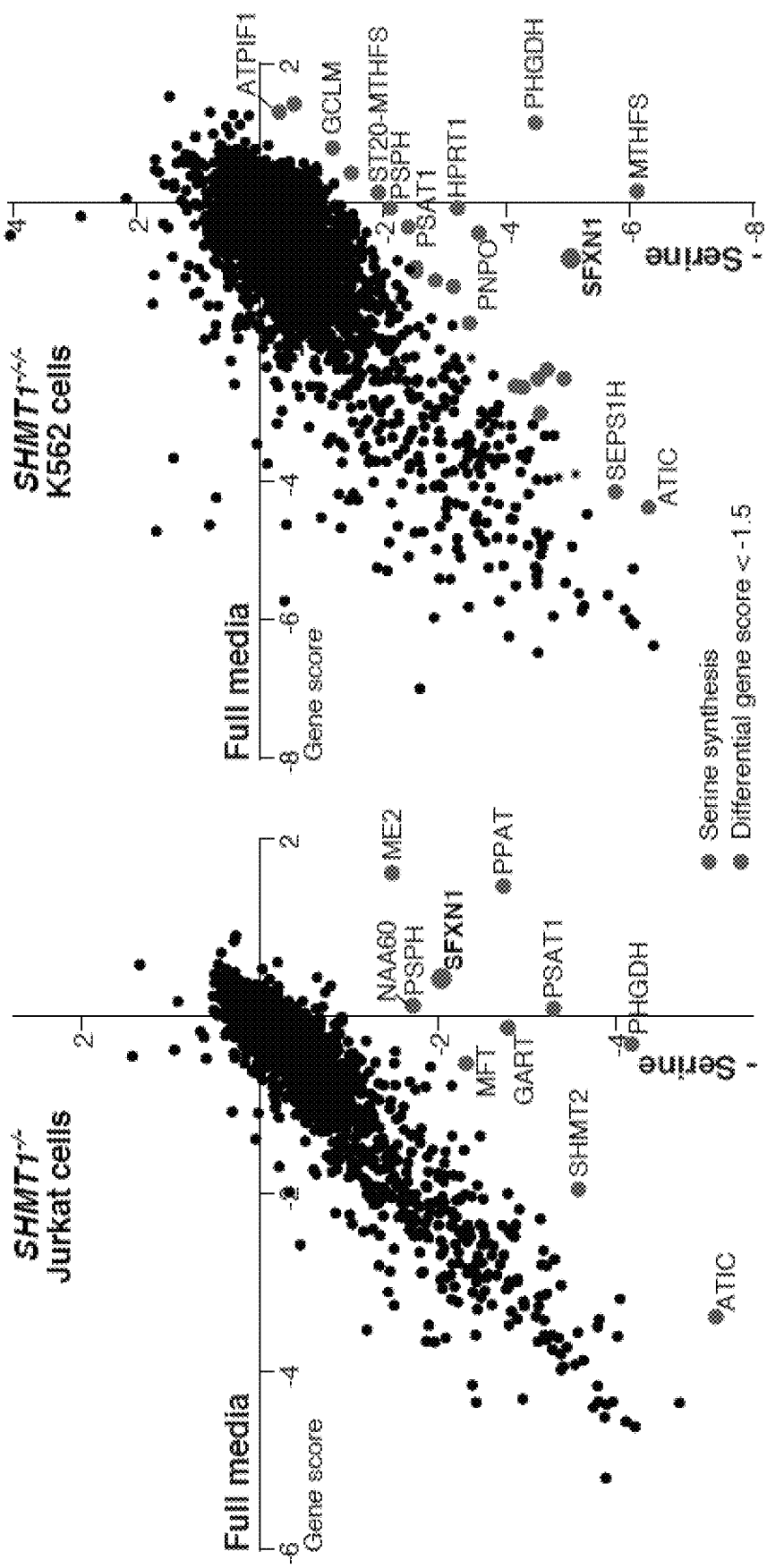
Figure 1D:
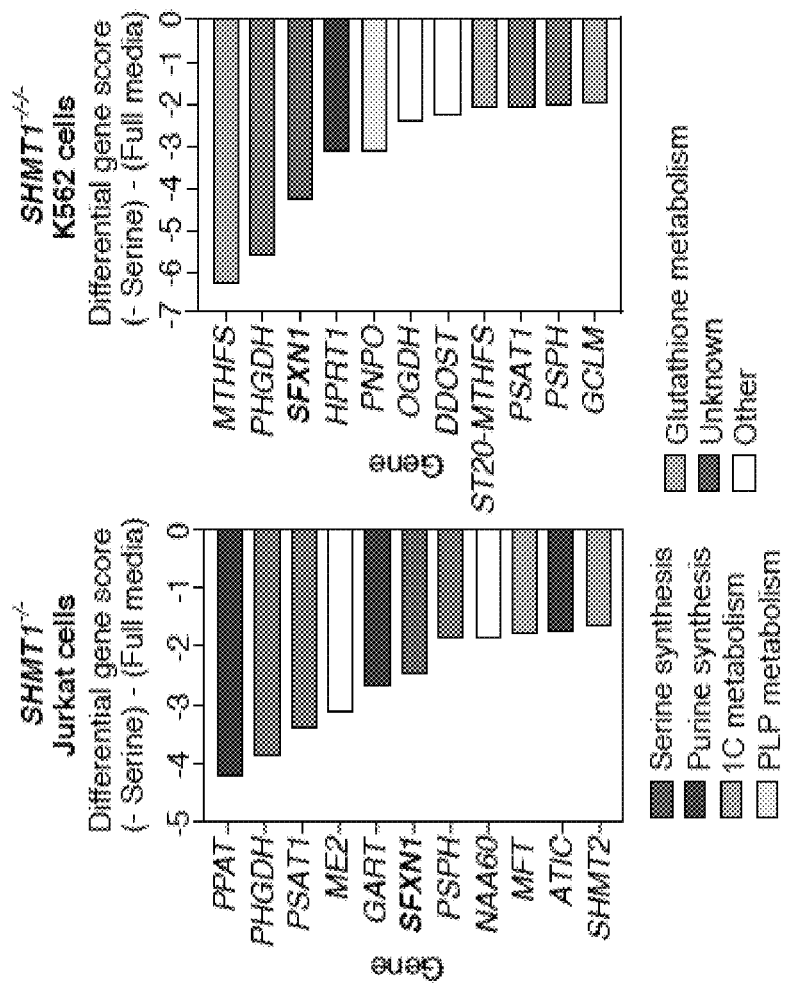

SHMT1-null Jurkat or K562 cells were transduced with a sgRNA library consisting of sgRNAs targeting ~3,000 metabolic enzymes, small molecule transporters, and metabolism-related transcription factors (~10 sgRNA/gene), as well as 500 control sgRNAs in a Cas9-expressing lentiviral vector as described previously (21), and passaged the pool of knockout cells in RPMI media in the presence or absence of serine. Cells grew slower in the absence of serine compared to in full RPMI media, thus cells were collected after ~14 population doublings in full media or ~9 population doublings in serine-deficient media. The abundance of sgRNAs in the cells cultured in the presence and absence of serine was determined at the beginning and at the end of the culture period (FIG. 1B), and for each gene its score was calculated as the mean $\log_2$ fold-change in the abundance of the 10 sgRNAs targeting the gene as described (21). From these values the differential gene score was generated as the difference in gene scores in the absence versus presence of serine. As expected, most genes, as well as the control sgRNAs, scored similarly in both media conditions (FIG. 1C). In both cell lines, the three genes of serine biosynthesis from a glycolysis intermediate, PHGDH, PSAT1 and PSPH, were required for growth in the absence of serine from the culture media. In addition, several genes of the purine synthesis pathway, which is downstream of serine-dependent mitochondrial one-carbon metabolism, were among the genes required for growth specifically in the absence of serine (FIG. 1D). Strikingly, in both cell lines, only one gene of unknown function scored as a hit. Deletion of Sideroflexin 1 (SFXN1), a putative mitochondrial transporter reported to be involved in iron metabolism (22), caused a strong proliferation defect specifically in the absence of serine.

Figures 1E, 1F:
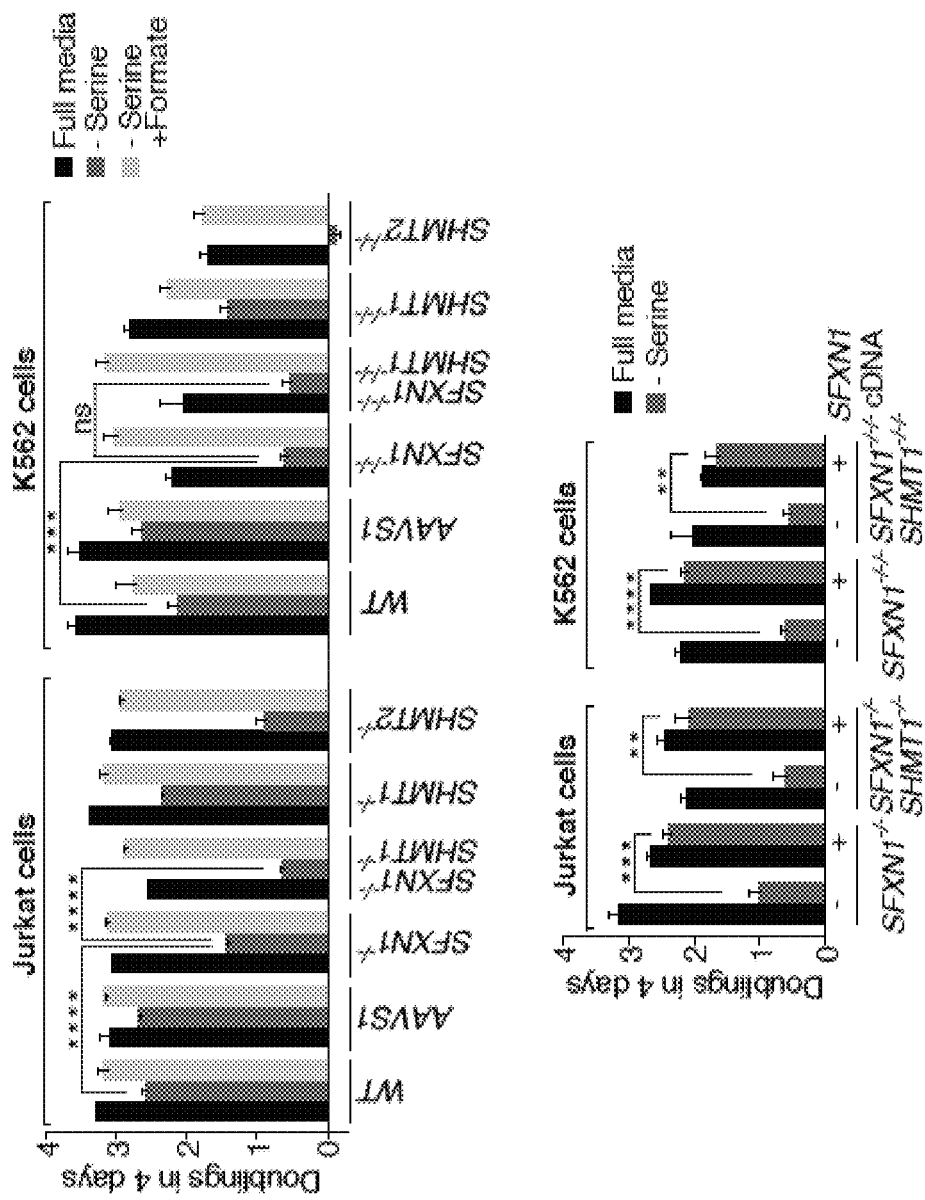

It was confirmed that SFXN1 was required for proliferation in the absence of serine using single cell-derived SFXN1-null clones (FIG. 1E). Loss of SFXN1 alone resulted in a growth defect in the absence of serine in Jurkat and K562 cells. As expected from the screen, the proliferation defect was more pronounced when SFXN1 deletion was combined with loss of SHMT1. Addition of 1 mM formate, the downstream product of the pathway, to serine-deficient media completely restored growth of SFXN1-null cells suggesting the growth defect of SFXN1-null cells is due to an insufficient supply of one-carbon units. Adding back a guide-refractory SFXN1 cDNA to SFXN1-null cells abolished their dependence on extracellular serine (FIG. 1F).

Loss of SFXN1 Phenocopies Mutants in Mitochondrial One-Carbon Metabolism

Figure 2A:
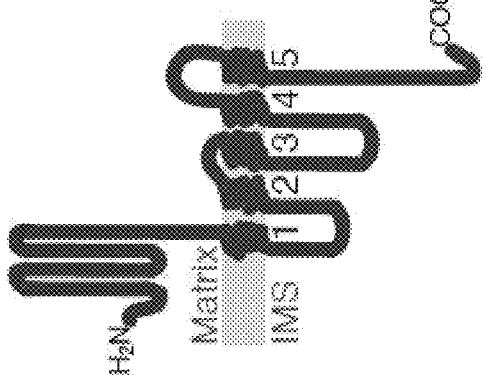
FIGS. 2A-2T demonstrate loss of SFXN1 phenocopies mutants in mitochondrial one-carbon metabolism.

SFXN1 is a mitochondrial protein predicted to contain five transmembrane domains and localize to the inner mitochondrial membrane with its N-terminus facing the mitochondrial matrix and, experimentally confirmed, C-terminus facing the intramembrane space (FIG. 2A) (22, 23).

Figure 2B:
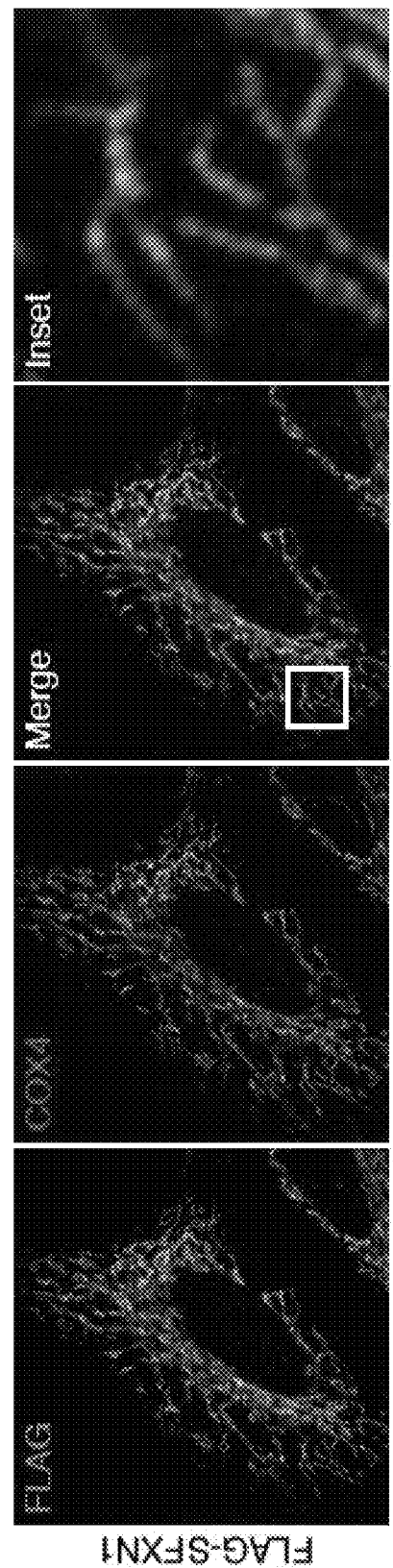
FIG. 2B shows FLAG-tagged SFXN1 localizes to mitochondria. Wild-type HeLa cells transiently expressing FLAG-SFXN1 were processed for immunofluorescence detection of the FLAG epitope (cyan) and the mitochondrial inner membrane marker cytochrome c oxidase 4 (COX4) (magenta). The merged image shows the overlap of both channels in white.
Figures 2C, 2D:
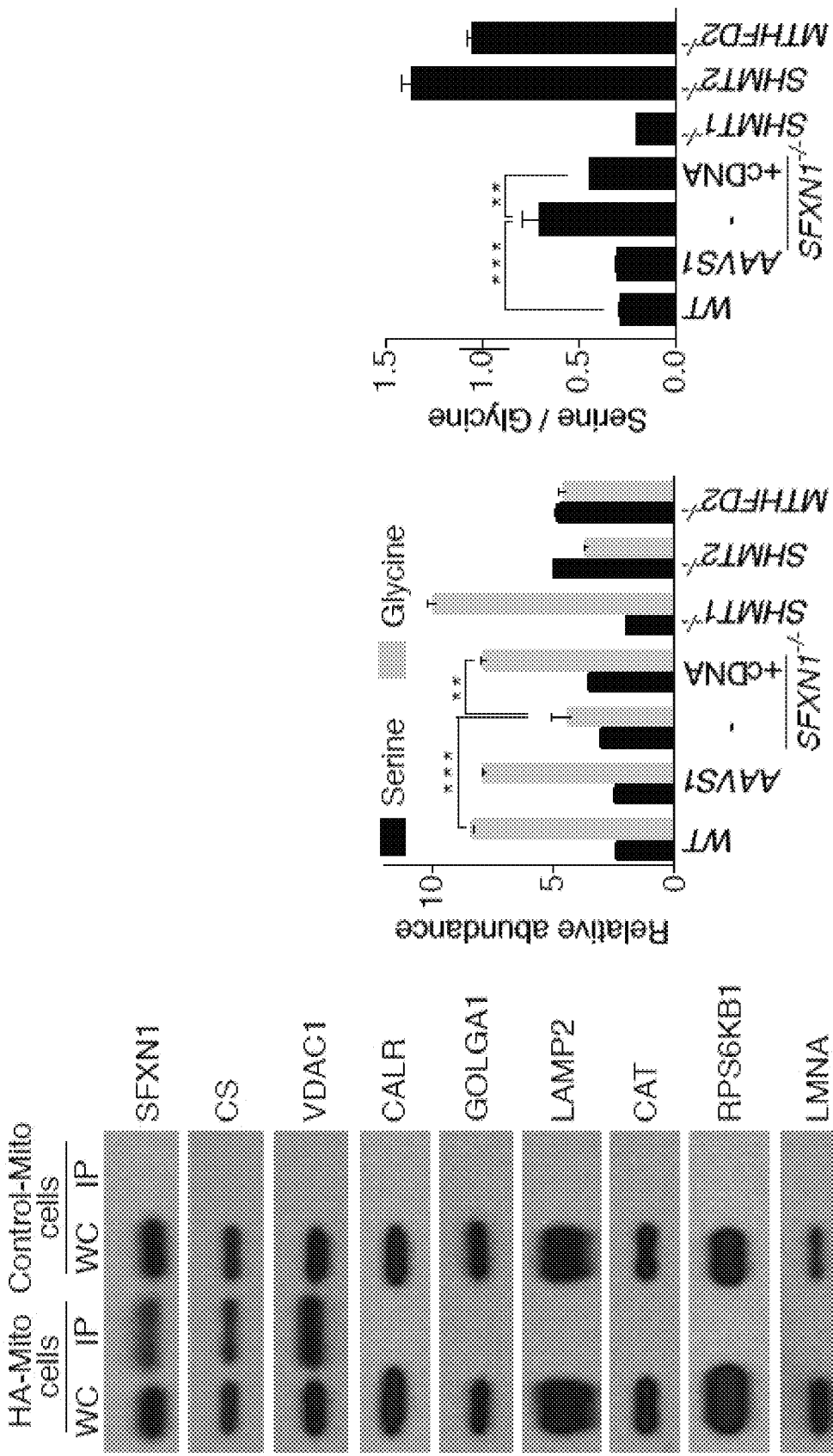
FIG. 2C shows endogenous SFXN1 is present in purified mitochondria. Mitochondria were affinity-purified using the HA-Mito-tag. HA-immunoprecipitates and cell lysates prepared from wild-type Jurkat cells expressing the HA-mito tag or a control mito-tag and were analyzed by immunoblotting for the levels of the indicated proteins.
FIG. 2D shows glycine levels are reduced in SFXN1-null cells and the cellular serine/glycine ratio is increased similarly to cells with deletion of known components of the mitochondrial 1C pathway. Serine and glycine levels were measured by GC/MS in extracts from wild-type Jurkat cells, or single-cell-derived control and knockout clones.
Figures 7A, 7B:
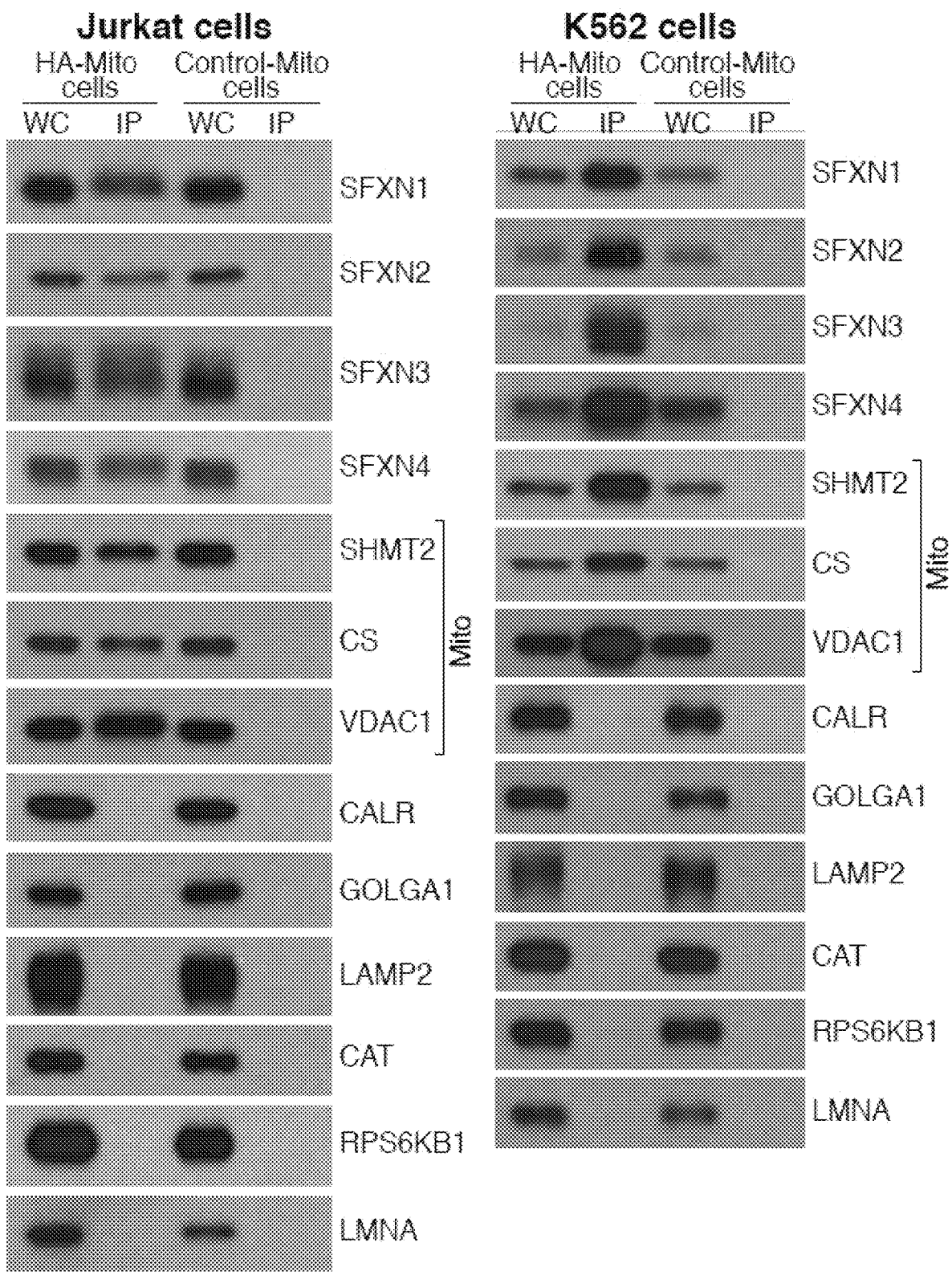
FIGS. 7A-7G demonstrate SFXN1 and SFXN3 are redundant and their fly and yeast homologues can substitute for them.

Confirming these results, it was found that Flag-tagged SFXN1 co-localized with the inner membrane protein COX4 in HeLa cells (FIG. 2B) and that endogenous SFXN1 was enriched in mitochondria purified from Jurkat and K562 cells (FIG. 2C and FIG. 7B). Thus based on its structure and localization, SFXN1 appeared as a good candidate to be a mitochondrial serine transporter.

Figure 2E:
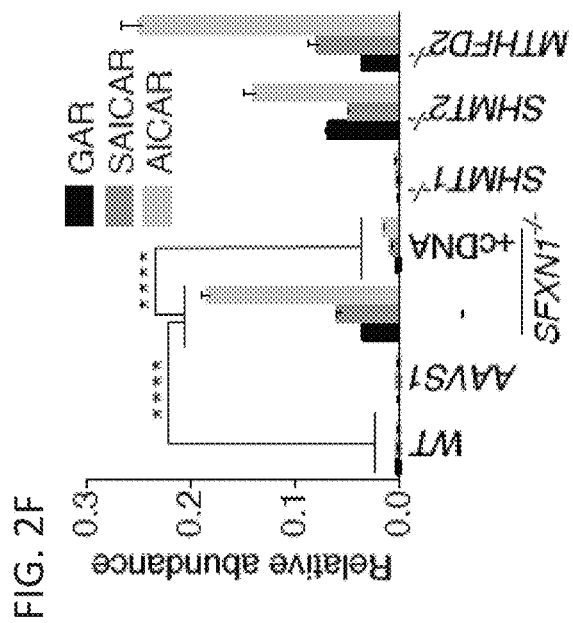
FIG. 2E shows reduced folate species are decreased in SFXN1-null cells. Metabolites were measured by LC/MS in extracts from wild-type Jurkat cells, or single-cell-derived control and knockout clones.
Figure 6A:
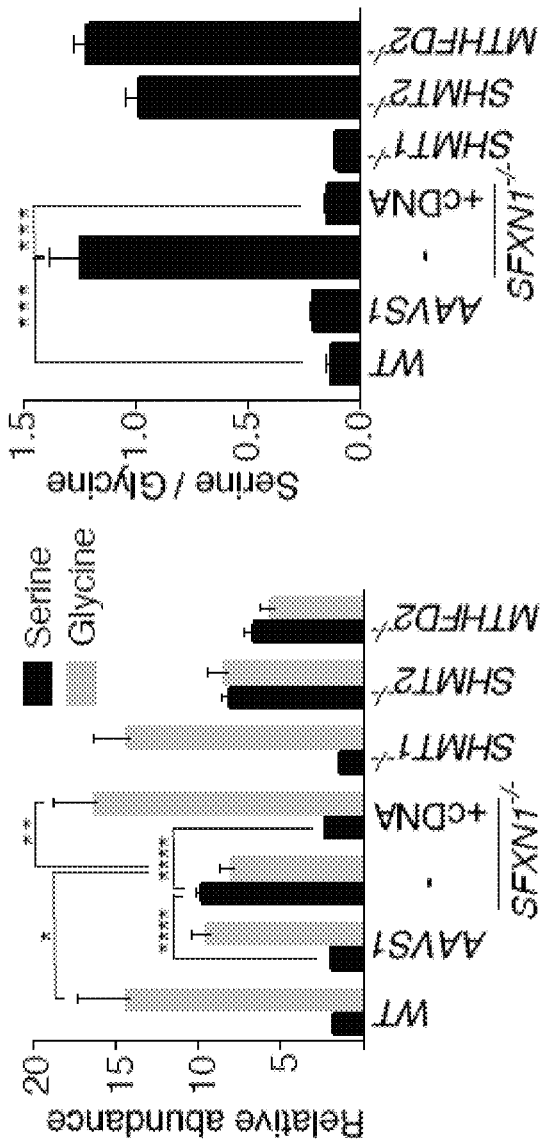
Figure 6B:
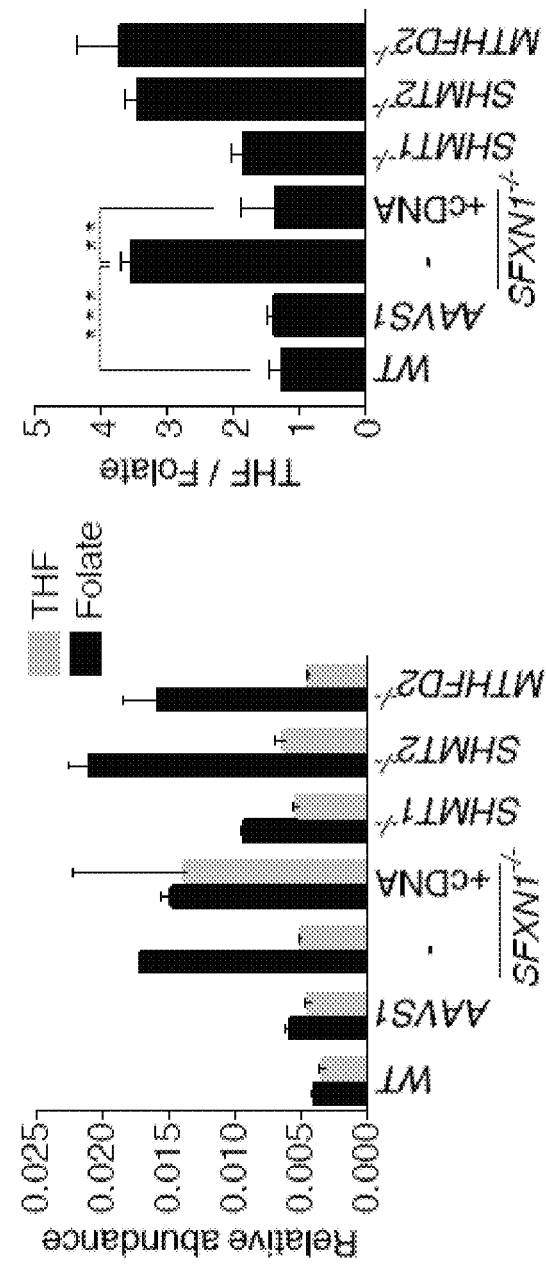

If SFXN1 was part of the mitochondrial one-carbon pathway as a mitochondrial serine importer, it was reasoned that its deletion should result in a similar metabolic phenotype as deletion of SHMT2 or MTHFD2, the main enzymes that generate one-carbon units in mitochondria by converting serine to glycine and formate. Indeed, deletion of SFXN1, SHMT2, and MTHFD2, but not SHMT1, resulted in cellular glycine depletion in Jurkat cells, and more than 2-fold increase in the cellular serine/glycine ratio (FIG. 2D and FIG. 6A). Consistent with a defect in mitochondrial one-carbon metabolism, the detectable one-carbon unit-carrying reduced folate species (5,10-methenyl-THF and 5-formyl-THF) were significantly decreased in SFXN1-null cells (FIG. 2E). The ratio between THF and folate was also affected by SFXN1 deletion and restored by SFXN1 re-expression (FIG. 6B).

Figure 2F:
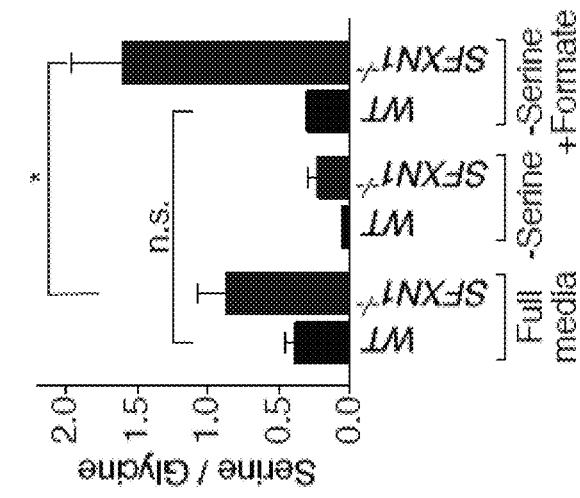
FIG. 2F shows purine intermediates accumulate in SFXN1-null cells. Purine intermediates were measured by LC/MS in extracts from wild-type Jurkat cells, or single-cell-derived control and knockout clones.
Figure 2G:
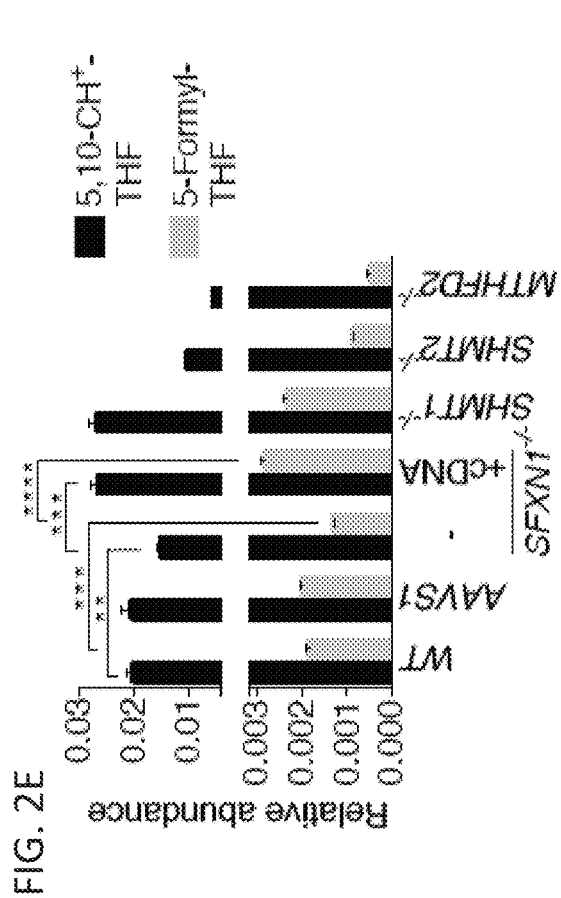
FIG. 2G shows serine depletion lowers serine levels in cells. Serine and glycine levels were measured by LC/MS in extracts from wild-type Jurkat cells, or single-cell-derived SFXN1-null cells incubated for 24 hours in the indicated media.
Figure 2G:
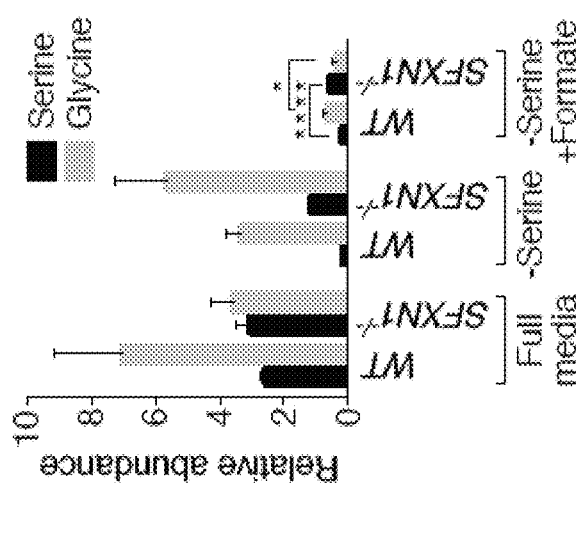
Figure 2H:
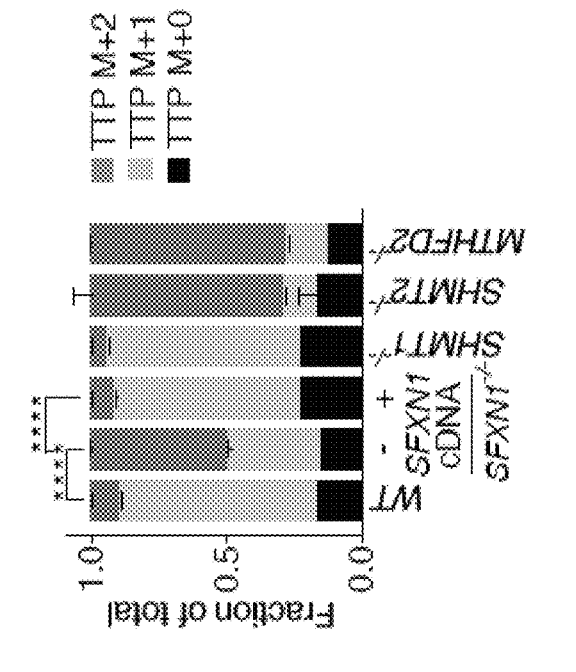
FIG. 2H shows serine depletion causes accumulation of purine synthesis intermediate, addition of formate rescues this. Purine intermediates were measured by LC/MS in extracts from wild-type Jurkat cells, or single-cell-derived SFXN1-null cells incubated for 24 hours in the indicated media.

Whether the reduction in one-carbon unit carrying THF molecules in SFXN1-null cells resulted in one-carbon unit stress was then determined. A major cellular pathway consuming one-carbon units is purine synthesis, which uses 10-formyl-THF as a co-factor (FIG. 6C). Indeed, the purine biosynthesis intermediates GAR, SAICAR, and AICAR accumulated in SFXN1, SHMT2, and MTHFD2-null cells as expected from the insufficient availability of one-carbon units (FIG. 2F and FIG. 6D). In this respect, SFXN1 deletion mimicked serine depletion, which led to an accumulation of these intermediates in WT cells (FIG. 2H). As expected, formate was able to completely abolish their accumulation without rescuing the cellular serine and glycine levels (FIGS. 2G and 2H).

Figure 2I:
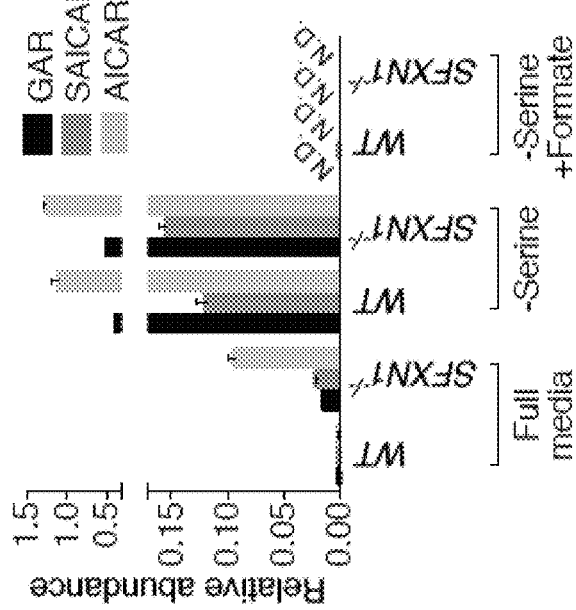
FIG. 2I shows the relative contribution of cytosolic and mitochondrial one-carbon pathways to TTP synthesis is inverted in SFXN1-null compared to wile-type cells. TTP is derived less from mitochondrial 1C metabolism. Wild-type Jurkat, or single-cell-derived knockout cells were cultured for 12 hours in media containing 2,3,3-$^2$H$_3$-serine as the only serine-source before cell harvesting and LC/MS analysis (mean±SD; n=3, ****P<0.0001). TTP—thymidine triphosphate.
Figure 2J:
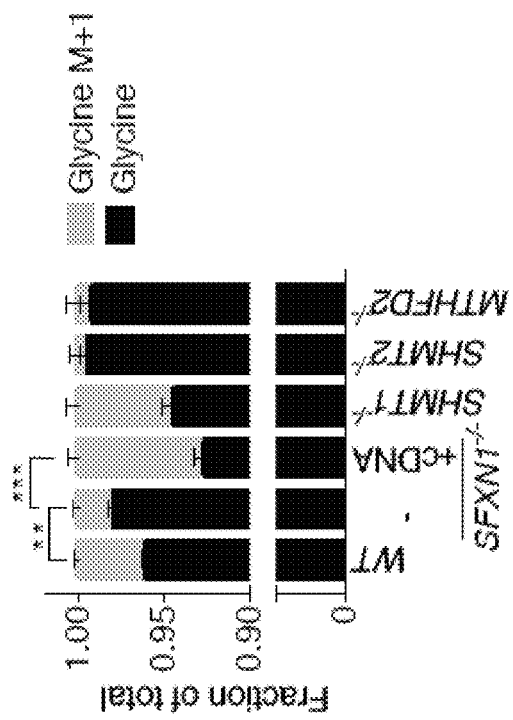
FIG. 2J SFXN1-null cells synthesize and secrete less glycine. Glycine in the culture supernatant from cells in (I) was measured by GC/MS. Mean±SD; n=3, *P<0.05, P<0.01, *P<0.001, **P<0.0001.
Figure 2L:
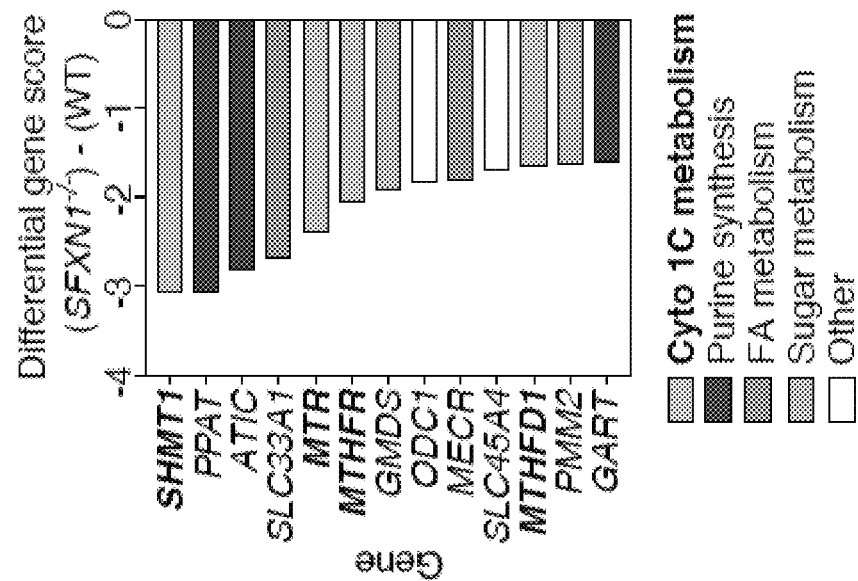
FIGS. 2K and 2L show genes of the cytosolic 1C pathway are selectively essential in SFXN-null cells.
Figure 2K:
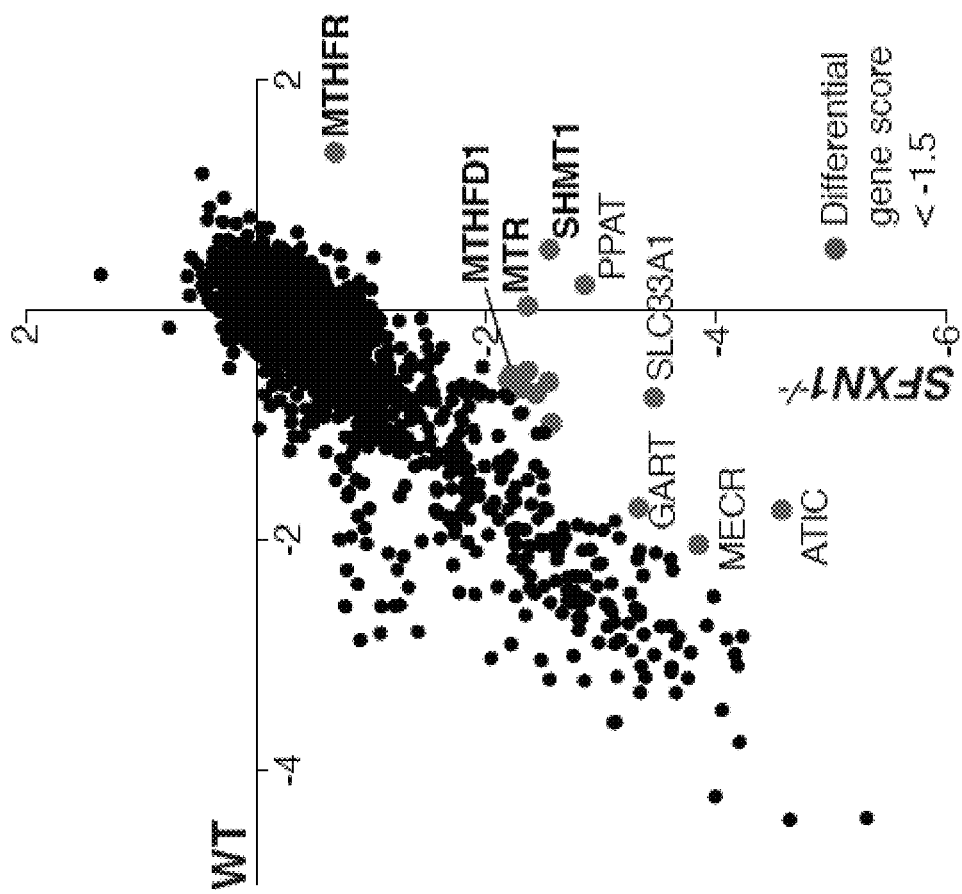

To directly test whether mitochondrial one-carbon metabolism was perturbed in SFXN1-null cells, a recently reported serine tracing approach was adopted (10). Both one-carbon units derived from serine catabolism by SHMT1 in the cytosol and by the mitochondrial one-carbon pathway contribute to thymidine triphosphate (TTP) synthesis. When catabolized in the cytosol, carbon atom 3 of serine is directly incorporated into TTP. When serine is catabolized in mitochondria it is first converted to formate before it gives rise to one-carbon units in the cytosol. Thus, fully deuterated serine will give rise to two mass units shifted TTP M+2 species when it is catabolized in the cytosol or to TTP M+1 species when catabolized in mitochondria (FIG. 6F). The labeling pattern of TTP was compared in wild-type to SFXN1-null cells as well as to SHMT1-, SHMT2- and MTHFD2-null cells. While in wild-type cells the predominant newly synthesized TTP species was mitochondrially derived TTP M+1, the ratio between M+1 and M+2 stemming from the SHMT1 reaction was inverted in SFXN1-, SHMT2- and MTHFD2-null cells, showing that the mitochondrial one-carbon pathway is perturbed and contributes less to TTP synthesis in these cells (FIG. 2I). The amount of de novo synthesized glycine secreted into the media was also decreased in SFXN1-null cells (FIG. 2J). Additionally a SFXN1 synthetic lethality screen was conducted and found that SHMT1 scored as the top gene required for growth of SFXN1-null but not wild-type cells. Several other components of cytosolic one-carbon metabolism were also among the top hits (FIGS. 2K and 2L). Together, these results strongly support the hypothesis that SFXN1 is a new component of the mitochondrial one-carbon pathway and, like established components, its deletion made cells dependent on the cytosolic branch of the pathway.

SFXN1 Transports Serine In Vitro

To test whether SFXN1 is a serine transporter, the Flag-tagged protein made in mammalian cells was purified and reconstituted into liposomes. SFXN1 was able to mediate serine uptake into liposomes (FIG. 3A). Both L- and D-serine were able to complete serine uptake, as was alanine, while other amino acids did so to a negligible extent (FIG. 3B). Formate was not able to complete serine uptake.

Figure 4D:
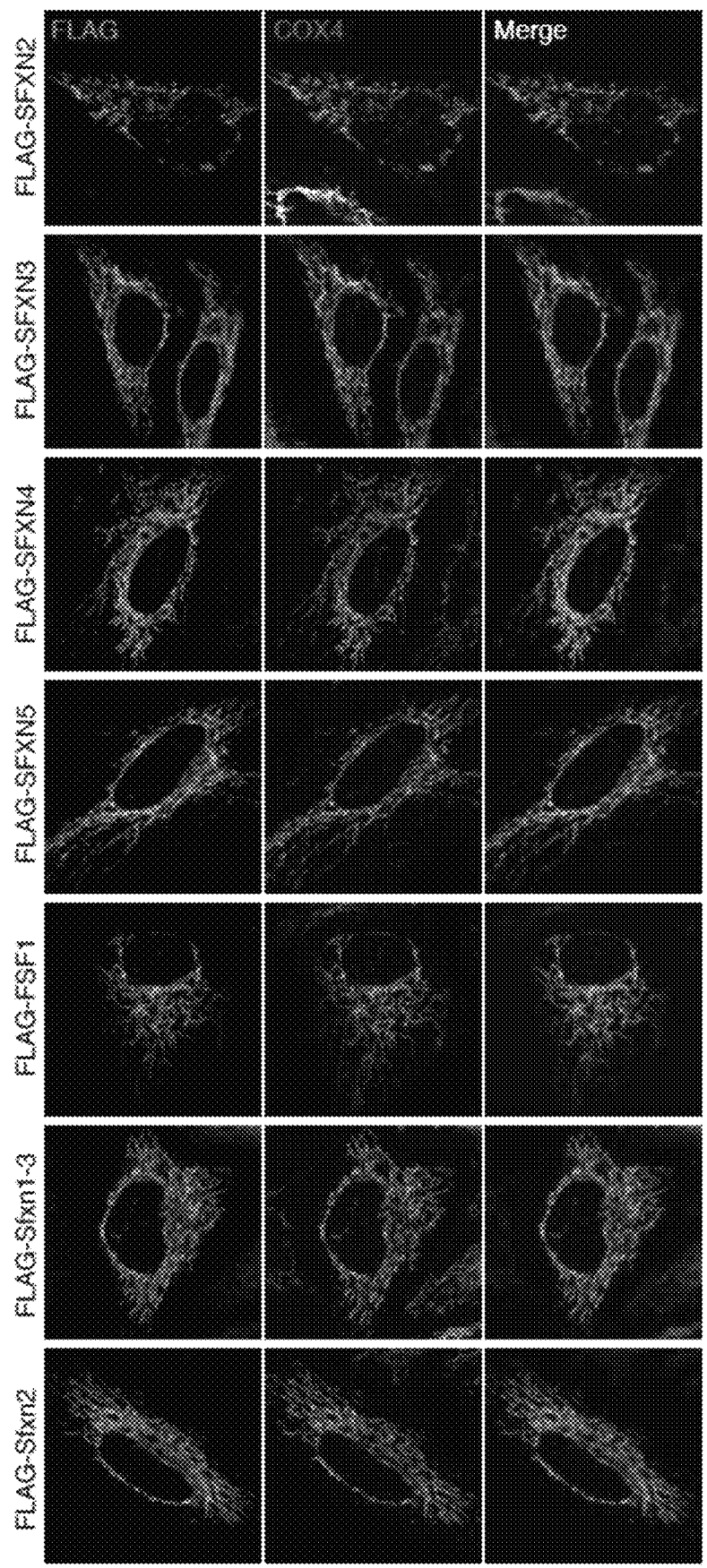

SFXN1 and 3 are Redundant and their Fly and Yeast Homologues can Substitute for them One long appreciated feature of genes required for mitochondrial one-carbon metabolism is that their deletion results in glycine auxotrophy (5, 24, 25), which was confirmed for SHMT2 and MTHFD2. However, as this phenotype was not observed for SFXN1-null cells, it reasoned that there is likely redundancy with other genes. Indeed, Sideroflexin1 is part of the protein family of Sideroflexins, comprising 5 proteins in mammals, and which also has one homolog in yeast (FSF1), and two in *Drosophila*, one being most similar to SFXN1/3 (CG11739) and the other to SFXN2 (CG6812) (FIG. 4A). Multiple Sideroflexin homologs are expressed in Jurkat, K562, and other commonly used cell lines (FIGS. 4B and 4C). All of these Sideroflexin homologs localize to the mitochondria (FIG. 4D and FIG. 7A).

Figure 4E:
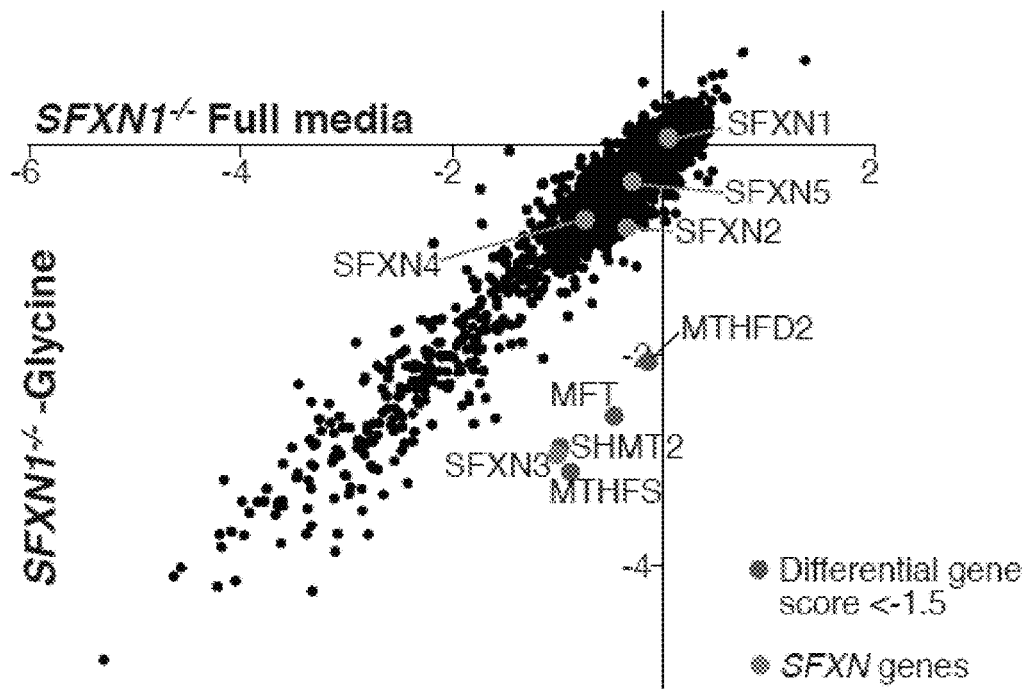

It was considered whether other Sideroflexin family members can substitute at least in part for the loss of SFXN1, which could explain why SFXN1-null cell are not glycine-auxotrophs. A CRISPR screen was performed in SFXN1-null cells in the absence of glycine to identify genes that are required for glycine synthesis and functionally redundant with SFXN1. Besides known genes in the mitochondrial one-carbon pathway and MTHFD1, a central component of one-carbon metabolism in the cytosol, only one other gene, SFXN3, scored (FIG. 4E). SFXN3 is the closest homologue of SFXN1 and highly similar in sequence (88% sequence similarity).

Figure 4F:
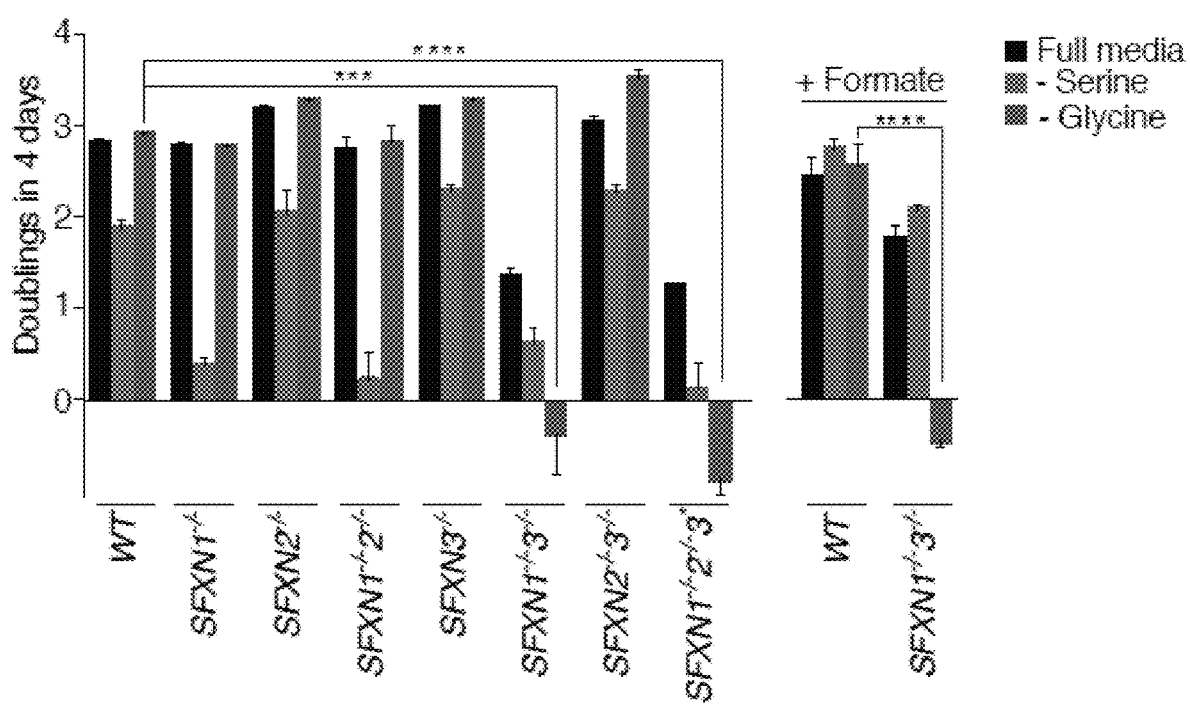
Figure 4H:
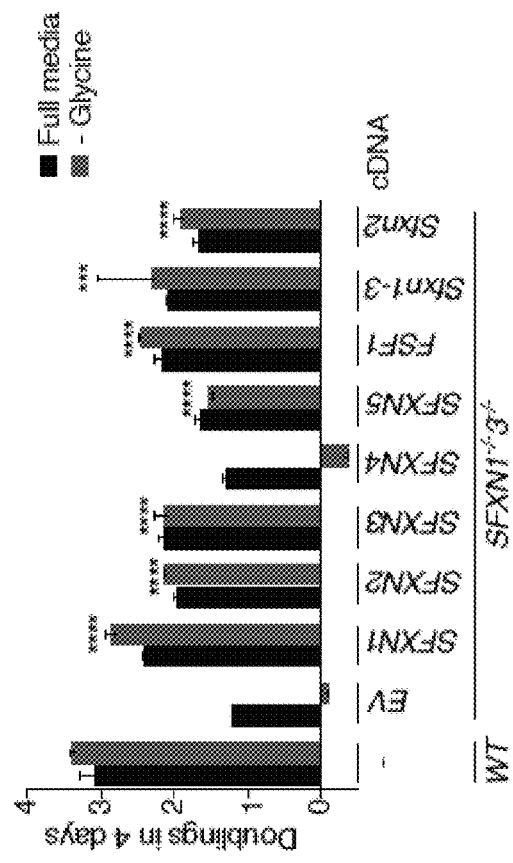
Figure 4G:
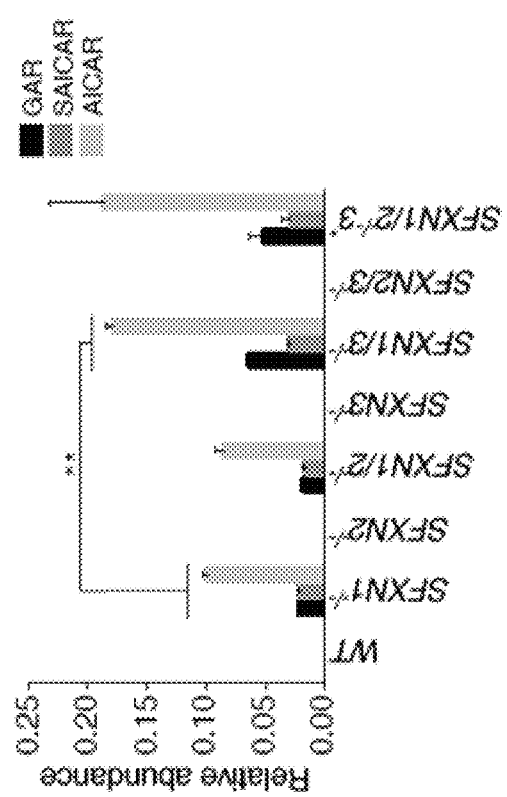
Figure 7C:
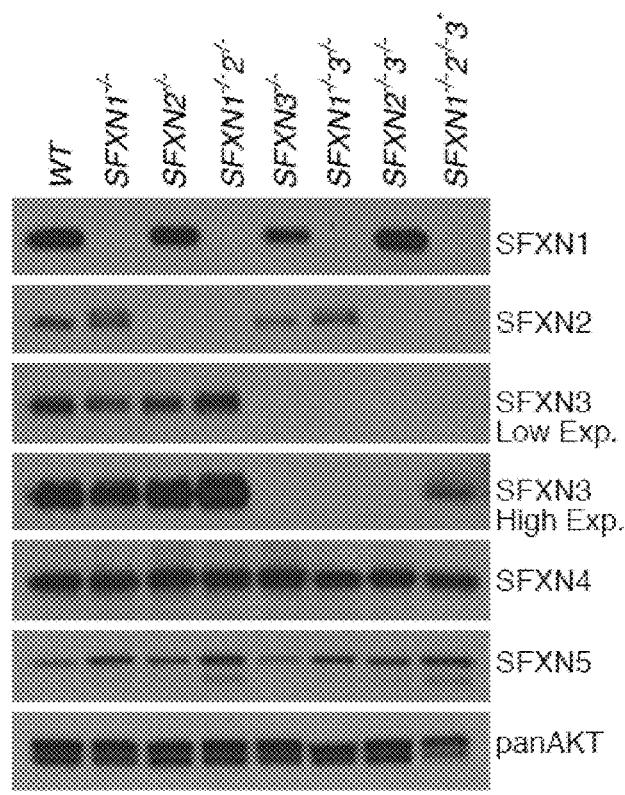
Figure 7D:
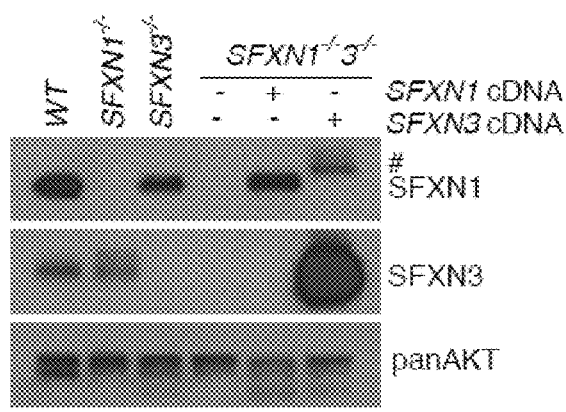
Figure 7E:
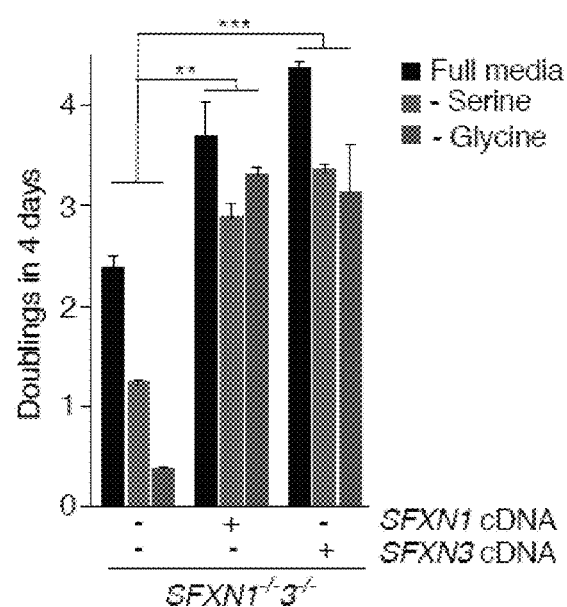
Figure 7F:
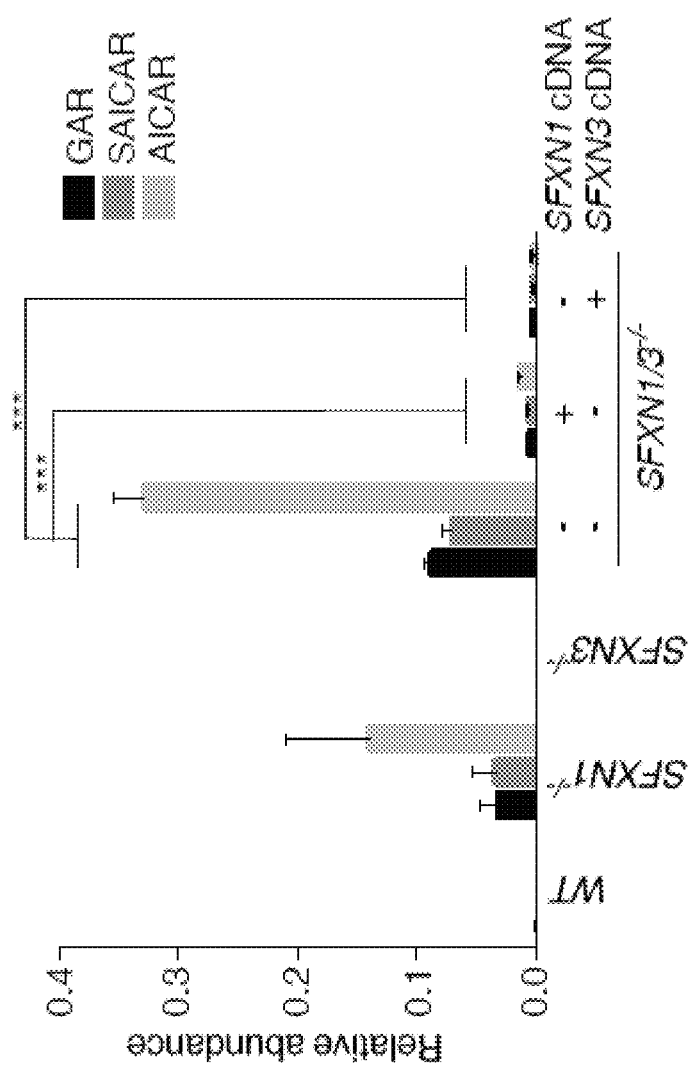

To confirm that SFXN3 was indeed functionally redundant with SFXN1 and compensating for its loss, SFXN1/3-double null cells were generated and their growth was tested in the absence of serine and glycine. Indeed, like SHMT2- and MTHFD2-cells, the SFXN1/3 double knockout cells were unable to grow in the absence of glycine suggesting these cells have a severe defect in glycine synthesis (FIG. 4F). Formate was unable to rescue the growth defect in the absence of glycine (FIG. 4F), while re-expressing either SFXN1 or SFXN3 cDNA (at higher levels than in wild-type cells) was (FIGS. 7D and 7E). Accumulation of purine synthesis intermediates was exacerbated in SFXN1/3 double knockout cells compared to SFXN1-null cells, while deletion of SFXN3 or SFXN2 one at a time or in combination did not have an effect (FIG. 4G). SFXN1/3-double knockout cells grew slower than wild-type cells even in full media, suggesting that in contrast to SFXN1-null cells, the double knockout cells not only experience one-carbon unit stress, but one-carbon units actually become limiting to proliferation. SFXN1/2/3 triple knockout cells were unable to be isolated after multiple attempts, even when supplementing growth media with formate, suggesting these cells are likely not viable. However, one clone null for SFXN1 and 2 was obtained with reduced levels of SFXN3 due to a single codon in-frame deletion (FIG. 7C). This clone was also unable to grow in the absence of glycine (FIG. 4F).

Figure 4I:
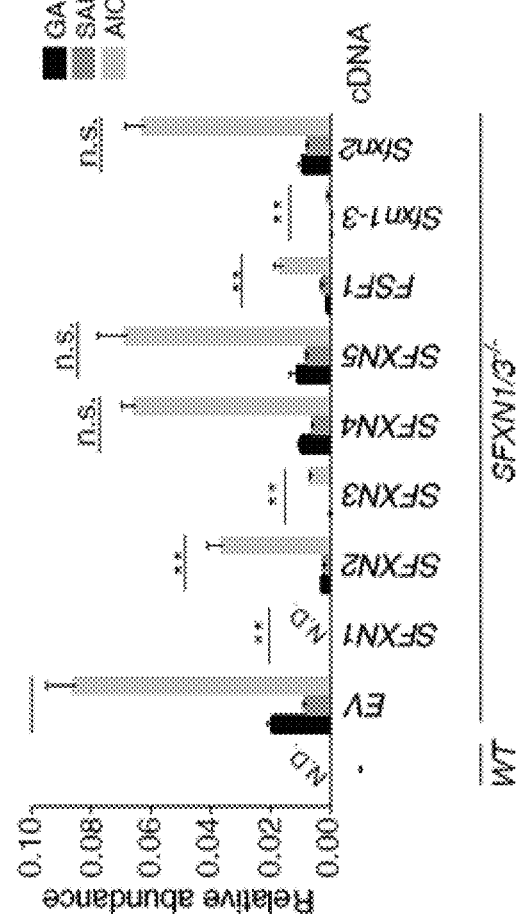

SFXN1 and 3 are among the most highly expressed Sideroflexin homologs in Jurkat cells (FIG. 4B). Other Sideroflexins might function as serine transporters, but might not be expressed at sufficiently high levels in Jurkat cells to compensate for SFXN1 and SFXN3 loss. To test this hypothesis, Sideroflexin homologs were overexpressed in SFXN1/3 double null cells and determined whether they rescued the glycine auxotrophy and one-carbon unit stress in these cells. All Sideroflexin homologs except SFXN4, including the yeast as well as both *Drosophila* homologs, were able to rescue glycine auxotrophy of SFXN1/3-null cells (FIG. 4H). However, besides SFXN1 and 3 only SFXN2 and the *Drosophila* homolog of SFXN1 and 3 were able to rescue the defect in purine synthesis to different degrees (FIG. 4I).

CONCLUSIONS

Here, an evolutionarily conserved function of SFXN1 as a serine transporter in one-carbon metabolism is reported. Based on the results it is expected that besides SFXN1s close homolog SFXN3, likely also SFXN2, SFXN5, yeast and *Drosophila* orthologs can transport serine, but might have different kinetic properties and/or somewhat different substrate specificities. This could explain why their overexpression rescues glycine auxotrophy, but only partially the accumulation of purine synthesis intermediates: their presence allows a sufficient amount of serine to enter mitochondria to support basal glycine synthesis that is able to prevent glycine auxotrophy, but is unable to fully maintain the high rate of serine flux into the pathway required to meet the high demand for one-carbon units in rapidly proliferating cells. Since SFXN4 was not able to rescue even glycine auxotrophy of SFXN1/3-null cells, it likely acts as a transporter for structurally distinct molecules. The in vitro transport system allows for testing substrate specificities and kinetic properties of Sideroflexin homologs and will be an invaluable tool in answering these types of questions.

The results imply that, besides serine, SFXN1 can also transport alanine. Other substrates of SFXN1 may be physiologically relevant. In addition, SFXN1 may be important for cell function besides its role in one-carbon metabolism, for example in providing amino acids for mitochondrial translation.

It has been controversial whether the observed phenotype is indeed due to SFXN1, yet mice with a SFXN1 loss-of-function mutation have been reported to display transient neonatal sideroblastic anemia and accumulate iron in the mitochondria of erythrocyte precursors leading to their dysfunction (22). In humans this condition is caused by deletions in genes of heme and iron-sulfur-cluster metabolism, such as ALAS2, an enzyme in heme synthesis, and SLC25A38, a mitochondrial glycine transporter required for heme synthesis (26, 27). Because serine import is also required for glycine and downstream heme synthesis it is speculated that the defect of SFXN1-mutant mice might be due to insufficient glycine and downstream heme production caused by insufficient serine import into mitochondria. The heme deficiency would lead to a failure to properly incorporate iron transported into mitochondria into its bioactive form and cause consequential aberrant accumulation of likely harmful free iron in mitochondria. It is possible this would be sensed as iron deficiency leading to a positive feedback on iron import into mitochondria and thereby accelerating the toxic accumulation of iron. Because the anemia phenotype in SFXN1-mutant mice is transient, it is possible that other Sideroflexins become upregulated later in development and are able to take over SFXN1 function.

SFXN4 loss-of-function results in anemia similarly to SFXN1, however the phenotypes are distinct from each other in that loss of SFXN4 causes mitochondriopathy in humans (28).

Despite their high conservation and apparently important function Sideroflexins have remained a poorly characterized transporter family until now. Redundancy between the homologs could be one reason why few phenotypes are observed and their molecular function was not previously uncovered. Because their expression varies across tissues, each Sideroflexin homolog might have its major function in a particular organ. Combined and tissue-specific deletion of Sideroflexins will allow dissecting each homolog's role in physiology.

Serine catabolism has garnered much recent interest for its role in tumor metabolism (10, 29-31). As SFXN1 decides over serine fate in the cell and production of one-carbon units as a mitochondrial serine transporter it likely plays an important role in cancer growth.

Materials and Methods

Reagents

Reagents were obtained from the following sources: the antibodies against SFXN1 (HPA019543), SFXN2 (HPA026834), SFXN3 (HPA048105) and SHMT2 (HPA020549) from Atlas Antibodies; the antibodies against AKT (4691), CALR (12238), Catalase (12980), Citrate Synthase (14309), COX4 (4850), GOLGA1 (13192), RPSS6KB1 (2708), SHMT1 (12612), VDAC (4661), the myc (2278) and HA epitopes (3724) and HRP-coupled anti-rabbit secondary antibody from Cell Signaling Technology (CST); the antibodies against the FLAG epitope from CST (2368) and Sigma (F1804); antibodies against LAMP2 (sc-18822), LMNA (sc-20680), MTHFD1 (sc-271412), MTHFD2 (sc-390708) and the HRP-labeled anti-mouse secondary from Santa Cruz Biotechnology; the antibodies against SFXN4 (CSB-PA744046LA01HU) and SFXN5 (CSB-PA819464LA01HU) from Cusabio; the antibody against MTHFD1L (ab116615) from Abcam; 2,3,3-$^2$H$_3$-serine from Cambridge Isotope Laboratories; [3H] Serine from American Radiolabeled Chemicals, Inc.; RPMI and amino acids from Sigma Aldrich; DMEM from SAFC Biosciences; XtremeGene9 and Complete Protease Cocktail from Roche; Alexa 488 and 568-conjugated secondary antibodies and Inactivated Fetal Bovine Serum (IFS) from Invitrogen and Gemini; amino acid- and glucose-free RPMI from US Biologicals; anti-HA magnetic beads from ThermoFisher Scientific, glucose from Westnet Inc. (#BM-675), ANTI-FLAG M1 Agarose Affinity Gel and sodium formate from Sigma; egg phosphatidylcholine, E. coli total lipids, and the lipid extruder from Avanti Polar Lipids; Bio-Beads SM-2 Adsorbents from Biorad Laboratories; filter membranes for extrusion and supports from Whatman.

Cell Lines and Vectors

Materials were obtained from the following sources: K562 cells from ATCC, HeLa cells were a kind gift from Dr. Francesca Bottanelli (Yale University). pMXS-IRES-Bsd vector was purchased from Cell Biolabs, Inc. The identities of K562, Jurkat, and HeLa cells used in this study were authenticated by STR profiling.

| Plasmid name | Reference |
| --- | --- |
| pMXS_FLAG-SFXN1co | This study |
| pMXS_SFXN1co | This study |
| pMXS_FLAG-SFXN2 | This study |
| pMXS_FLAG-SFXN3 | This study |
| pMXS_FLAG-SFXN4 | This study |
| pMXS_FLAG-SFXN5 | This study |
| pMXS_SFXN5 | This study |
| pMXS_FLAG-FSF1co | This study |
| pMXS_FLAG-CG11739co | This study |
| pMXS_FLAG-CG6812co | This study |

Cell Culture

Unless otherwise indicated, Jurkat, K562, and HEL cells were cultured in RPMI (Life Technologies) supplemented with 10% Inactivated Fetal Calf Serum (IFS, Sigma), 2 mM glutamine, and penicillin/streptomycin. HeLa and 293T cells were cultured in DMEM (Life Technologies) supplemented with 10% IFS and penicillin/streptomycin. 293T cells used for virus production were cultured in IMDM (Life Technologies) supplemented with 20% IFS, and penicillin/streptomycin. To prepare media lacking serine or glycine, RPMI without amino acids and glucose (US Biological) was supplemented with amino acids except serine and glycine and 11 mM glucose according to the RPMI 1640 formulation (Life Technologies) with the addition of 130 µM alanine (except in CRISPR screens) as well as dialyzed IFS and penicillin/streptomycin. Serine or glycine, or both amino acids (for control media) were added to the media in experiments as indicated.

Virus Production

HEK-293T cells were co-transfected with the pLentiCRISPR sgRNA library, the VSV-G envelope plasmid and the AVPR lentiviral packaging plasmid, or with pMXS plasmids and retroviral packaging plasmids Gag-Pol and VSV-G, using XTremeGene 9 Transfection Reagent (Roche). Culture medium was exchanged 24 hours after transfection with the same medium instead supplemented with 30% IFS. The virus-containing supernatant was collected 48 hours after transfection and spun for 5 min at 400×g to eliminate cells.

Transduction of Cell Lines

Cells were pelleted, then seeded at a density of 1,000,000 cells/mL in 6-well plates in 2 mL of RPMI containing 8 µg/mL polybrene (EMD Millipore), and then transduced with lentivirus by centrifugation at 2,200 RPM for 45 min at 37° C. After an 18-hour incubation, cells were pelleted to remove virus, washed twice in PBS and then re-seeded into fresh culture medium containing puromycin or blasticidin, and selected for 72 hours.

Generation of CRISPR/Cas Knockout Cells

Human SFXN1, SFXN2, SHMT1, SHMT2, MTHFD2 were depleted using the lentiviral pLentiCRISPRv1 system. The following sense (S) and antisense (AS) oligonucleotides were cloned into pLentiCRISPRv1:

sgSFXN1_1 (S): caccgGAAATACTGCTCGTGCGCAG (SEQ ID NO: 1)

sgSFXN1_1 (AS): aaacCTGCGCACGAGCAGTATTTCc (SEQ ID NO: 2)

sgSFXN1_2 (S): caccgGATATGGAGCCAGGGGCCGG (SEQ ID NO: 3)

sgSFXN1_2 (AS): aaacCCGGCCCCTGGCTCCATATC (SEQ ID NO: 4)

sgSFXN2_1 (S): caccgGATATGGAGCCAGGGGCCGG (SEQ ID NO: 5)

sgSFXN2_1 (AS): aaacCCGGCCCCTGGCTCCATATC (SEQ ID NO: 6)

sgSHMT1_1 (S): caccgGATATGGAGCCAGGGGCCGG (SEQ ID NO: 7)

sgSHMT1_1 (AS): aaacCCGGCCCCTGGCTCCATATC (SEQ ID NO: 8)

sgSHMT2_1 (S): caccgGATATGGAGCCAGGGGCCGG (SEQ ID NO: 9)

sgSHMT2_1 (AS): aaacCCGGCCCCTGGCTCCATATC (SEQ ID NO: 10)

sgMTHFD2_1 (S): caccgGATATGGAGCCAGGGGCCGG (SEQ ID NO: 11)

sgMTHFD2_1 (AS): aaacCCGGCCCCTGGCTCCATATC (SEQ ID NO: 12)

SFXN3 was depleted using pX330 with the following guide:

sgSFXN3_1 (S): caccgGAGTGCCACCACTGGAGCTG (SEQ ID NO: 13)

sgSFXN3_1 (AS): aaacCAGCTCCAGTGGTGGCACTCc (SEQ ID NO: 14)

Control cells were generated by targeting the AAVS1 locus as described before (32).

CRISPR/Cas Negative Selection Screens

Cells were infected with a sgRNA library targeting 3000 metabolic genes and transporters (21). 48 hours after infection cells were selected with puromycin for 72 hours. After 48 hours of recovery post-selection, cells were seeded into RPMI with or without serine or glycine as indicated. Cells were passaged every other day, with seeding densities of 250,000 cells/ml for Jurkat cells and 175,000 cells/ml for K562 cells until reaching ~14-15 population doublings (PDs) in full media and glycine-deficient media or ~9 population doublings in serine-deficient media. WT and SFXN1-null cells in the SFXN1 synthetic lethality screen grown in glycine-deficient media were resuspended in fresh media lacking glycine every day from PD ~8 to the end of the screen to prevent accumulation of secreted glycine. DNA was extracted from 30-50 million cells using the QIAamp DNA Blood Maxi Kit (QIAGEN). sgRNA inserts were PCR amplified using Ex Taq DNA Polymerase (Takara). The resultant PCR products were purified and sequenced on a HiSeq 2500 (Illumina) (primer sequences provided below) to monitor the change in the abundance of each sgRNA between the initial and final cell populations.

Primer Sequences for sgRNA Quantification
Forward:
AATGATACGGCGACCACCGAGATCTACACGAA-TACTGCCATTTGTC TCAAGATCTA (SEQ ID NO: 15)
Reverse:
CAAGCAGAAGACGGCAT-ACGAGATCnnnnnnTTTCTTGGGTAGTTTG CAGTTTT (nnnnnn denotes the sample barcode) (SEQ ID NO: 16).
Illumina Sequencing Primer:
CGGTGCCACTTTTTCAAGTTGATAACGGACTA-GCCTTATTTTAACTT GCTATTTCTAGCTCTAAAAC (SEQ ID NO: 17)
Illumina Indexing Primer:
TTTCAAGTTACGGTAAGCATATGATAGTCCATTT-TAAAACATAATTT TAAAACTGCAAACTACCCAA-GAAA (SEQ ID NO: 18)

Sequencing reads were aligned to the sgRNA library and the abundance of each sgRNA was calculated. sgRNAs with less than 30 counts in the cell pool were removed from downstream analyses. The $\log_2$ fold-change in abundance of each sgRNA was calculated for each treatment condition after adding a pseudocount of one. Gene-based CRISPR Scores (gene scores) were defined as the average $\log_2$ fold-change in the abundance of all sgRNAs targeting a given gene between the initial and final cell populations and calculated for all treatment conditions. For the SFXN1-synthetic lethality screen the data was Z-score normalized. The differential gene score was calculated as the difference in CRISPR scores (gene scores) between treatment conditions.

Proliferation Assays 10,000 cells per well were seeded into 96 well plates in triplicate. Cell titer glo reagent (Promega) was added to one plate immediately after seeding and luminescence was measured, while a second plate was read-out 4 days after seeding. Number of doublings in 4 days was determined by calculating the $\log_2$ fold-change in signal between day 0 and 4. For formate rescue experiments, 1 mM formate was added to cells at time of seeding (Jurkat cells) or cells were cultured in formate-containing media for 1 week prior to the experiment (K562 cells) unless indicated otherwise.

MS-Based Metabolomics and Quantification of Metabolite Abundance

Quantification of metabolite abundance using LC/MS-based metabolomics was performed and analyzed as previously described. Briefly, Jurkat or K562 cells were seeded at densities of $0.6 \times 10^6$ per ml and $0.33 \times 10^6$ per ml, respectively. 24 h later, $2 \times 10^6$ Jurkat or $1 \times 10^6$ K562 cells were harvested, washed once in ice-cold 0.9% saline prepared with LC-MS grade $H_2O$, and extracted with 80% methanol containing 500 nM isotope-labeled amino acids as internal standards (Cambridge Isotope Laboratories). The samples were vortexed for 10 min at 4° C. and spun down at 17,000×g. The supernatant was dried by vacuum centrifugation at 4° C. Samples were stored at −80° C. until analyzed. On the day of analysis, samples were resuspended in 50-100 μL of LC/MS grade water and the insoluble fraction was cleared by centrifugation at 15,000 rpm. The supernatant was then analyzed as previously described by LC/MS (21, 33).

Amino acids were normalized to their respective internal standards, purine synthesis intermediates were normalized to the glutamate internal standard. Folate measurements were performed as previously described (34). For GC/MS analysis of amino acids, samples were prepared as for LC-MS analysis, but after drying the samples were derivatized using N-tert-Butyldimethylsilyl-N-methyltrifluoroacetamide (Sigma-Aldrich) as previously described (12).

Serine Tracing Experiments

Cells were cultured for 12 hours in serine deficient RPMI containing 285 μM 2,3,3-$^2H_3$-serine (Cambridge Isotope Laboratories), supplemented with 10% dialyzed serum. Cells were extracted for LC/MS metabolite analysis as described above. For LCMS analysis of labeled nucleotides, dried samples were resuspended in 40 μL LCMS grade water and 10 μL were injected. Mass isotopomer distributions were corrected for natural abundance using in-house algorithms as previously described (12).

In parallel, culture supernatant was collected and after removal of cells by centrifugation, 20 μL were extracted for GC/MS analysis with 300 μL acetone containing 1 μg norvaline. Samples were vortexed briefly and spun 10 min at 4° C. 200 μl of the supernatant were dried down using a nitrogen dryer and derivatized and analyzed as described above. Mass isotopomer distributions were determined by integrating metabolite ion fragments and corrected for natural abundance using in-house algorithms as previously described (12). Glycine levels were normalized to norvaline.

Immunofluorescence Assays

For immunofluorescence assays 50,000 HeLa cells were plated in a 24 well glass bottom imaging plate (Cellvis, Mountain View, Calif.) and transfected with 500 ng of the cDNAs for FLAG-Sideroflexin constructs 16 hours later. 48 hours after transfection, cells were rinsed twice with PBS and fixed with 3% paraformaldehyde with 0.1% glutaraldehyde in PBS for 10 minutes at room temperature. The slides were then rinsed three times with PBS and the cells permeabilized with 0.3% NP40, 0.05% Triton X-100, 0.1% BSA in PBS for 3 minutes at room temperature. The slides were rinsed three times with wash buffer (0.05% NP40, 0.05% Triton-X 100, 0.2% BSA in PBS) and then blocked for 1 hour in blocking buffer (0.05% NP40, 0.05% Triton-X 100, 5% Normal Donkey Serum) at room temperature. The slides were incubated with primary antibody in blocking buffer for 1 hour at room temperature, washed three times with wash buffer, and incubated with secondary antibodies produced in donkey (diluted 1:500 in blocking buffer) for 30 minutes at room temperature in the dark, washed three times with wash buffer, and rinsed three times with PBS.

The primary antibodies used were directed against COX4 (CST; 1:250 dilution) and FLAG epitope (Sigma, 1:1000 dilution). Images were acquired on a Zeiss AxioVert200M microscope with a 63× oil immersion objective and a Yokogawa CSU-22 spinning disk confocal head with a *Borealis* modification (Spectral Applied Research/Andor) and a Hamamatsu ORCA-ER CCD camera. The MetaMorph software package (Molecular Devices) was used to control the hardware and image acquisition. The excitation lasers used to capture the images were 488 nm and 647 nm. Images were process with FIJI (35).

Mitochondrial Isolation for Western Blot

30Mio Jurkat or K562 cells were washed 1× in PBS, 1× in KPBS according to (33). 5 ul of the cell suspension in 1 ml KPBS was lyzed in 50 ul of 1% Triton lysis buffer to obtain whole cell protein levels. The rest was lyzed using 8 or 5 strokes for Jurkat and K562 cells respectively with a 301/2 G needle. Lysates were spun for 1 min at 1000×g to pellet unbroken cells, and subsequently incubated with 100 ul HA-magnetic beads for 4 min. Beads were washed 3× in KPBS, and mitochondria lyzed in 50 ul lysis buffer for 10 min. Beads were removed using the magnet, and samples were spun 10 min at 17,000×g to remove residual beads and insoluble material. SDS-PAGE loading dye was added to each sample, and for Jurkat cells 6 µl of whole cell lysate and 9 µl of the mitochondrial fraction were run on a gel, for K562 cells 12 µl of each whole cell lysate and mitochondrial fraction and for HeLa cells 8 µl each.

In Vitro Serine Transport Assays

In vitro transport assays were performed as described previously with the following specifications. Flag-SFXN1 was purified from 293T cells stably expressing the protein using FLAG-affinity purification and eluted off beads with FLAG peptide.

1% Phosphatidylcholine was added to total *E. coli* lipids in chloroform, evaporated under nitrogen and desiccated overnight. Dried lipids were hydrated in inside buffer (20 mM MES pH 7, 50 mM NaCl, 20 mM KCl) by freeze-thawing in liquid nitrogen 20× times. Lipids were extruded 6× though a 0.4 µm filter and 15× through a 0.1 µm filter. 15 ug of purified SFXN1 protein were reconstituted into 1.2 mg liposomes using a detergent:lipid ratio of 5:1 with the addition of 1 mM DTT in inside buffer rotating at 4 degree for 1 hour. The proteoliposomes were incubated for 3 sequential rounds with Bio-beads to remove detergent. A liposome-only control was prepared by replacing the protein with inside buffer in the reconstitution reaction. Incorporation of protein into liposomes was assessed using glycerol gradient centrifugation. A buffer containing 20 mM Tris-HCL pH 7.4 and 100 mM NaCl was used as outside buffer in transport reactions.

Bioinformatics Analysis

SFXN1 topolgy was predicted using Protter (36). For construction of the phylogenetic tree, Sideroflexin homolog protein sequences (SFXN1_HUMAN Q9H9B4, SFXN2_HUMAN Q96NB2, SFXN3_HUMAN Q9BWM7, SFXN4_HUMAN Q6P4A7, SFXN5_HUMAN Q8TD22, FSF1_YEAST Q12029, Q9VN13_DROME, Q9VVW3_DROME) were aligned using MUSCLE (37). PHYLIP's proml (38) was used to construct the phylogenetic tree and FigTree software v. 1.4.3 to visualize it. Graphpad Prism 7 software was used to generate the heat map of Sideroflexin RNA expression based on data from the Cancer Cell Line Encyclopedia.

Statistical Analyses

Two-tailed t tests were used for comparison between two groups. All comparisons were two-sided, and P values of less than 0.05 were considered to indicate statistical significance. All error bars denote standard deviation.

REFERENCES

1. D. R. Appling, Compartmentation of folate-mediated one-carbon metabolism in eukaryotes. *FASEB J* 5, 2645-2651 (1991).
2. A. S. Tibbetts, D. R. Appling, Compartmentalization of Mammalian folate-mediated one-carbon metabolism. *Annu Rev Nutr* 30, 57-81 (2010).
3. C. K. Barlowe, D. R. Appling, In vitro evidence for the involvement of mitochondrial folate metabolism in the supply of cytoplasmic one-carbon units. *Biofactors* 1, 171-176 (1988).
4. R. K. Hampson, L. L. Barron, M. S. Olson, Regulation of the glycine cleavage system in isolated rat liver mitochondria. *J Biol Chem* 258, 2993-2999 (1983).
5. W. Pfendner, L. I. Pizer, The metabolism of serine and glycine in mutant lines of Chinese hamster ovary cells. *Arch Biochem Biophys* 200, 503-512 (1980).
6. M. R. Narkewicz, S. D. Sauls, S. S. Tjoa, C. Teng, P. V. Fennessey, Evidence for intracellular partitioning of serine and glycine metabolism in Chinese hamster ovary cells. *Biochem J* 313, 991-996 (1996).
7. H. Patel, E. D. Pietro, R. E. MacKenzie, Mammalian fibroblasts lacking mitochondrial NAD+-dependent methylenetetrahydrofolate dehydrogenase-cyclohydrolase are glycine auxotrophs. *J Biol Chem* 278, 19436-19441 (2003).
8. G. Kikuchi, The glycine cleavage system: composition, reaction mechanism, and physiological significance. *Mol Cell Biochem* 1, 169-187 (1973).
9. T. Yoshida, G. Kikuchi, Major pathways of glycine and serine catabolism in rat liver. *Arch Biochem Biophys* 139, 380-392 (1970).
10. G. S. Ducker et al., Reversal of Cytosolic One-Carbon Flux Compensates for Loss of the Mitochondrial Folate Pathway. *Cell Metab* 23, 1140-1153 (2016).
11. X. R. Bao et al., Mitochondrial dysfunction remodels one-carbon metabolism in human cells. *Elife* 5, (2016).
12. C. A. Lewis et al., Tracing compartmentalized NADPH metabolism in the cytosol and mitochondria of mammalian cells. *Mol Cell* 55, 253-263 (2014).
13. R. Nilsson et al., Metabolic enzyme expression highlights a key role for MTHFD2 and the mitochondrial folate pathway in cancer. *Nat Commun* 5, 3128 (2014).
14. F. Liu et al., Increased MTHFD2 expression is associated with poor prognosis in breast cancer. *Tumour Biol* 35, 8685-8690 (2014).
15. Y. Pikman et al., Targeting MTHFD2 in acute myeloid leukemia. *J Exp Med* 213, 1285-1306 (2016).
16. A. M. Hosios et al., Amino Acids Rather than Glucose Account for the Majority of Cell Mass in Proliferating Mammalian Cells. *Developmental Cell* 36, 540-549 (2016).
17. J. Benavides, M. L. Garcia, J. Lopez-Lahoya, M. Ugarte, F. Valdivieso, Glycine transport in rat brain and liver mitochondria. *Biochim Biophys Acta* 598, 588-594 (1980).
18. C. Yu, D. L. Claybrook, A. H. Huang, Transport of glycine, serine, and proline into spinach leaf mitochondria. *Arch Biochem Biophys* 227, 180-187 (1983).
19. R. L. Cybulski, R. R. Fisher, Swelling of mitochondria in response to L-isomers of serine, alanine, methionine, valine, threonine, leucine, proline, glycine. *Biochemistry* 16, 5116-5512 (1977).
20. R. L. Cybulski, R. R. Fisher, Intramitochondrial localization and proposed metabolic significance of serine transhydroxymethylase. *Biochemistry* 15, 3183-3187 (1976).
21. K. Birsoy, Wang, T., Chen, W. W., Freinkman, E., Abu-Remaileh, M., Sabatini, D. M., An Essential Role of the Mitochondrial Electron Transport Chain in Cell Proliferation Is to Enable Aspartate Synthesis. *Cell* 162, 540-551 (2015).
22. M. D. Fleming, D. R. Campagna, J. N. Haslett, C. C. Trenor, N. C. Andrews, A mutation in a mitochondrial transmembrane protein is responsible for the pleiotropic hematological and skeletal phenotype of flexed-tail (f/f) mice. *Genes Dev* 15, 652-657 (2001).
23. S. Y. Lee et al., APEX Fingerprinting Reveals the Subcellular Localization of Proteins of Interest. *Cell Rep* 15, 1837-1847 (2016).
24. F. T. Kao, T. Puck, Mutagenesis and genetic analysis with Chinese hamster auxotrophic cellmarkers. *Genetics* 79, 343-352 (1975).
25. M. W. McBurney, G. F. Whitmore, Isolation and biochemical characterization of folate deficient mutants of Chinese hamster cells. *Cell* 2, 173-182 (1974).
26. D. L. Guernsey et al., Mutations in mitochondrial carrier family gene SLC25A38 cause nonsyndromic autosomal recessive congenital sideroblastic anemia. *Nat Genet* 41, 651-653 (2009).
27. P. Lunetti et al., Characterization of Human and Yeast Mitochondrial Glycine Carriers with Implications for Heme Biosynthesis and Anemia. *J Biol Chem* 291, 19746-19759 (2016).
28. G. J. Hildick-Smith et al., Macrocytic anemia and mitochondriopathy resulting from a defect in sideroflexin 4. *Am J Hum Genet* 93, 906-914 (2013).
29. C. F. Labuschagne, N. J. van den Broek, G. M. Mackay, K. H. Vousden, O. D. Maddocks, Serine, but not glycine, supports one-carbon metabolism and proliferation of cancer cells. *Cell Rep* 7, 1248-1258 (2014).
30. J. Ye et al., Serine catabolism regulates mitochondrial redox control during hypoxia. *Cancer Discov* 4, 1406-1417 (2014).
31. D. Kim et al., SHMT2 drives glioma cell survival in ischaemia but imposes a dependence on glycine clearance. *Nature* 520, 363-367 (2015).
32. T. Wang et al., Identification and characterization of essential genes in the human genome. *Science* 350, 1096-1101 (2015).
33. W. W. Chen, E. Freinkman, T. Wang, K. Birsoy, D. M. Sabatini, Absolute Quantification of Matrix Metabolites Reveals the Dynamics of Mitochondrial Metabolism. *Cell* 166, 1324-1337 e1311 (2016).
34. N. Kanarek, Histidine catabolism is a major determinant of methotrexate sensitivity. *Nature*, (2018).
35. J. Schindelin et al., Fiji: an open-source platform for biological-image analysis. *Nat Methods* 9, 676-682 (2012).
36. U. Omasits, C. H. Ahrens, S. Muller, B. Wollscheid, Protter: interactive protein feature visualization and integration with experimental proteomic data. *Bioinformatics* 30, 884-886 (2014).
37. R. C. Edgar, MUSCLE: multiple sequence alignment with high accuracy and high throughput. *Nucleic Acids Res* 32, 1792-1797 (2004).
38. J. Felsenstein, PHYLIP—Phylogeny Inference Package (Version 3.2). *Cladistics* 5, 164-166 (1989).

Example 2

This Example both re-presents certain data from Example 1 and provides additional data.

One carbon metabolism uses serine to generate the reactive one-carbon donors, such as 5,10-methylene-tetrahydrofolate, required for many basic processes, including nucleotide and lipid synthesis (recently reviewed in (1-3)). An interesting aspect of the one-carbon pathway is that while partially redundant isozymes exist in the cytosol and mitochondrial matrix, in most proliferating cells the pathway primarily flows from the cytosol into mitochondria and back out (FIG. 1A). Cytosolic serine enters the mitochondrial matrix and is converted to glycine and formate, which then exits to the cytosol where it is used to generate the charged folates that serve as one-carbon donors ((4); FIG. 1A). In dividing mammalian cells the mitochondrial catabolism of serine supplies the majority of the one-carbon units needed for biosynthesis (5-9), but the cytosolic branch can compensate for its loss (8).

Given that the entry of serine into mitochondria is a critical step in the generation of one-carbon units, it is surprising that the mitochondrial transporter(s) for serine remains unknown (5, 10-12). To seek such a transporter a CRISPR-Cas9-mediated genetic screen was designed based on the likelihood that loss of mitochondrial serine transport will reduce the proliferation of cells lacking the cytosolic branch of one-carbon metabolism. Moreover, it was reasoned that even if there are redundant mechanisms for serine transport cells can be sensitized to its partial inhibition by lowering cytosolic serine concentrations, which is easily achieved by removing exogenous serine (FIG. 5D) (13). Thus, we sought genes required for the optimal proliferation of cells lacking the cytosolic one-carbon pathway when cultured in serine-free media.

A Genetic Screen for Components of the Mitochondrial One-Carbon Metabolism Pathway Yields SFXN1

To implement such a screening strategy human Jurkat leukemic T-cells and K562 erythroleukemic cells null for serine hydroxymethyltransferase 1 (SHMT1) were generated, an isozyme of mitochondrial SHMT2 and a key component of the cytosolic one-carbon pathway that interconverts serine and glycine (FIG. 1A). Jurkat and K562 cells were chosen because they are suitable for screening (14, 15) and have high mitochondrial one-carbon pathway activity (8, 16). The SHMT1-null cells were transduced with a lentiviral sgRNA library that targets ~3,000 metabolic enzymes, small molecule transporters, and metabolism-related transcription factors (~10 sgRNAs/gene) and also contains 500 control sgRNAs (15). The transduced cells were cultured in RPMI media with or without serine and for each gene a gene score was generated by calculating the mean log 2 fold-change in the abundance from the beginning to end of the culture period of all the sgRNAs targeting the gene (15) (FIG. 1B). A differential gene score was also obtained that reflects the relative importance of the gene in the presence or absence of serine.

Figure 5A:
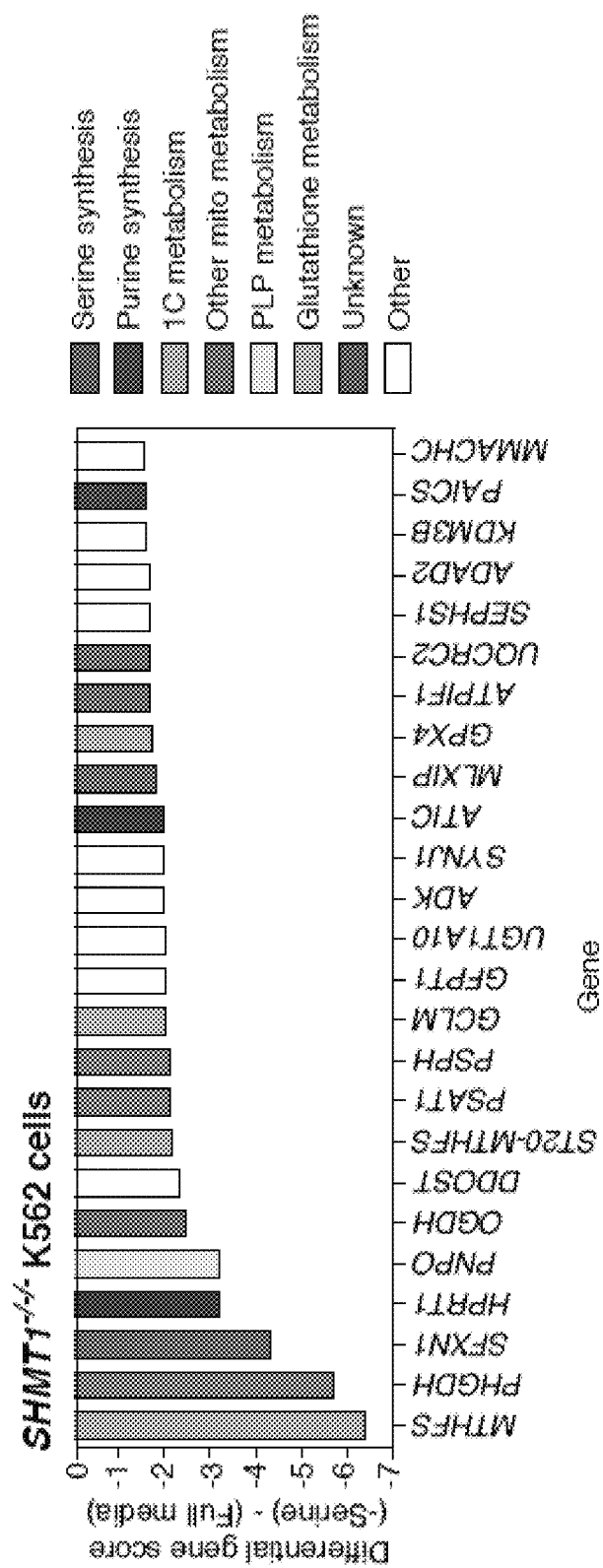
FIGS. 5A-5D demonstrate CRISPR/Cas9 screens identify SFXN1 to be required for growth in the absence of serine.
Figure 5B:
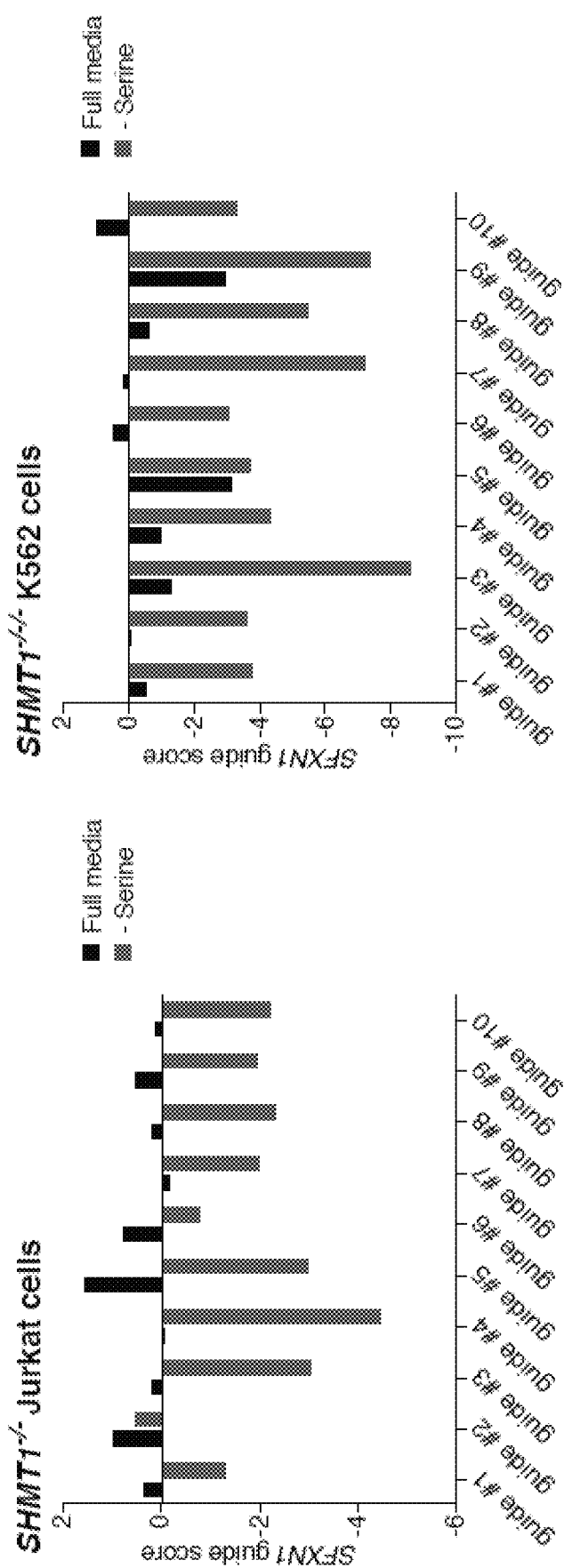

As expected, most genes, as well as the control sgRNAs, had similar scores in cells cultured under both media conditions (FIG. 1C). Multiple classes of genes behaved as predicted. For example, in both cell lines the three genes in the serine synthesis pathway (PHGDH, PSAT1, PSPH) were required for proliferation in serine-free media, as were components of the purine synthesis pathway, which is downstream of one-carbon metabolism (FIG. 1D, FIG. 5A). Established components of the mitochondrial one-carbon pathway, such as SHMT2 and the mitochondrial folate transporter/carrier (MFT), scored differentially in Jurkat cells, as did 5,10-Methenyltetrahydrofolate synthetase (MTHFS), which returns 5-formyl-tetrahydrofolate to the tetrahydrofolate (THF) co-factor pool (17), in K562 cells.

Strikingly, the only gene of unknown molecular function that scored differentially in both cell lines was the mitochondrial transmembrane protein Sideroflexin 1 (SFXN1)

Figure 8A:
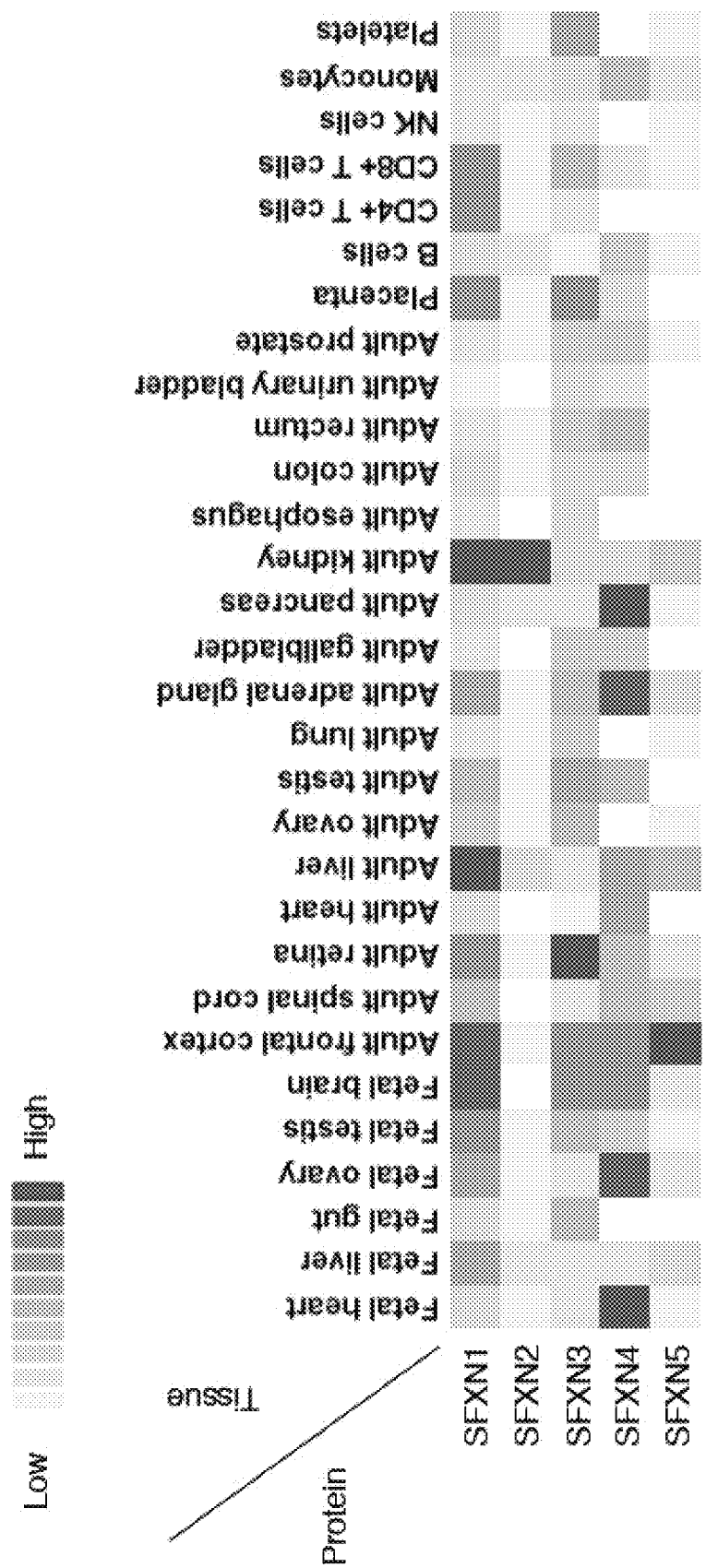
FIGS. 8A-8C demonstrates that there are multiple Sideroflexins and their expression varies across tissues.
Figure 8B:
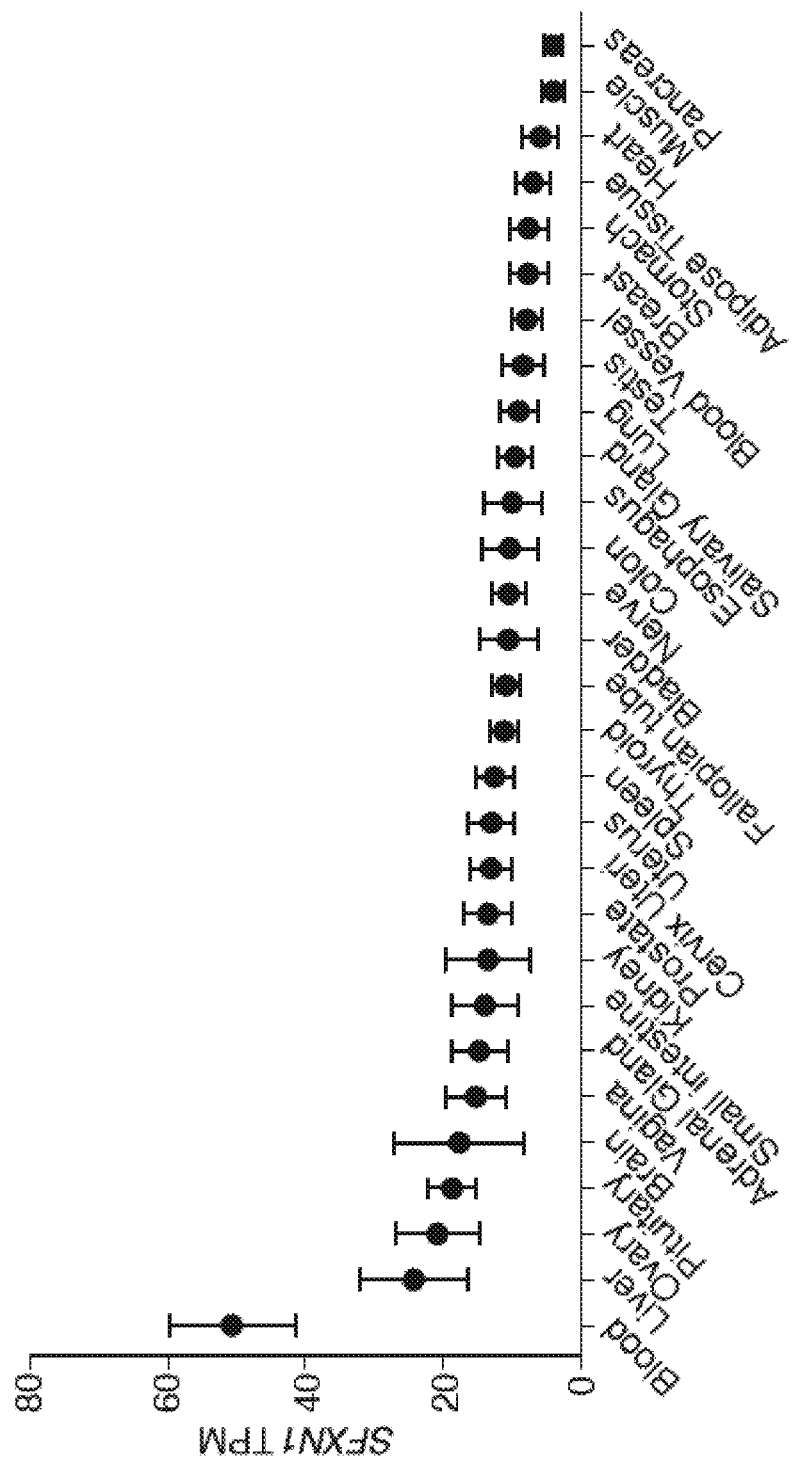

(FIGS. 1C-1D, FIGS. 5A-5B). Sfxn1 was originally identified as the gene mutated in a mouse mutant with anemia and axial skeletal abnormalities, and is part of the Sideroflexin family of proteins conserved throughout eukaryotes (18, 19). In humans, SFXN1 is highly expressed in the blood, liver, and kidney, which are tissues with high one-carbon metabolism activity (FIGS. 8A-8B).

Figure 5C:
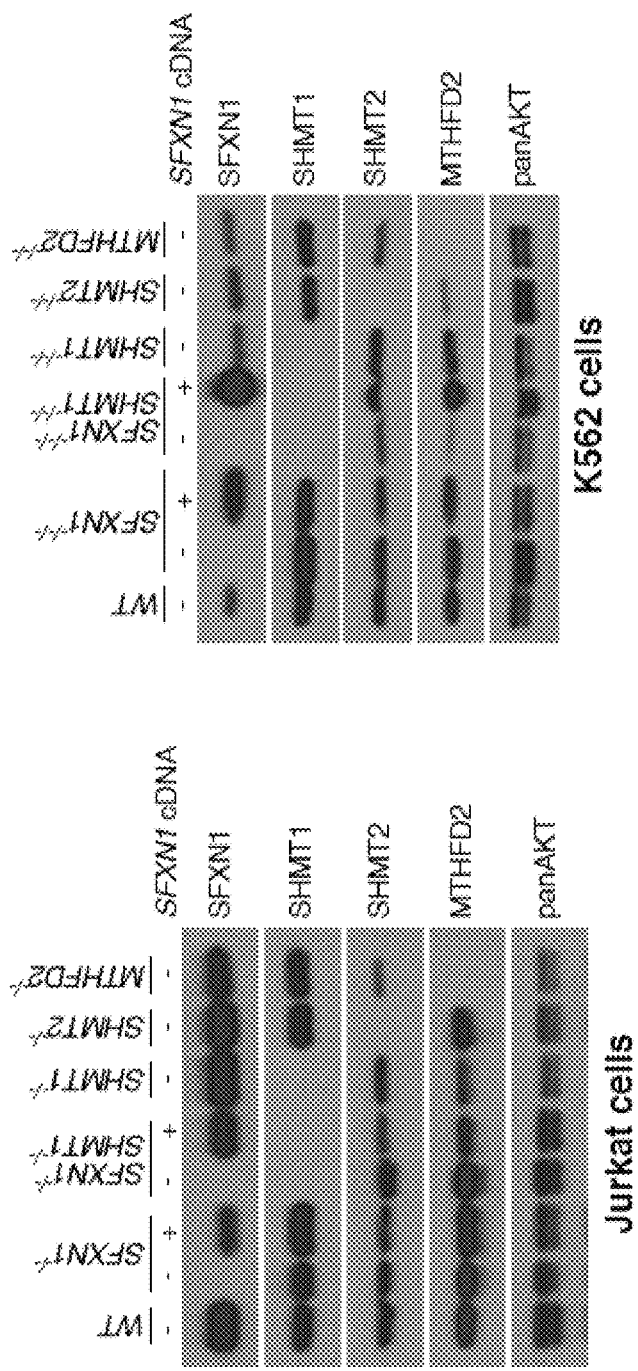
Figure 5D:
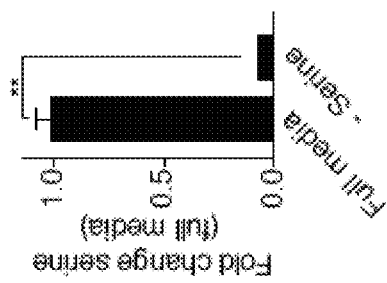

To follow up the screen, Jurkat and K562 cells were generated lacking SFXN1 alone or in combination with SHMT1 (FIG. 5C). In the absence of serine, the SFXN1-null Jurkat cells proliferated more slowly than the wild-type or AAVS1-targeted control cells and the loss of SHMT1 exacerbated the defect, consistent with the screening results (FIG. 1E). The SFXN1-null K562 cells proliferated less well than their Jurkat counterparts, but SHMT1 deletion did not exacerbate the defect, likely because K562 cells express very low levels of SHMT1 to begin with (FIG. 4C). The addition of formate, the product of the mitochondrial one-carbon pathway, completely reversed the slow proliferation of the Jurkat and K562 single- and double-null cells in the serine-free media, directly implicating an insufficient supply of one-carbon units in their defective proliferation (FIG. 1E). Importantly, expression of an sgRNA-resistant SFXN1 cDNA restored the proliferation rate of the SFXN1-null cells to that of the wild-type cells (FIG. 1F). SHMT2-null cells exhibited similar albeit more profound proliferation defects than the cells lacking SFXN1 (FIG. 1E).

Loss of SFXN1 Phenocopies Mutants in Mitochondrial One-Carbon Metabolism

Figure 2M:
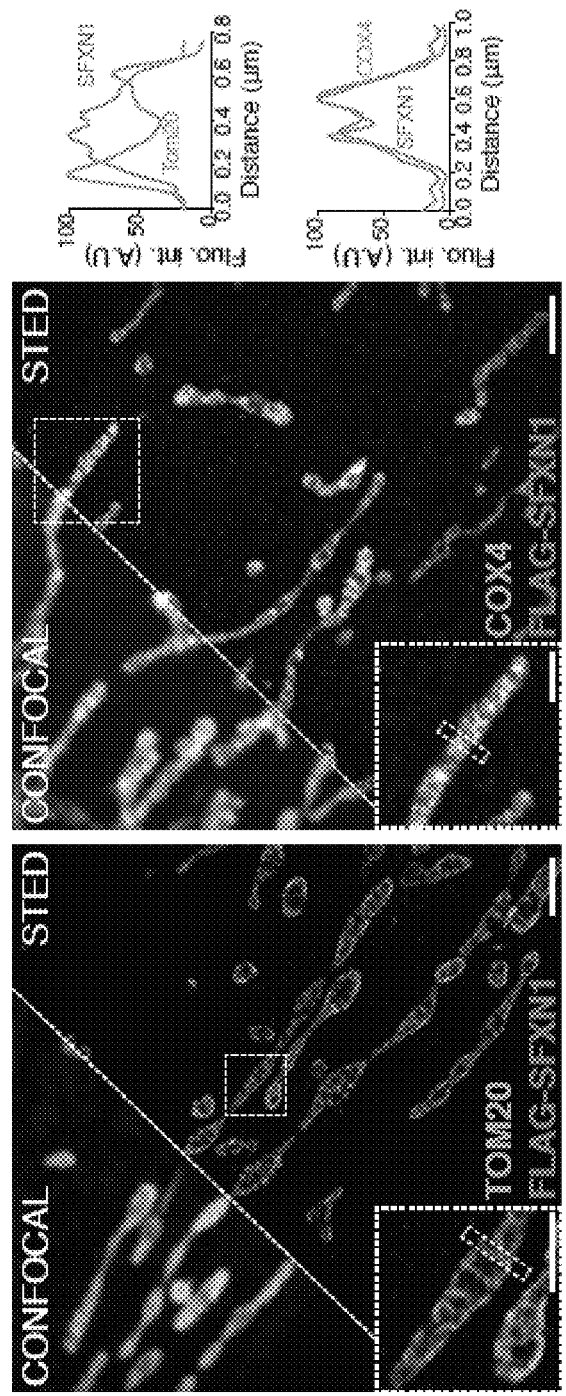
FIG. 2M shows super-resolution microscopy confirms SFXN1 localization to the inner membrane of mitochondria. Wild-type HeLa cells transiently expressing FLAG-SFXN1 were processed for immunofluorescence detection of the FLAG epitope (magenta) and the outer mitochondrial membrane marker Tom20 (left panel, green) or the mitochondrial inner membrane marker cytochrome c oxidase 4 (COX4) (right panel, green) and imaged by stimulated emission depletion (STED) microscopy. Overlap of magenta and green channels is shown in white and line profiles show fluorescent signals of each channel across mitochondria where marked by the dotted rectangles. Scale bars are 2 μm in the full images and 1 μm in the insets.

SFXN1 localizes to the inner mitochondrial membrane and is predicted to have five transmembrane domains ((18) and analysis with Protter) with its N-terminus in the matrix and C-terminus in the intermembrane space (FIG. 2A) (20). As expected, in HeLa cells Flag-tagged SFXN1 co-localized with the inner mitochondrial membrane protein COX4 (FIG. 2B), and endogenous SFXN1 was enriched in mitochondria purified from Jurkat and K562 cells (FIGS. 7A-7B). Using super-resolution microscopy it was confirmed that SFXN1 localizes to the inner and not outer mitochondrial membrane (FIG. 2M). The outer mitochondrial membrane, which can be marked by Tom20 (FIG. 2M), is permeable to most small metabolites due to the presence of the VDAC porins. Given these attributes and its emergence from the screen, SFXN1 was an excellent candidate to be a mitochondrial serine transporter.

Figures 6I, 6J:
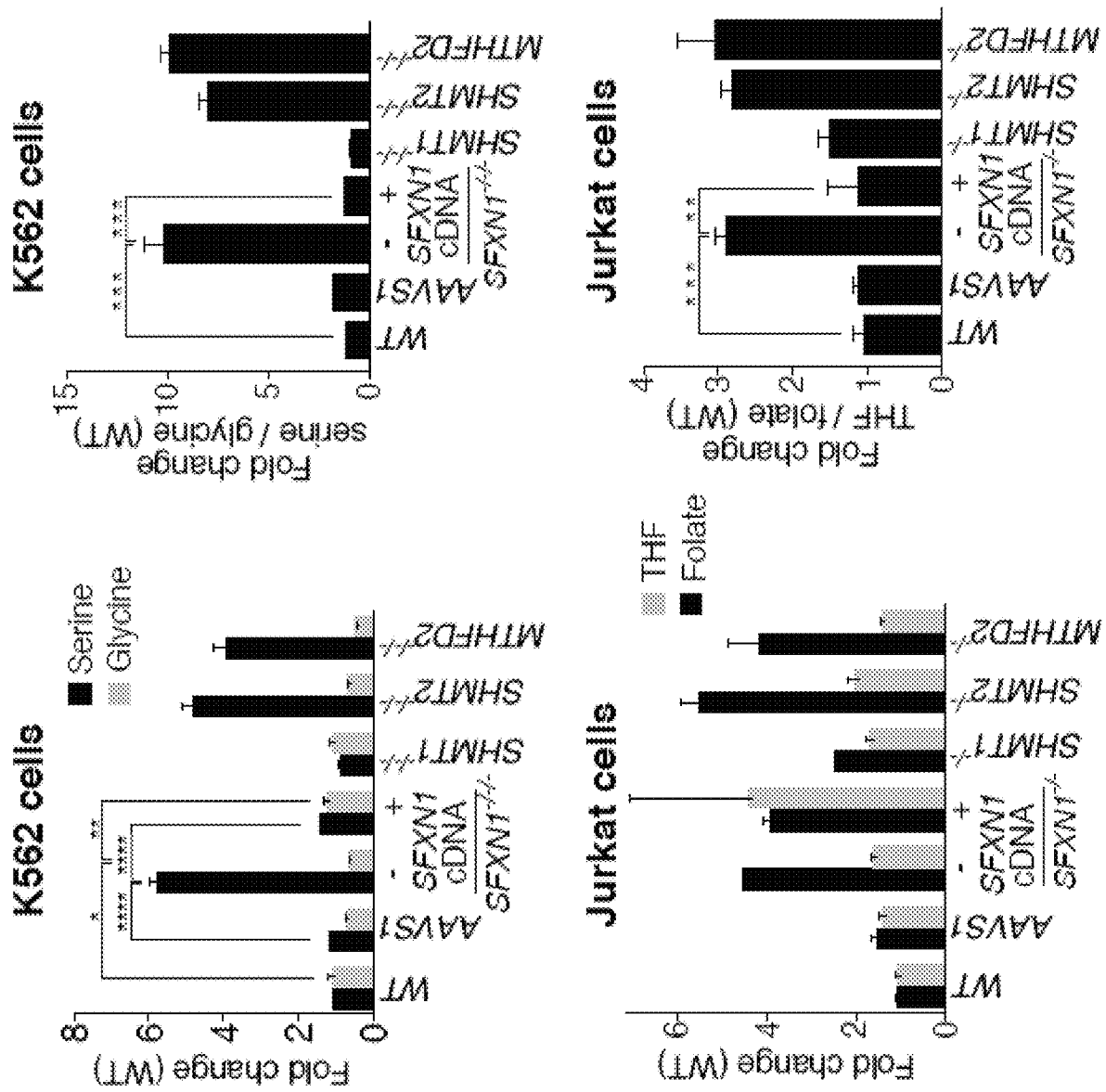

If this were the case, cells lacking SFXN1 should have similar metabolic defects as those missing SHMT2 or MTHFD2, the enzymes needed to convert serine to glycine and formate in mitochondria. Indeed, loss of SFXN1, SHMT2, or MTHFD2, but not SHMT1, caused the depletion of glycine in Jurkat cells, an increase in the serine to glycine ratio, and a reduction in the amount of de novo synthesized glycine secreted into the media as measured in tracing experiments with labeled serine (FIGS. 2N-2O and FIG. 6I). The null cells also had less of the charged folate species detected (5,10-methenyl-THF and 5-formyl-THF), and this was not secondary to a drop in THF or folate levels (FIG. 2P and FIG. 6J). The sgRNA-resistant SFXN1 cDNA complemented all the metabolic defects of the SFXN1-null cells.

Figures 2Q, 2R, 2S, 2T:
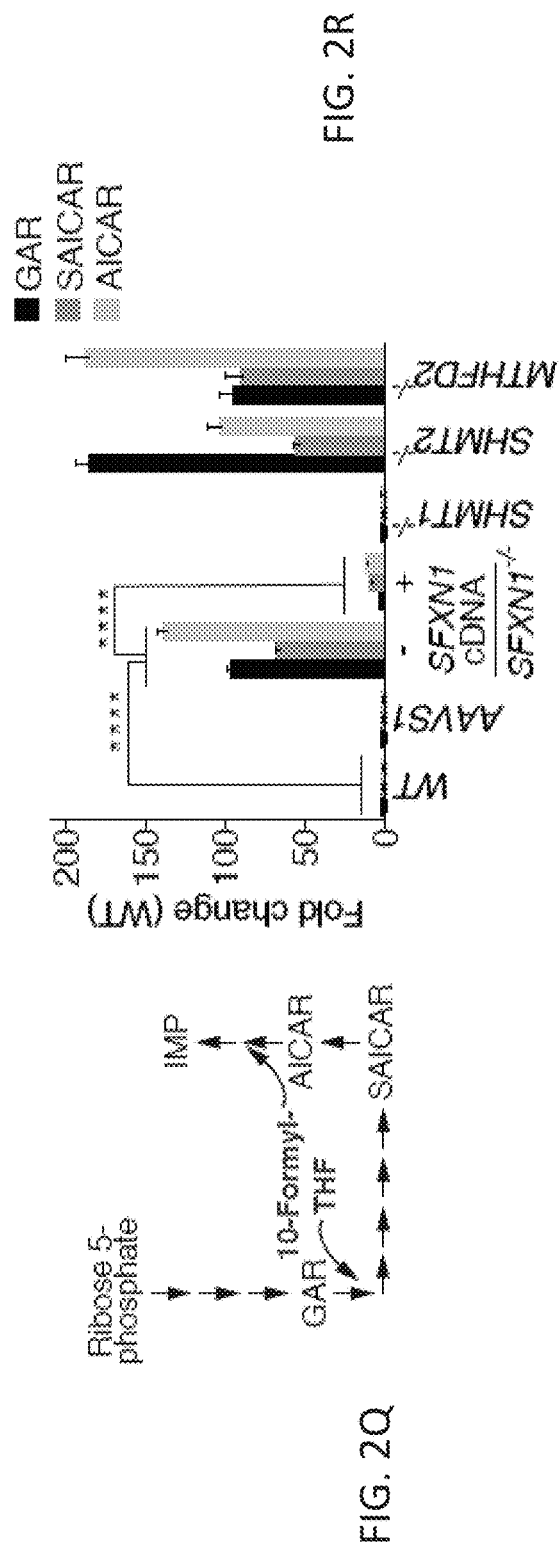
FIG. 2Q provides a schematic of the purine synthesis pathway indicating steps using one-carbon units in the form of 10-formyl-THF. GAR—5'-phosphoribosyl-glycinamide SAICAR—Phosphoribosylaminoimidazolesuccinocarboxamide AICAR—5-Aminoimidazole-4-carboxamide ribonucleotide. IMP—inosine monophosphate.
FIG. 2R shows the purine synthesis intermediates GAR, SAICAR, and AICAR accumulate in SFXN1-null cells. Purine synthesis intermediates were measured by LC-MS in extracts from wild-type Jurkat cells or single-cell-derived control and knockout clones (mean±SD; n=3; P<0.01, *P<0.001, **P<0.0001).
FIG. 2S shows addition of 1 mM formate does not rescue glycine levels and serine/glycine ratio of SFXN1-null cells. Serine and glycine levels were measured by LC-MS in extracts from wild-type Jurkat cells or single-cell-derived SFXN1-null cells incubated for 24 hours in the indicated media (mean±SD; n=3; *P<0.05, P<0.01).
Figure 6L:
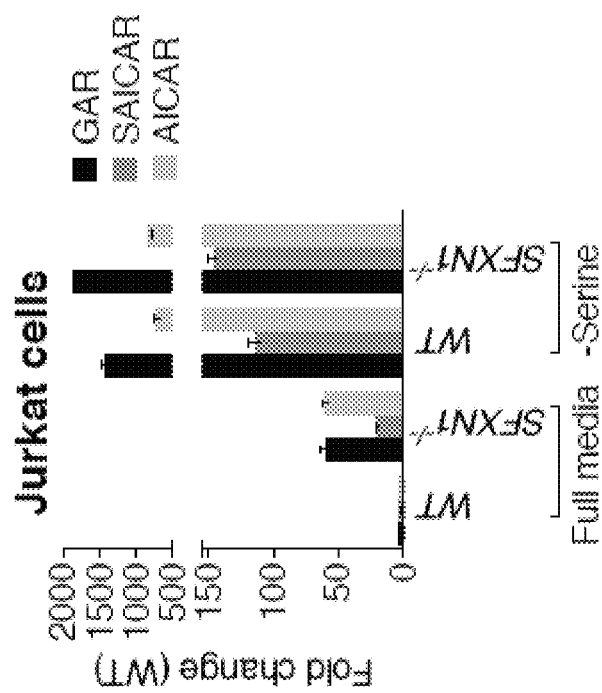
Figure 6K:
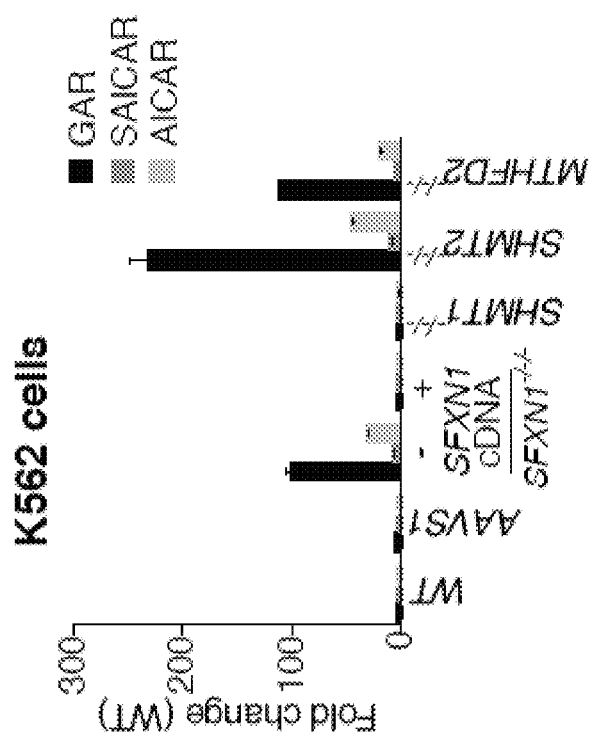

To determine if loss of SFXN1 impacts pathways that consume one-carbon donors purine synthesis was examined as it uses large amounts of 10-formyl-THF as a co-factor (FIG. 2Q). Indeed, the purine synthesis intermediates 5'-phosphoribosyl-glycinamide (GAR), phosphoribosylaminoimidazolesuccinocarboxamide (SAICAR), and 5-Amino-imidazole-4-carboxamide ribonucleotide (AICAR), accumulated in SFXN1-null cells to similar extents as in those lacking SHMT2 and MTHFD2 (8) (FIG. 2R and FIG. 6K). In this respect, loss of SFXN1 mimicked serine starvation, which in wild-type cells also caused an accumulation of the intermediates (FIG. 6L). Consistent with SFXN1 acting upstream of formate production, formate abolished the accumulation of the intermediates in the SFXN1-null cells but did not rescue the defects in glycine levels (FIGS. 2S-2T).

To monitor the relative contributions of the cytosolic and mitochondrial pathways to the synthesis of one-carbon units in SFXN1-null cells, a reported strategy to trace [2,3,3-2H3]-serine to thymidine triphosphate (TTP) was employed (8, 21). The deuterated serine will give rise to TTP shifted by two mass units (TTP M+2) when catabolized through the cytosolic pathway but only by one mass unit (TTP M+1) if via the mitochondrial pathway (FIG. 6F). In wild-type cells the M+1 form was the predominant species of newly synthesized TTP, as expected in cells generating most of their one-carbon donors through mitochondria. In contrast, in cells lacking SFXN1, SHMT2, or MTHFD2 the majority of the newly synthesized TTP was of the M+2 species (FIG. 2I), consistent with SFXN1 being important for the function of the mitochondrial one-carbon pathway.

Figure 6M:
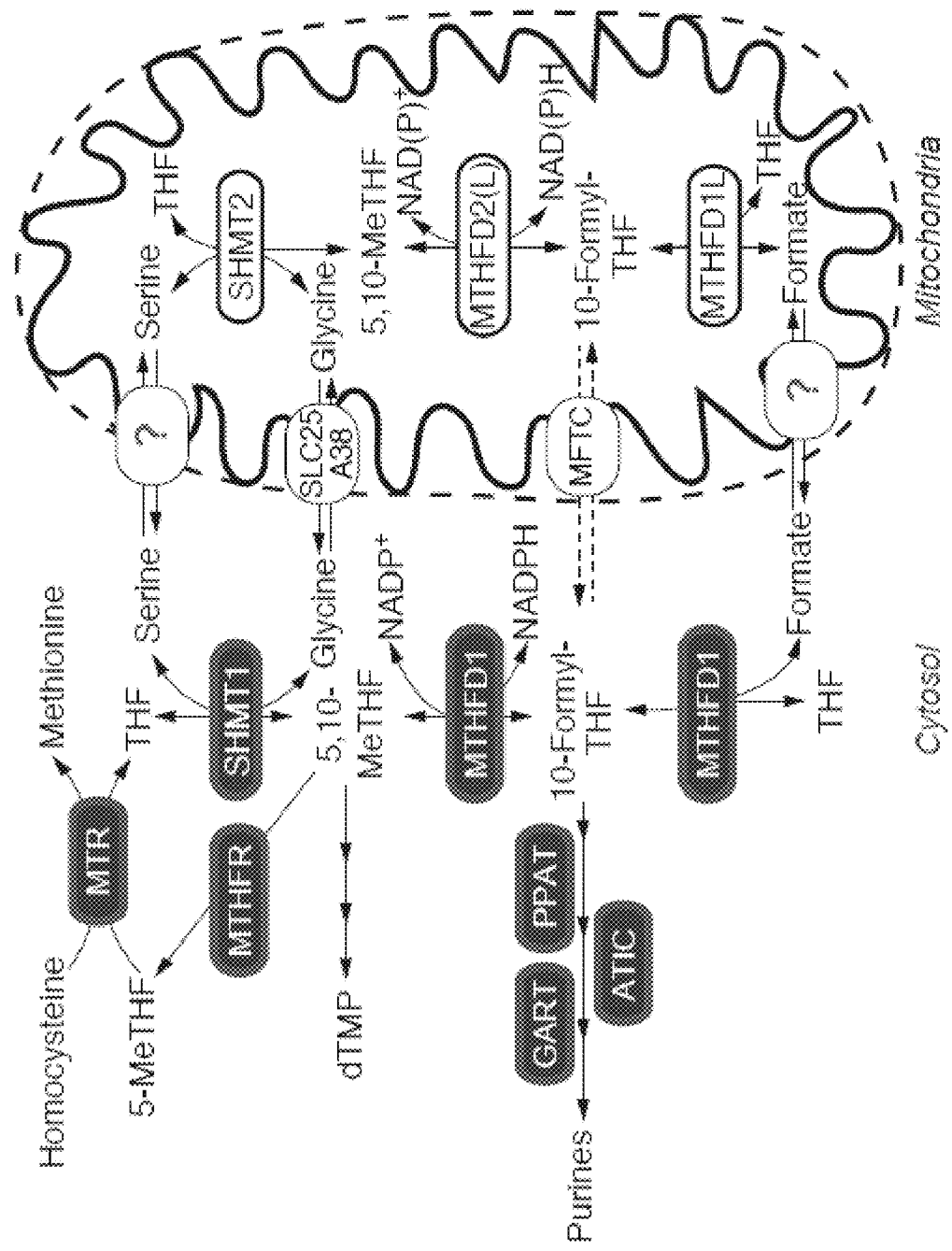

To corroborate this conclusion, a metabolism-focused sgRNA library was used to screen for genes important for the optimal proliferation of SFXN1-null but not wild-type cells. Gratifyingly, among the top hits were many components of the cytosolic one-carbon pathway, including SHMT1, which was the most differentially required gene (FIGS. 2K-2L and FIG. 6M). It was concluded that SFXN1 is part of the mitochondrial one-carbon pathway and its loss, like that of established components, makes cells more dependent on the cytosolic branch of the pathway.

SFXN1 Transports Serine In Vitro

To test if SFXN1 can directly transport serine, the FLAG-tagged protein from mammalian cells was purified (FIG. 9A) and reconstituted into liposomes. Recombinant SFXN1 mediated serine uptake into liposomes (FIG. 3A). Both L- and D-serine competed with the transport of the labelled serine, as did other amino acids, including the structurally related amino acids alanine, cysteine, and glycine while other metabolites did so to negligible extents (FIG. 3C). Neither formate nor citrate competed with serine transport. In vitro SFXN1 transports serine with a Km of ~170 µM (FIG. 3D), which suggests that SFXN1 can transport serine at the estimated cellular serine concentration of 300 µM. Consistent with these findings, serine uptake by mitochondria isolated from SFXN1-null cells was reduced compared to that by wild-type mitochondria, while the uptake of the structurally unrelated amino acid glutamate was unaffected (FIG. 3E).

Because alanine, cysteine, and glycine partially competed with serine in the in vitro transport assay, it was tested whether SFXN1 can also transport these amino acids. Indeed, SFXN1 transported alanine at the physiologically relevant concentration of 371 µM (FIG. 3F). Cysteine and glycine transport by SFXN1 was unable to be reliably measured, and it is suspected that further optimization of the assay might be necessary to determine whether SFXN1 can also directly transport these amino acids. To begin to assess a potential role for SFXN1 in the metabolism of these amino acids, cells were incubated in media with or without them. While the presence or absence of alanine or glycine did not impact the proliferation of SFXN1-null cells, they proliferated better than their wild-type counterparts in media with low concentrations of cystine, suggesting that SFXN1 may play a role in intracellular (e.g., mitochondrial) cysteine transport (FIG. 9C and FIG. 7H) (see Discussion).

Homologues of SFXN1 can Compensate for its Loss

Figure 7G:
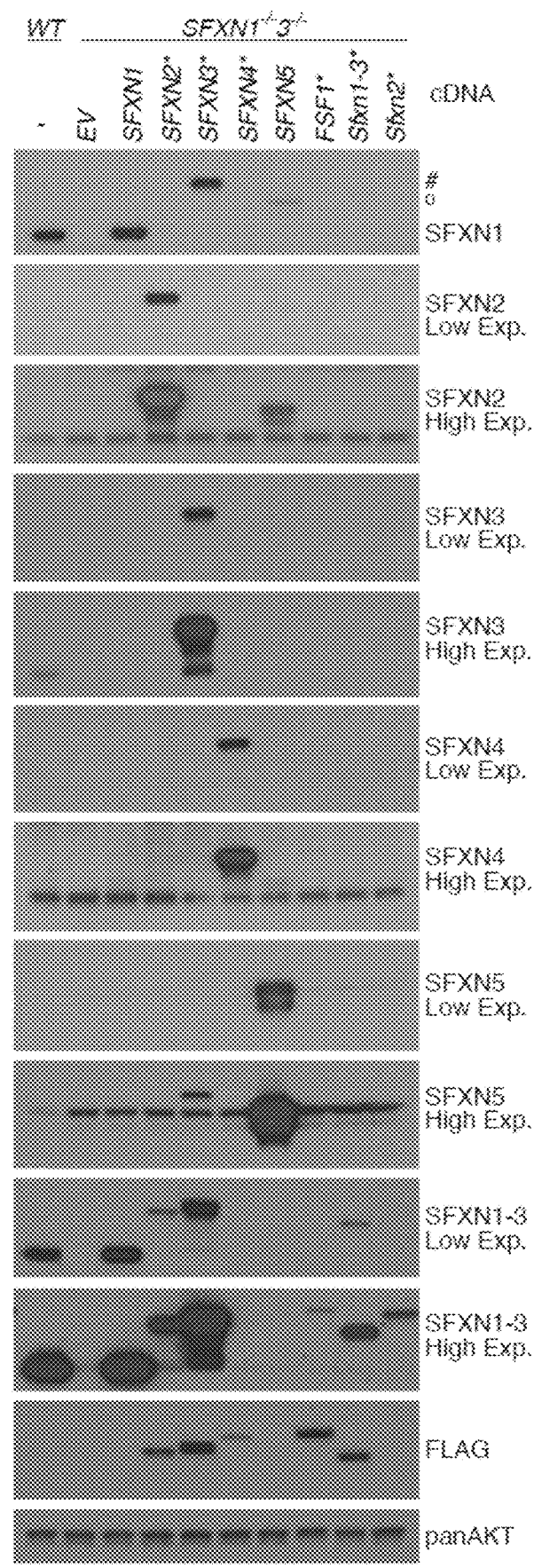
Figure 7H:
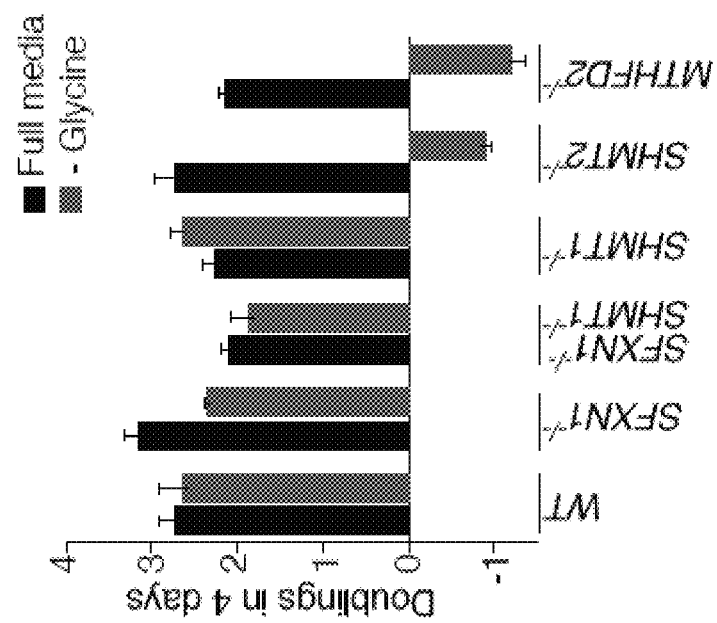
FIG. 7H shows loss of known components of the mitochondrial one-carbon pathway but not SFXN1 results in glycine auxotrophy. Proliferation of wild-type Jurkat or single cell-derived knockout cells was assayed in full or glycine-deficient RPMI media as indicated.

Cells lacking components of the mitochondrial one-carbon pathway are auxotrophic for glycine (6, 22-24), which was confirmed using SHMT2- and MTHFD2-null cells (FIG. 7H). Because loss of SFXN1 did not cause glycine auxotrophy, it was reasoned that there must be genes that can partially compensate for it. In mammals there are five Sideroflexins, with SFXN3 being the closest homologue of SFXN1 (88% sequence similarity) (FIG. 4A). Budding yeast has only one Sideroflexin (FSF1), while *Drosophila melanogaster* has two, one most similar to SFXN1 and SFXN3 (Sfxn1-3) and the other to SFXN2 (Sfxn2) (FIG. 4A). The human, fly, and yeast Sideroflexins examined localized to mitochondria when expressed in HeLa cells (FIG. 4D).

Because Jurkat and K562 cells, like other commonly used cell lines, express multiple Sideroflexins (FIGS. 4B-4C) it was hypothesized that one or more family members might partially compensate for the loss of SFXN1, thus explaining why the SFXN1-null cells are not auxotrophic for glycine. To explore this possibility the metabolism-focused sgRNA library was used to screen for genes required for SFXN1-null Jurkat cells to proliferate in the absence of glycine. In addition to several genes in the mitochondrial (MTHFD2, SHMT2, MFT) and cytosolic (MTHFS) one-carbon pathways, the only other gene to score was SFXN3 (FIG. 4E), suggesting that it has redundant functions with SFXN1.

Figure 4J:
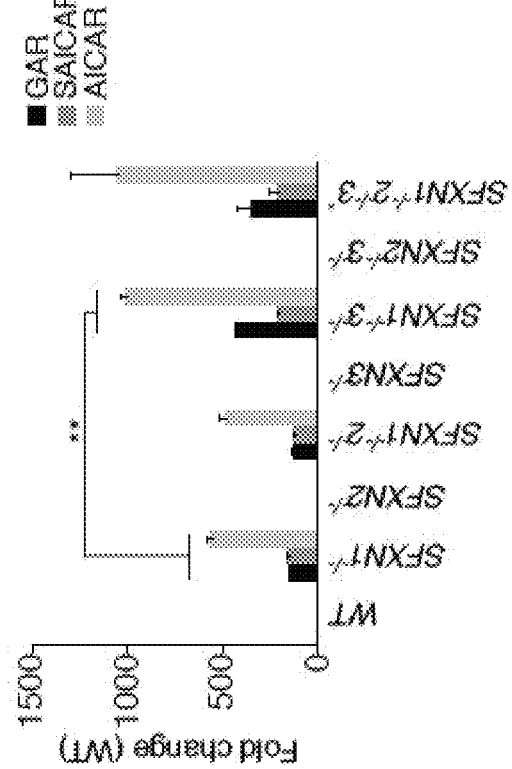

Indeed, like cells lacking SHMT2 or MTHFD2, cells null for both SFXN1 and SFXN3 (SFXN1&3 DKO cells), did not proliferate in the absence of glycine (FIG. 4F). Consistent with these cells having a severe defect in glycine synthesis, the addition of formate to the glycine-free media did not reverse their proliferation defect (FIG. 4F), while expression of either SFXN1 or SFXN3 did (FIGS. 7D-7E). Purine synthesis intermediates accumulated to greater extents in the DKO cells than in those lacking only SFXN1, while the single or combined deletions of SFXN3 and SFXN2 did not impact these metabolites (FIG. 4J). Compared to the SFXN1-null and wild-type cells, the DKO cells proliferated slowly even in full media, suggesting that beyond experiencing one-carbon unit stress these cells have limiting amounts of one-carbon donors and/or glycine.

Figures 10A, 10B:
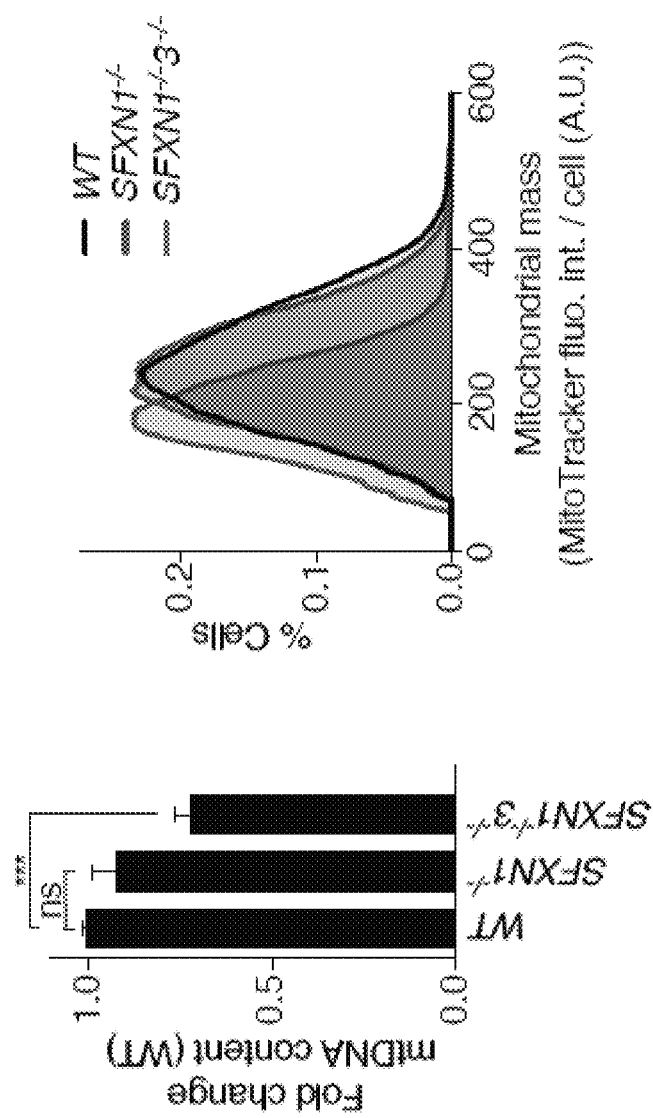
FIGS. 10A-10G demonstrate mitochondrial mass, morphology, and function of SFXN1-null cells and SFXN1 &3 double knock-out (DKO) cells.
Figure 10C:
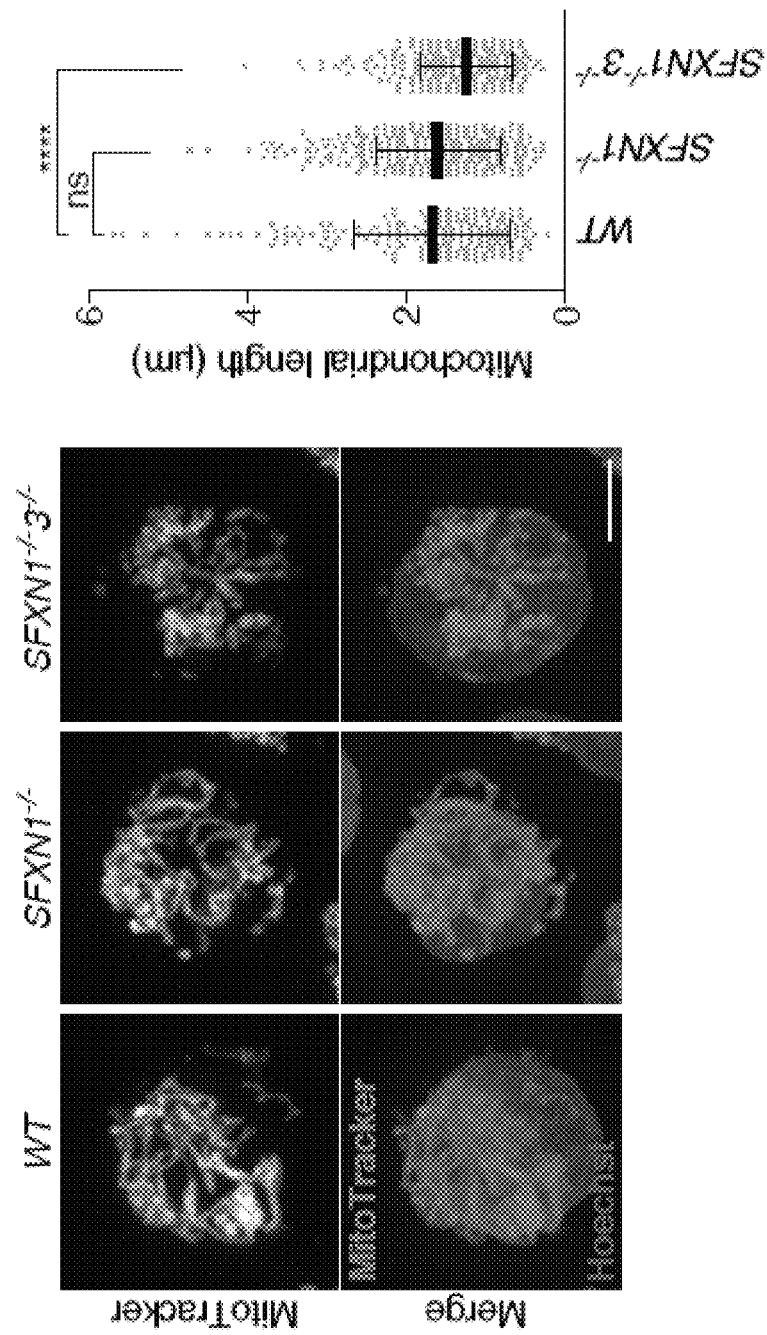
Figures 10D, 10E, 10F, 10G:
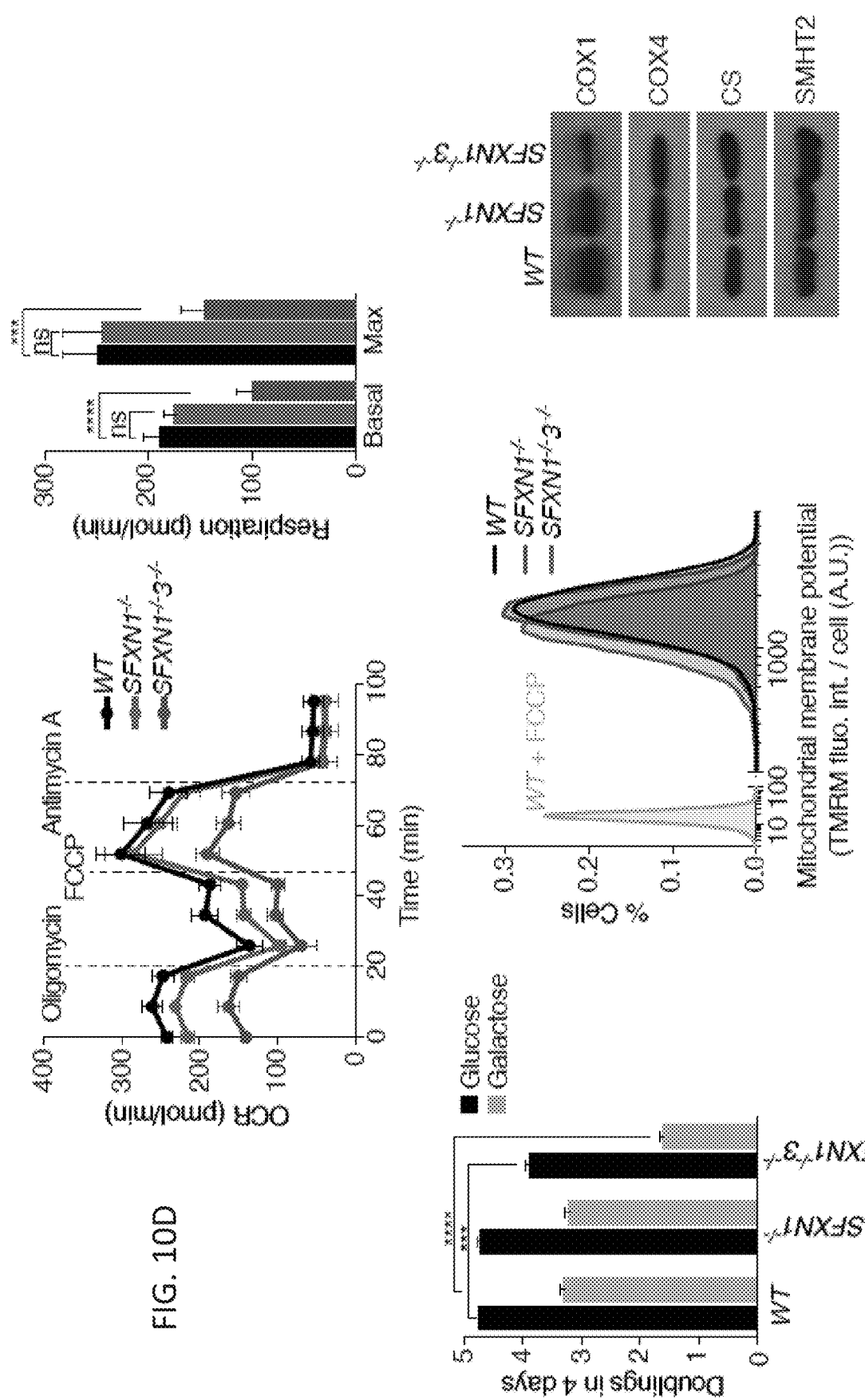

While mitochondrial mass, morphology, and function were not affected in SFXN1-null cells, SFXN1&3 DKO cells did have defects in these parameters (FIG. 10). Mitochondrial one-carbon metabolism, as well as serine itself, is needed for mitochondrial protein synthesis, and, indeed, the DKO cells had reduced levels of mitochondrially encoded proteins, likely explaining their mitochondrial dysfunction (FIG. 10G, (25-28)). Despite multiple attempts and the supplementation of full media with formate, SFXN1&2&3 triple knockout cells were not isolated, suggesting that such cells are not viable. However, one cell clone lacking SFXN1 and SFXN2 and containing low levels of SFXN3 due to an in-frame deletion was obtained (FIG. 7C) and these cells were also unable to proliferate in the absence of glycine (FIG. 4F).

Figure 4K:
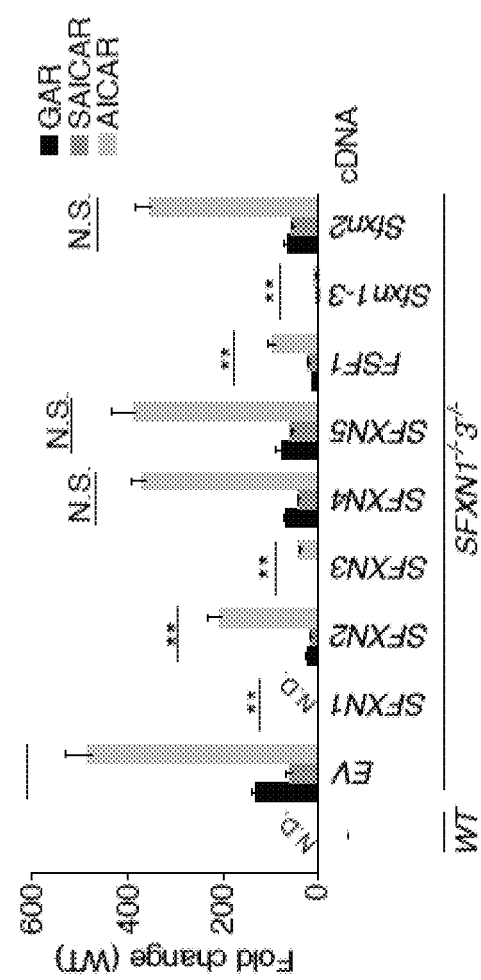

Because SFXN1 and SFXN3 are amongst the most highly expressed Sideroflexins in Jurkat cells (FIG. 4B), it was queried whether other homologs can compensate for them if expressed at higher levels. With the exception of SFXN4, overexpression of any of the human Sideroflexins reversed the glycine auxotrophy of the Jurkat SFXN1 &3 DKO cells, as did heterologous expression of yeast FSF1 and *Drosophila* Sfxn1-3 and Sfxn2 (FIG. 4H and FIG. 7G). However, besides SFXN1 and SFXN3, only SFXN2, FSF1, and Sfxn1-3 (the closest *Drosophila* homologue of SFXN1) ameliorated, to differing degrees, the defects in purine synthesis (FIG. 4K). These results suggest that serine transport is an evolutionarily conserved feature of the Sideroflexins, but that their kinetic properties and likely substrate specificities vary so that not all can support the high rate of mitochondrial serine import required to fulfill the demand for one-carbon units of proliferating cells.

Discussion

The work described herein reveals SFXN1 as a previously missing component of the one-carbon metabolism pathway that functions as a mitochondrial serine transporter. It is proposed that SFXN1 and SFXN3 (and perhaps SFXN2) are the main mitochondrial serine transporters in human cells and that Sfxn1-3 also has this function in *Drosophila melanogaster*. SFXN1 and SFXN3 likely have other physiologically relevant substrates besides serine, such as alanine or cysteine, a notion supported by the in vitro transport results, the finding that cells lacking both have more severe proliferation defects than those missing established components of the mitochondrial one-carbon pathway, and that cells lacking SFXN1 have a proliferation advantage in low cysteine media (FIG. 6L). A major use of cysteine is cytosolic glutathione synthesis and it is possible that loss of SFXN1 and thus a reduction in mitochondrial cysteine import should increase its availability for this use, which is known to be limiting for cell proliferation (29). A reduction in mitochondrial cysteine import or transport may also result in a modulated reducing and oxidizing (redox) state/antioxidant defense in a cell (e.g., increased antioxidant defense). Two reports proposed that SFXN1 can transport citrate in vitro (30, 31), but the physiological relevance of this remains unclear because SLC25A1 is well-established as the mitochondrial citrate carrier (32-34) and citrate does not compete with serine in these in vitro assays (FIG. 3C). Moreover, these studies used purified endogenous rather than recombinant protein, raising the possibility that the observed activity was due to a co-purifying contaminating protein. When overexpressed, SFXN5 can only partially complement loss of SFXN1, and it is suspected that its main function is not as a serine transporter similarly to SFXN4, which in this experimental system cannot substitute for SFXN1. It is interesting that budding yeast only has one Sideroflexin (FSF1), perhaps suggesting that is has more broad functions than its homologues in other species.

Figure 8C:
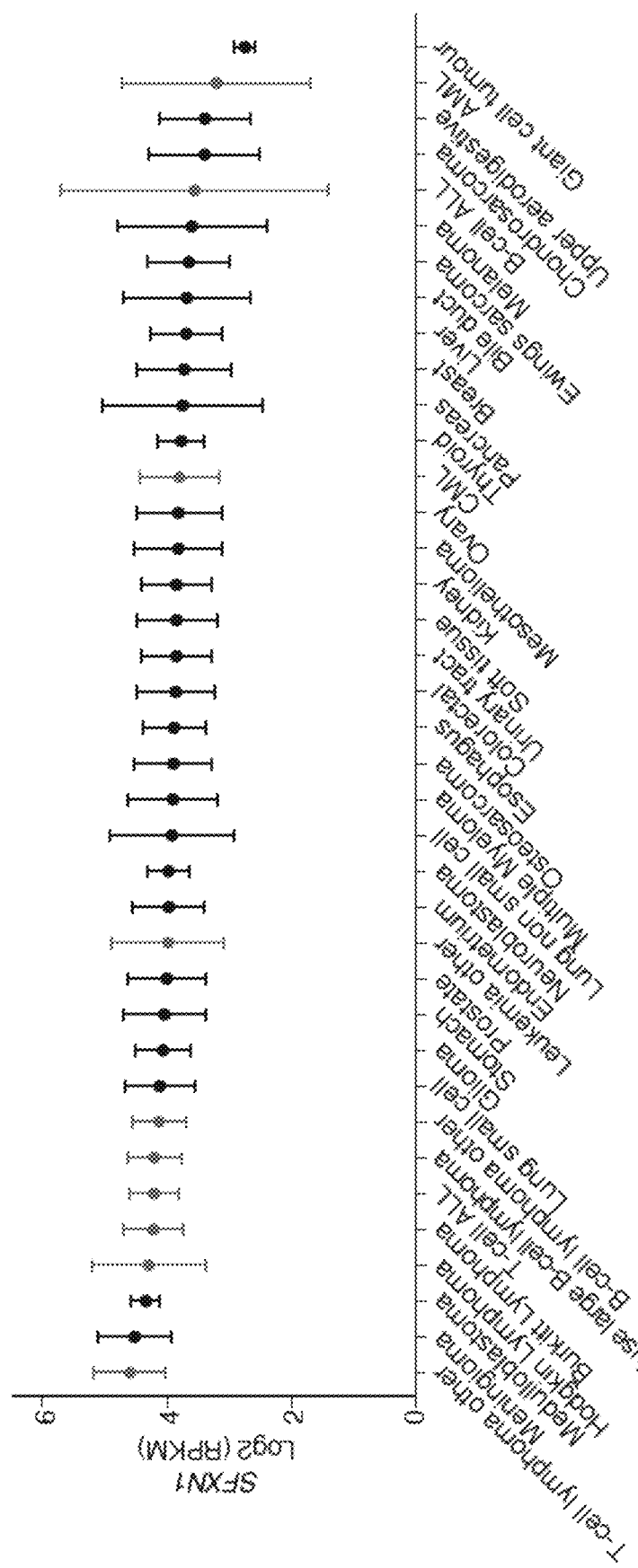

Mice with a loss-of-function mutation in Sfxn1 have a sideroblastic-like anemia characterized by iron accumulation in mitochondria (18, 35). Although Sfxn1 has been challenged as the causative gene (36), this work does provide a possible explanation for the phenotype. In humans, mutations that impair the part of the heme synthesis pathway that occurs in mitochondria, which requires glycine, cause sideroblastic anemia (37). Given that mitochondria make glycine from serine, it is speculated that in the Sfxn1-mutant mice an insufficient import of serine into mitochondria results in a decrease in glycine and thus heme synthesis. There are multiple Sideroflexins and their expression varies across tissues (FIGS. 8A-8B). Like other genes of the mitochondrial one-carbon pathway, SFXN1, 2 and 3 expression is likely regulated by the Myc transcription factor as 34, 20, and 14 Myc binding sites were found in the promoters of SFXN1, SFXN2 and SFXN3, respectively. SFXN1 is expressed in many cancers, most highly in leukemias and lymphomas (FIG. 8C), Thus, SFXN1 and its homologues may turn out to be important nodes for regulating the fate of serine in cells and also play unexplored roles in cancer cell growth.

Materials and Methods
Results
Reagents were obtained from the following sources: the antibodies that recognize SFXN1 (HPA019543), SFXN2 (HPA026834), SFXN3 (HPA048105), SFXN1, 2, and 3 (HPA008028) and SHMT2 (HPA020549) from Atlas Antibodies; AKT (4691), CALR (12238), Catalase (12980), Citrate Synthase (14309), Cytochrome c oxidase subunit 4 isoform 1 (COX4; 4850), GOLGA1 (13192), RPSS6KB1 (2708), SHMT1 (12612), VDAC (4661), the myc (2278) and HA epitopes (3724) and HRP-coupled anti-rabbit secondary antibody as well as Normal Donkey Serum from Cell Signaling Technology (CST); the FLAG epitope from CST (2368) and Sigma (F1804); LAMP2 (sc-18822), LMNA (sc-20680), MTHFD1 (sc-271412), MTHFD2 (sc-390708), TOM20 (sc-11415) and HRP-labeled anti-mouse secondary from Santa Cruz Biotechnology (SCBT); SFXN4 (CSB-PA744046LA01HU) and SFXN5 (CSB-PA819464LA01HU) from Cusabio; MTHFD1L (ab116615) from Abcam and Cytochrome c oxidase subunit 1 (COX1; 459600) from Invitrogen. The 2,3,3-2H3-serine was obtained from Cambridge Isotope Laboratories; [3H] serine and alanine from American Radiolabeled Chemicals, Inc.; amino acids and galactose from Sigma Aldrich; X-treme-GENE 9 and Complete Protease Cocktail from Roche; Alexa 488 and 568-conjugated secondary antibodies and from Invitrogen; anti-HA magnetic beads from ThermoFisher Scientific; glucose from Westnet Inc. (#BM-675); ANTI-FLAG M2 Agarose Affinity Gel and sodium formate from Sigma; egg phosphatidylcholine, $E.\ coli$ total lipids, and the lipid extruder from Avanti Polar Lipids; Bio-Beads SM-2 Adsorbents from Biorad Laboratories; filter membranes for extrusion and supports from Whatman; from Corning.

Cell Lines and Plasmids

The pMXs-IRES-Bsd vector was from Cell Biolabs. K562 and HeLa cells were purchased from ATCC. The identities of the K562, Jurkat, and HeLa cells used in this study were authenticated by STR profiling. Sequences of human SFXN1, *S. cerevisiae* FSF1 and *Drosophila melanogaster* Sfxn1-3 (CG11739) and Sfxn2 (CG6812) were synonymously mutated to remove the proto-spacer adjacent motif (PAM) sequence and/or codon-optimized for expression in human cells.

| Plasmid name | Addgene ID | Reference |
| --- | --- | --- |
| pMXs_FLAG-SFXN1 | 110634 | This study |
| pMXs_SFXN1 | 110635 | This study |
| pMXs_FLAG-SFXN2 | 110636 | This study |
| pMXs_FLAG-SFXN3 | 110637 | This study |
| pMXs_FLAG-SFXN4 | 110638 | This study |
| pMXs_FLAG-SFXN5 | 110639 | This study |
| pMXs_SFXN5 | 110640 | This study |
| pMXs_FLAG-FSF1 | 110641 | This study |
| pMXs_FLAG-Sfxn1-3 (CG11739) | 110642 | This study |
| pMXs_FLAG-Sfxn2 (CG6812) | 110643 | This study |
| pLentiCRISPR Metabolism sgRNA library | 110066 | (15) |

Cell Culture

Unless otherwise indicated, Jurkat, K562, and HEL cells were cultured in RPMI (Life Technologies) supplemented with 10% Inactivated Fetal Calf Serum (IFS, Sigma and Gemini), 2 mM glutamine, and penicillin/streptomycin. HeLa and HEK-293T cells were cultured in DMEM (Life Technologies) supplemented with 10% IFS and penicillin/streptomycin. HEK-293T cells used for virus production were cultured in IMDM (Life Technologies) supplemented with 20% IFS, and penicillin/streptomycin. To prepare media lacking serine or glycine, RPMI without amino acids and glucose (US Biological) was supplemented with amino acids except serine and glycine and 11 mM glucose according to the RPMI 1640 formulation (Life Technologies) with the addition of 130 μM alanine (except in CRISPR screens) as well as dialyzed IFS and penicillin/streptomycin. Serine or glycine, or both amino acids (for control media) were added to the media in experiments as indicated. Dropout media for other amino acids was prepared accordingly. To compare proliferation of cells in glucose to proliferation in galactose, RPMI without amino acid and glucose was supplemented with amino acids, dialyzed IFS, and either 11 mM glucose or galactose.

Virus Production

HEK-293T cells were co-transfected with the pLentiCRISPR sgRNA library, the VSV-G envelope plasmid and the AVPR lentiviral packaging plasmid, or with pMXS plasmids and retroviral packaging plasmids Gag-Pol and VSV-G, using X-TremeGene 9 Transfection Reagent. The culture medium was exchanged 24 hours after transfection with the same medium instead supplemented with 30% IFS. The virus-containing supernatant was collected 48 hours after transfection and spun for 5 min at 400×g to eliminate cells.

Transduction of Cell Lines

Cells were seeded at a density of $1 \times 10^6$ cells/mL in RPMI containing 8 μg/mL polybrene (EMD Millipore), and then transduced with lentivirus by centrifugation at 2,200 RPM for 45 min at 37° C. After an 18-hour incubation, cells were pelleted to remove virus, washed twice in PBS and then re-seeded into fresh culture medium containing puromycin or blasticidin, and selected for 72 hours.

CRISPR/Cas9-Mediated Generation of Knockout Cell Lines

Human SFXN1, SFXN2, SHMT1, SHMT2, MTHFD2 were depleted using the lentiviral pLentiCRISPRv1 system. The following sense (S) and antisense (AS) oligonucleotides were cloned into pLentiCRISPRv1:

sgSFXN1_3 (S): caccgGATAGGAAGAATGTCAGCCC (SEQ ID NO: 19)

sgSFXN1_3 (AS): aaacGGGCTGACATTCTTCCTATCc (SEQ ID NO: 20)

sgSFXN1_5 (S): caccgGTTCATAATGAATGGAGGGA (SEQ ID NO: 21)

sgSFXN1_5 (AS): aaacTCCCTCCATTCATTATGAACc (SEQ ID NO: 22)

sgSFXN2_1 (S): caccgGGACTGGGCCAAGGTGATGG (SEQ ID NO: 23)

sgSFXN2_1 (AS): aaacCCATCACCTTGGCC-CAGTCCc (SEQ ID NO: 24)

sgSHMT1_2 (S): caccgGAAGGAGAGTAAC-CGGCAGA (SEQ ID NO: 25)

sgSHMT1_2 (AS): aaacTCTGCCGGTTACTCT-CCTTCc (SEQ ID NO: 26)

sgSHMT2_1 (S): caccgGAGAAGGACAGGCA-GTGTCG (SEQ ID NO: 27)

sgSHMT2_1 (AS): aaacCGACACTGCCTGTC-CTTCTCc (SEQ ID NO: 28)

sgMTHFD2_2 (S): caccgGGTGGAAAGGG-CGAAGGCGA (SEQ ID NO: 29)

sgMTHFD2_2 (AS): aaacTCGCCTTCGCCCTTTC-CACCc (SEQ ID NO: 30)

SFXN3 was depleted using pX330 with the following guide:

sgSFXN3_10 (S): caccgGAGTGCCACCACTGGA-GCTG (SEQ ID NO: 31)

sgSFXN3_10 (AS): aaacCAGCTCCAGTGGTGG-CACTCc (SEQ ID NO: 32)

After selection of guide-transfected or transduced cells, cells were single-cell FACS-sorted into 96-well plates. Cell clones with the desired knockouts were identified by western blotting. Control cells were generated by targeting the AAVS1 locus as described before (14). Double knockout cells were generated by sequential rounds of single cell cloning.

CRISPR/Cas9 Negative Selection Genetic Screens

Cells were infected with a sgRNA library targeting 3000 metabolic genes and transporters and containing 500 control sgRNAs (15). 48 hours after infection cells, were selected with puromycin for 72 hours. After 48 hours of recovery post-selection, cells were seeded into RPMI with or without serine or glycine as indicated. Cells were passaged every other day, with seeding densities of 250,000 cells/ml for Jurkat cells and 175,000 cells/ml for K562 cells until reaching ~14-15 population doublings (PDs) in full media and glycine-deficient media or ~9 population doublings in serine-deficient media (because cells proliferated more slowly in the absence of serine compared to in full RPMI media). Wild-type and SFXN1-null cells in the SFXN1 synthetic lethality screen grown in glycine-deficient media were resuspended in fresh media lacking glycine every day from PD ~8 to the end of the screen to prevent accumulation of secreted glycine. DNA was extracted from 30-50×10$^6$ cells using the QIAamp DNA Blood Maxi Kit (QIAGEN). sgRNA inserts were PCR amplified using Ex Taq DNA Polymerase (Takara). The resultant PCR products were purified and sequenced on a HiSeq 2500 (Illumina) (primer sequences provided below) to monitor the change in the abundance of each sgRNA between the initial and final cell populations.

Primer Sequences for sgRNA Quantification Forward: AATGATACGGCGACCACCGAGATCTACACGA-ATACTGCCATTTGTC TCAAGATCTA (SEQ ID NO: 15)

Reverse: CAAGCAGAAGACGGCATACGAGATC-nnnnnnTTTCTTGGGTAGTTTGCAGTTTT (nnnnnn denotes the sample barcode) (SEQ ID NO: 16).

Illumina Sequencing Primer CGGTGCCACTTTTTCAAGTTGATAACGGACT-AGCCTTATTTTAACTT GCTATTTCTAG CTCTAAAAC (SEQ ID NO: 17)

Illumina Indexing Primer TTTCAAGTTACGGTAAGCATATGATAGTCCATTT-TAAAACATAATTT TAAAACTGCAA ACTACC-CAAGAAA (SEQ ID NO: 18)

Sequencing reads were aligned to the sgRNA library and the abundance of each sgRNA was calculated. sgRNAs with less than 30 counts in the initial cell pool were removed from downstream analyses. The log$_2$ fold-change in abundance of each sgRNA was calculated for each treatment condition after adding a pseudocount of one. For the SFXN1 synthetic lethality screen sgRNAs with less than 24 counts in the initial cell pool were removed from downstream analyses. A pseudocount of one was added to all sgRNAs and counts were normalized by number of reads in each sample multiplied by one million. Gene scores were defined as the average log$_2$ fold-change in the abundance of all sgRNAs targeting a given gene between the initial and final cell populations and calculated for all treatment conditions. The differential gene score was calculated as the difference in gene scores between treatment conditions.

Cell Proliferation Assays 10,000 cells per well were seeded into 96-well plates in triplicate. Cell titer glo reagent (Promega) was added to one plate immediately after seeding and luminescence was measured, while a second plate was read-out 4 days after seeding. Number of doublings in 4 days was determined by calculating the log$_2$ fold-change in signal between day 0 and 4. For formate rescue experiments, 1 mM formate was added to media at the time of seeding (Jurkat cells) or cells were cultured in formate-containing media for 1 week prior to the experiment (K562 cells) unless indicated otherwise.

MS-Based Metabolomics and Quantification of Metabolite Abundances

Metabolite abundance using LC/MS-based metabolomics was measured and quantified as previously described (15). Briefly, Jurkat or K562 cells were seeded at densities of 0.6×10$^6$ per ml and 0.33×10$^6$ per ml, respectively. 24 hours later, 1.5-2×10$^6$ Jurkat or 1×10$^6$ K562 cells were harvested, washed once in ice-cold 0.9% saline prepared with LC-MS-grade water, and extracted with 80% methanol containing 500 nM isotope-labeled amino acids as internal standards (Cambridge Isotope Laboratories). The samples were vortexed for 10 min at 4° C. and centrifuged at 17,000×g. The supernatant was dried by vacuum centrifugation at 4° C. Samples were stored at −80° C. until analyzed. On the day of analysis, samples were resuspended in 50-100 μL of LC-MS-grade water and the insoluble fraction was cleared by centrifugation at 15,000 rpm. The supernatant was then analyzed as previously described by LC-MS (15, 38) Amino acids were normalized to their respective internal standards, purine synthesis intermediates were normalized to the glutamate internal standard. Folate measurements were performed as previously described (39, 40). For GC-MS analysis of amino acids, samples were prepared as for LC-MS analysis, but after drying the samples were derivatized using N-tert-Butyldimethylsilyl-N-methyltrifluoroacetamide (Sigma-Aldrich) as previously described (41).

Serine Tracing Experiments

Cells were cultured for 12 hours in serine deficient RPMI containing 285 μM 2,3,3-$^2$H$_3$-serine (Cambridge Isotope Laboratories), supplemented with 10% dialyzed serum. Cells were extracted for LC-MS metabolite analysis as described above. For LC-MS analysis of labeled nucleotides, dried samples were resuspended in 40 μL LC-MS-grade water and 10 μL were injected. Mass isotopomer distributions were corrected for natural abundance using in-house algorithms as previously described (41).

In parallel, culture supernatant was collected, and after removal of cells by centrifugation, 20 μL were extracted for GC-MS analysis with 300 μL acetone containing 1 μg norvaline. Samples were vortexed briefly and spun 10 min at 4° C. 200 μl of the supernatant were dried down using a nitrogen dryer and derivatized and analyzed as described above. Mass isotopomer distributions were determined by integrating metabolite ion fragments and corrected for natural abundance using in-house algorithms as previously described (41). Glycine levels were normalized to norvaline.

Immunofluorescence Assays and STED Imaging

For immunofluorescence assays 50,000 HeLa cells were plated in a 24-well glass bottom imaging plate (Cellvis, Mountain View, Calif.) and transfected with 500 ng of the cDNAs for FLAG-Sideroflexin constructs 16 hours later. 48 hours after transfection, cells were rinsed twice with PBS and fixed with 3% paraformaldehyde with 0.1% glutaraldehyde in PBS for 10 minutes at room temperature. Cells were rinsed three times with PBS and permeabilized with 0.3% NP40, 0.05% Triton X-100, 0.1% BSA in PBS for 3 minutes at room temperature. After rinsing three times with wash buffer (0.05% NP40, 0.05% Triton-X 100, 0.2% BSA in PBS) samples were blocked for 1 hour in blocking buffer (0.05% NP40, 0.05% Triton-X 100, 5% Normal Donkey Serum) at room temperature. The samples were incubated with primary antibody in blocking buffer for 1 hour at room temperature, washed three times with wash buffer, and incubated with secondary antibodies produced in donkey (diluted 1:500 in blocking buffer) for 30 minutes at room temperature in the dark, washed three times with wash buffer, and rinsed three times with PBS. The primary antibodies used were directed against COX4 (CST; 1:250 dilution), the FLAG epitope (Sigma, 1:1000 dilution) and TOM20 (SCBT, 1:1000). Secondary antibodies conjugated with Alexa 488 and 568 were used for confocal microscopy and antibodies conjugated with ATTO594 and ATTO647N were used for STED imaging.

Images were acquired on a Zeiss AxioVert200M microscope with a 63× oil immersion objective and a Yokogawa CSU-22 spinning disk confocal head with a *Borealis* modification (Spectral Applied Research/Andor) and a Hamamatsu ORCA-ER CCD camera. The MetaMorph software package (Molecular Devices) was used to control the hardware and image acquisition. The excitation lasers used to capture the images were 488 nm and 647 nm. Images were processed with FIJI (42). STED imaging was carried out on a commercial Leica TCS SP8 STED 3× setup with a white light excitation laser. Wavelengths of 594 and 650 nm were used to excite ATTO594 and ATTO647N respectively. For detection HyD 1 and HyD 2 were used and set to 604-644 and 665-705 nm windows. The 775-nm depletion laser was used for both dyes. The two colors were imaged sequentially line by line. STED images were deconvolved to reduce noise using the Richardson-Lucy algorithm implemented in the python-microscopy package (python-microscopy.org). Line profiles were generated from the raw data using FIJI.

Mitochondrial Isolations for Immunoblot Analyses $30 \times 10^6$ Jurkat or K562 cells expressing the HA-mito tag or a control tag were washed 1× in PBS, 1× in KPBS according to (38). 5 µl of the cell suspension in 1 ml KPBS was lysed in 50 µl of 1% Triton lysis buffer to obtain whole cell protein levels. The rest was lysed using 8 or 5 strokes for Jurkat and K562 cells, respectively, with a 301/2 G needle. Lysates were spun for 1 min at 1000×g to pellet unbroken cells, and subsequently incubated with 100 µl HA-magnetic beads for 4 min. Beads were washed 3× in KPBS, and mitochondria lysed in 50 µl lysis buffer for 10 min. Beads were removed using the magnet, and samples were spun 10 min at 17,000×g to remove residual beads and insoluble material. SDS-PAGE loading dye was added to each sample, and for Jurkat cells 6 µl of whole cell lysate and 9 µl of the mitochondrial fraction were analyzed by SDS-PAGE, for K562 cells 12 µl each of the whole cell lysate and mitochondrial fraction.

In Vitro Transport Assays

In vitro transport assays were performed as described previously (43, 44) with the following specifications. FLAG-SFXN1 was purified from HEK-293T cells stably expressing the protein using FLAG-affinity purification and eluted off the beads with the FLAG peptide.

1% Phosphatidylcholine was added to total *E. coli* lipids in chloroform, evaporated under nitrogen and desiccated overnight. Dried lipids were hydrated in inside buffer (20 mM MES pH 7, 50 mM NaCl, 20 mM KCl) by freeze-thawing in liquid nitrogen 20× times. Lipids were extruded 6× through a 0.4 µm filter and 15× through a 0.1 µm filter. 15 µg of purified SFXN1 protein were reconstituted into 1.2 mg liposomes using a detergent:lipid ratio of 5:1 with the addition of 1 mM DTT in inside buffer rotating at 4° C. for 1 hour. The proteoliposomes were incubated for 3 sequential rounds with Bio-Beads to remove detergent. A liposome-only control was prepared by replacing the protein with inside buffer in the reconstitution reaction. Incorporation of protein into liposomes was assessed using a glycerol gradient centrifugation assay. [3H] Serine at 1 µM and alanine at 500 nM were used as substrates and a buffer containing 20 mM Tris-HCL pH 7.4 and 100 mM NaCl was used as outside buffer in the transport reactions. Different lots of total *E. coli* lipid extracts were tested and ones that optimally preserved SFXN1 activity were used in experiments.

Amino Acid Uptake into Isolated Mitochondria

Mitochondria from wild-type or SFXN1-null Jurkat cells were prepared according to (45). Briefly, cells (~1 g starting material) were resuspended in low tonicity buffer (100 mM sucrose, 10 mM MOPS pH 7.2, 1 mM EGTA, 0.1% BSA) and disrupted with 20 strokes in a homogenizer containing a pure PTFE head (VWR International) and two strokes with a dounce tissue grinder with tight-fitting pestle (DWK Life Sciences Kimbl Kontes). After adjusting tonicity, lysates were spun twice at 950×g to remove unbroken cells and nuclei, and mitochondria were pelleted by centrifuging at 10,000×g for 10 min. The supernatant as well as the top, white part of the pellet containing other membranes was aspirated and the brown/yellow mitochondrial pellet was washed in isolation buffer (210 mM mannitol, 70 mM sucrose, 10 mM MOPS pH 7.2, 1 mM EGTA, 0.1% BSA) before resuspending in mitochondria incubation media (125 mM KCl, 10 mM MOPS pH 7.2, 2 mM MgCl2, 2 mM KH2PO4, 10 mM NaCl, 1 mM EGTA). Mitochondrial preparations were adjusted for protein content. 200 µl volume uptake reactions with 0.75 µM [3H] serine, 0.175 mM pyridoxal phosphate, 1 µM NAD+, and 2 µM tetrahydrofolate or 3 µM [3H] glutamate (46) were initiated by adding ~100 µg of mitochondria to incubation media containing substrates at 30° C. 50 µl samples were collected immediately after start of the reaction and at 1, 2, 3 mins and added to mixed cellulose-ester filters (Fisher Scientific, 0.22 µm pore size) connected to a vacuum line (adapted from (47)). Filters were washed with 3 mL of ice cold TBS and the radioactivity remaining on the filters was measured using a scintillation counter. Blank reaction samples, in which mitochondria were replaced with incubation media, were used to subtract the background. The uptake rate was calculated from the first two minutes of the reaction.

Mitochondrial Characterization

For quantification of mitochondrial mass and morphology, Jurkat cells were stained with MitoTracker DeepRed FM (Life Technologies, M22426) at 25 nM for 1 h before analysis by flow cytometry or fluorescence microscopy. For microscopy, nuclei were stained with Hoechst 33342 fluorescent stain (Molecular Probes) at 2 µg/ml and z-stacks with 250 nm step size were taken at 100× magnification. FIJI was used to generate max intensity z-projections and measure mitochondrial length (42). To measure mitochondrial membrane potential cells were stained with 200 nM tetramethylrhodamine, methyl ester, perchlorate (TMRM; Life Technologies, T668) in RPMI for 20 min at 37° C., washed once with PBS, and resuspended in fresh PBS for flow cytometry analysis of live cells. Where indicated, cells were incubated with 10 µM FCCP for 10 min prior to adding TMRM dye. Analysis of mtDNA copy number was performed as previously described (48). Briefly, genomic and mitochondrial DNA were extracted from cells using the QIAamp DNA mini kit according to the manufacturer's instructions (Qiagen). The following primers targeting the mitochondrial gene ND1 and the nuclear gene RUNX2 were used to assess mtDNA copy number by qPCR by normalizing Ct values of ND1 to those of RUNX2. ND1_F: CCC TAA AAC CCG CCA CAT CT (SEQ ID NO: 33); ND1_R: GAG CGA TGG TGA GAG CTA AGG T (SEQ ID NO: 34); RUNX2_F: CGC ATT CCT CAT CCC AGT ATG (SEQ ID NO: 35); RUNX2_R: AAA GGA CTT GGT GCA GAG TTC AG (SEQ ID NO: 36).

Oxygen consumption rates (OCR) of intact cells were measured using an XF24 Extracellular Flux Analyzer (Agilent). 200,000 cells were seeded on Seahorse XF24 cell culture plates coated with Cell-tak and assayed after incubation at 37° C. for 1 h. Three basal OCR measurements were taken, followed by sequential injections of 1 oligomycin, 3 µM FCCP, and 1 µM antimycin A, taking three measurements following each treatment. Cellular respiration was calculated by subtracting the OCR after Antimycin A treatment from the basal or FCCP-stimulated OCR.

Bioinformatics Analyses

SFXN1 topology was predicted using Protter (49). For construction of the phylogenetic tree, Sideroflexin homologue protein sequences (SFXN1_HUMAN Q9H9B4, SFXN2_HUMAN Q96NB2, SFXN3_HUMAN Q9BWM7, SFXN4_HUMAN Q6P4A7, SFXN5_HUMAN Q8TD22, FSF1_YEAST Q12029, Q9VN13_DROME, Q9VVW3_DROME) were aligned using MUSCLE (50). The PHYLIP proml module (51) was used to construct the phylogenetic tree and FigTree software v.1.4.3 to visualize it. Percent sequence similarities were calculated with the NCBI blastp tool. Graphpad Prism 7 software was used to generate the heat map of Sideroflexin RNA expression based on data from the Cancer Cell Line Encyclopedia (broadinstitute.org/ccle).

Statistical Analyses

Two-tailed t tests were used for comparison between two groups. All comparisons were two-sided, and P values of less than 0.05 were considered to indicate statistical significance. All error bars denote standard deviations between biological replicates unless indicated otherwise.

REFERENCES

1. M. Yang, K. H. Vousden, Serine and one-carbon metabolism in cancer. *Nat Rev Cancer* 16, 650-662 (2016).
2. J. W. Locasale, Serine, glycine and one-carbon units: cancer metabolism in full circle. *Nat Rev Cancer* 13, 572-583 (2013).
3. G. S. Ducker, J. D. Rabinowitz, One-Carbon Metabolism in Health and Disease. *Cell Metab* 25, 27-42 (2017).
4. A. S. Tibbetts, D. R. Appling, Compartmentalization of Mammalian folate-mediated one-carbon metabolism. *Annu Rev Nutr* 30, 57-81 (2010).
5. C. K. Barlowe, D. R. Appling, In vitro evidence for the involvement of mitochondrial folate metabolism in the supply of cytoplasmic one-carbon units. *Biofactors* 1, 171-176 (1988).
6. W. Pfendner, L. I. Pizer, The metabolism of serine and glycine in mutant lines of Chinese hamster ovary cells. *Arch Biochem Biophys* 200, 503-512 (1980).
7. M. R. Narkewicz, S. D. Sauls, S. S. Tjoa, C. Teng, P. V. Fennessey, Evidence for intracellular partitioning of serine and glycine metabolism in Chinese hamster ovary cells. *Biochem J* 313, 991-996 (1996).
8. G. S. Ducker et al., Reversal of Cytosolic One-Carbon Flux Compensates for Loss of the Mitochondrial Folate Pathway. *Cell Metab* 23, 1140-1153 (2016).
9. T. F. Fu, J. P. Rife, V. Schirch, The role of serine hydroxymethyltransferase isozymes in one-carbon metabolism in MCF-7 cells as determined by 13C NMR. *Arch Biochem Biophys* 393, (2001).
10. C. Yu, D. L. Claybrook, A. H. Huang, Transport of glycine, serine, and proline into spinach leaf mitochondria. *Arch Biochem Biophys* 227, 180-187 (1983).
11. R. L. Cybulski, R. R. Fisher, Swelling of mitochondria in response to L-isomers of serine, alanine, methionine, valine, threonine, leucine, proline, glycine. *Biochemistry* 16, 5116-5512 (1977).
12. R. L. Cybulski, R. R. Fisher, Intramitochondrial localization and proposed metabolic significance of serine transhydroxymethylase. *Biochemistry* 15, 3183-3187 (1976).
13. C. F. Labuschagne, N. J. van den Broek, G. M. Mackay, K. H. Vousden, O. D. Maddocks, Serine, but not glycine, supports one-carbon metabolism and proliferation of cancer cells. *Cell Rep* 7, 1248-1258 (2014).
14. T. Wang et al., Identification and characterization of essential genes in the human genome. *Science* 350, 1096-1101 (2015).
15. K. Birsoy, Wang, T., Chen, W. W., Freinkman, E., Abu-Remaileh, M., Sabatini, D. M., An Essential Role of the Mitochondrial Electron Transport Chain in Cell Proliferation Is to Enable Aspartate Synthesis. *Cell* 162, 540-551 (2015).
16. Y. Pikman et al., Targeting MTHFD2 in acute myeloid leukemia. *J Exp Med* 213, 1285-1306 (2016).
17. M. S. Field, D. M. Szebenyi, P. J. Stover, Regulation of de novo purine biosynthesis by methenyltetrahydrofolate synthetase in neuroblastoma. *J Biol Chem* 281, 4215-4221 (2006).
18. M. D. Fleming, D. R. Campagna, J. N. Haslett, C. C. Trenor, N. C. Andrews, A mutation in a mitochondrial transmembrane protein is responsible for the pleiotropic hematological and skeletal phenotype of flexed-tail (f/f) mice. *Genes Dev* 15, 652-657 (2001).
19. G. Miotto, S. Tessaro, G. A. Rotta, D. Bonatto, In silico analyses of Fsf1 sequences, a new group of fungal proteins orthologous to the metazoan sideroblastic anemia-related sideroflexin family *Fungal Genet Biol* 44, 740-753 (2007).
20. S. Y. Lee et al., APEX Fingerprinting Reveals the Subcellular Localization of Proteins of Interest. *Cell Rep* 15, 1837-1847 (2016).
21. K. Herbig et al., Cytoplasmic serine hydroxymethyltransferase mediates competition between folate-dependent deoxyribonucleotide and S-adenosylmethionine biosyntheses. *Journal of Biological Chemistry* 277, 38381-38389 (2002).
22. F. T. Kao, T. Puck, Mutagenesis and genetic analysis with Chinese hamster auxotrophic cellmarkers. *Genetics* 79, 343-352 (1975).
23. M. W. McBurney, G. F. Whitmore, Isolation and biochemical characterization of folate deficient mutants of Chinese hamster cells. *Cell* 2, 173-182 (1974).
24. H. Patel, E. D. Pietro, R. E. MacKenzie, Mammalian fibroblasts lacking mitochondrial NAD+-dependent methylenetetrahydrofolate dehydrogenase-cyclohydrolase are glycine auxotrophs. *J Biol Chem* 278, 19436-19441 (2003).
25. R. Bianchetti, G. Lucchini, P. Crosti, P. Tortora, Dependence of mitochondrial protein synthesis initiation on formylation of the initiator methionyl-tRNAf. *J Biol Chem* 252, 2519-2523 (1977).

26. N. Takeuchi et al., Recognition of tRNAs by Methionyl-tRNA transformylase from mammalian mitochondria. *J Biol Chem* 276, 20064-20068 (2001).
27. R. J. Morscher et al., Mitochondrial translation requires folate-dependent tRNA methylation. *Nature* 554, 128-+ (2018).
28. D. R. Minton et al., Serine Catabolism by SHMT2 Is Required for Proper Mitochondrial Translation Initiation and Maintenance of Formylmethionyl-tRNAs. *Molecular Cell* 69, 610-+(2018).
29. G. S. Ducker et al., Human SHMT inhibitors reveal defective glycine import as a targetable metabolic vulnerability of diffuse large B-cell lymphoma. *Proc Natl Acad Sci USA* 114, (2017).
30. S. Miyake et al., Identification and characterization of a novel mitochondrial tricarboxylate carrier. *Biochem Biophys Res Commun* 295, 463-468 (2002).
31. A. Azzi, M. Glerum, R. Koller, W. Mertens, S. Spycher, The mitochondrial tricarboxylate carrier. *J Bioenerg Biomembr* 25, 515-524 (1993).
32. F. Bisaccia, A. De Palma, F. Palmieri, Identification and purification of the tricarboxylate carrier from rat liver mitochondria. *Biochim Biophys Acta* 977, 171-176 (1989).
33. R. S. Kaplan, J. A. Mayor, D. O. Wood, The mitochondrial tricarboxylate transport protein. cDNA cloning, primary structure, and comparison with other mitochondrial transport proteins. *J Biol Chem* 268, 13682-13690 (1993).
34. F. Palmieri, The mitochondrial transporter family SLC25: identification, properties and physiopathology. *Mol Aspects Med* 34, 465-484 (2013).
35. H. Gruneberg, The anaemia of flexed-tailed mice (*Mus musculus* L.) II. Siderocytes. *Journal of Genetics* 44, 246-271 (1942).
36. L. E. Lenox, J. M. Perry, R. F. Paulson, BMP4 and Madh5 regulate the erythroid response to acute anemia. *Blood* 105, 2741-2748 (2005).
37. M. D. Fleming, Congenital Sideroblastic Anemias: Iron and Heme Lost in Mitochondrial Translation. *Hematology—American Society Hematology Education Program*, 525-531 (2011).
38. W. W. Chen, E. Freinkman, T. Wang, K. Birsoy, D. M. Sabatini, Absolute Quantification of Matrix Metabolites Reveals the Dynamics of Mitochondrial Metabolism. *Cell* 166, 1324-1337 e1311 (2016).
39. L. Chen, G. S. Ducker, W. Lu, X. Teng, J. D. Rabinowitz, An LC-MS chemical derivatization method for the measurement of five different one-carbon states of cellular tetrahydrofolate. *Anal Bioanal Chem* 409, 5955-5964 (2017).
40. N. Kanarek et al., Histidine catabolism is a major determinant of methotrexate sensitivity. *Nature accepted*, (2018).
41. C. A. Lewis et al., Tracing compartmentalized NADPH metabolism in the cytosol and mitochondria of mammalian cells. *Mol Cell* 55, 253-263 (2014).
42. J. Schindelin et al., Fiji: an open-source platform for biological-image analysis. *Nat Methods* 9, 676-682 (2012).
43. G. A. Wyant et al., mTORC1 Activator SLC38A9 Is Required to Efflux Essential Amino Acids from Lysosomes and Use Protein as a Nutrient. *Cell* 171, 642-+ (2017).
44. S. Wang et al., Metabolism. Lysosomal amino acid transporter SLC38A9 signals arginine sufficiency to mTORC1. *Science* 347, 188-194 (2015).
45. A. Panov, Z. Orynbayeva, Bioenergetic and Antiapoptotic Properties of Mitochondria from Cultured Human Prostate Cancer Cell Lines PC-3, DU145 and LNCaP. *PlosOne* 8, (2013).
46. A. Minn, J. Gayet, Kinetic study of glutamate transport in rat brain mitochondria. *Journal of Neurochemistry* 29, 873-881 (1977).
47. D. K. Bricker et al., A Mitochondrial Pyruvate Carrier Required for Pyruvate Uptake in Yeast, *Drosophila*, and Humans. *Science* 337, 96-100 (2012).
48. W. W. Chen et al., Inhibition of ATPIF1 ameliorates severe mitochondrial respiratory chain dysfunction in mammalian cells. *Cell Rep* 7, 27-34 (2014).
49. U. Omasits, C. H. Ahrens, S. Muller, B. Wollscheid, Protter: interactive protein feature visualization and integration with experimental proteomic data. *Bioinformatics* 30, 884-886 (2014).
50. R. C. Edgar, MUSCLE: multiple sequence alignment with high accuracy and high throughput. *Nucleic Acids Res* 32, 1792-1797 (2004).
51. J. Felsenstein, PHYLIP—Phylogeny Inference Package (Version 3.2). *Cladistics* 5, 164-166 (1989).
52. M. S. Kim et al., A draft map of the human proteome. *Nature* 509, 575-581 (2014).
53. J. Barretina et al., The Cancer Cell Line Encyclopedia enables predictive modelling of anticancer drug sensitivity. *Nature* 483, 603-607 (2012).

Those skilled in the art will recognize, or be able to ascertain using no more than routine experimentation, many equivalents to the specific embodiments described herein. The scope of the present invention is not intended to be limited to the Description or the details set forth therein. Articles such as "a", "an" and "the" may mean one or more than one unless indicated to the contrary or otherwise evident from the context. Claims or descriptions that include "or" or "and/or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims (whether original or subsequently added claims) is introduced into another claim (whether original or subsequently added). For example, any claim that is dependent on another claim can be modified to include one or more element(s), feature(s), or limitation(s) found in any other claim, e.g., any other claim that is dependent on the same base claim. Any one or more claims can be modified to explicitly exclude any one or more embodiment(s), element(s), feature(s), etc. For example, any particular sideroflexin, sideroflexin modulator, cell type, cancer type, etc., can be excluded from any one or more claims.

It should be understood that (i) any method of classification, prediction, treatment selection, treatment, etc., can include a step of providing a sample, e.g., a sample obtained from a subject in need of classification, prediction, treatment selection, treatment, for cancer, e.g., a cancer sample obtained from the subject; (ii) any method of classification, prediction, treatment selection, treatment, etc., can include a step of providing a subject in need of such classification, prediction, treatment selection, treatment, or treatment for cancer.

Where the claims recite a method, certain aspects of the invention provide a product, e.g., a kit, agent, or composition, suitable for performing the method.

Where elements are presented as lists, e.g., in Markush group format, each subgroup of the elements is also disclosed, and any element(s) can be removed from the group. For purposes of conciseness only some of these embodiments have been specifically recited herein, but the present disclosure encompasses all such embodiments. It should also be understood that, in general, where the invention, or aspects of the invention, is/are referred to as comprising particular elements, features, etc., certain embodiments of the invention or aspects of the invention consist, or consist essentially of, such elements, features, etc.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. Where phrases such as "less than X", "greater than X", or "at least X" is used (where X is a number or percentage), it should be understood that any reasonable value can be selected as the lower or upper limit of the range. It is also understood that where a list of numerical values is stated herein (whether or not prefaced by "at least"), the invention includes embodiments that relate to any intervening value or range defined by any two values in the list, and that the lowest value may be taken as a minimum and the greatest value may be taken as a maximum. Furthermore, where a list of numbers, e.g., percentages, is prefaced by "at least", the term applies to each number in the list. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments 5% or in some embodiments 10% of a number in either direction (greater than or less than the number) unless otherwise stated or otherwise evident from the context (e.g., where such number would impermissibly exceed 100% of a possible value).

It should be understood that, unless clearly indicated to the contrary, in any methods claimed herein that include more than one act, the order of the acts of the method is not necessarily limited to the order in which the acts of the method are recited, but the disclosure encompasses embodiments in which the order is so limited. In some embodiments a method may be performed by an individual or entity. In some embodiments steps of a method may be performed by two or more individuals or entities such that a method is collectively performed. In some embodiments a method may be performed at least in part by requesting or authorizing another individual or entity to perform one, more than one, or all steps of a method. In some embodiments a method comprises requesting two or more entities or individuals to each perform at least one step of a method. In some embodiments performance of two or more steps is coordinated so that a method is collectively performed. It should also be understood that unless otherwise indicated or evident from the context, any product or composition described herein may be considered "isolated". It should also be understood that, where applicable, unless otherwise indicated or evident from the context, any method or step of a method that may be amenable to being performed mentally or as a mental step or using a writing implement such as a pen or pencil, and a surface suitable for writing on, such as paper, may be expressly indicated as being performed at least in part, substantially, or entirely, by a machine, e.g., a computer, device (apparatus), or system, which may, in some embodiments, be specially adapted or designed to be capable of performing such method or step or a portion thereof.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided. It will be understood that any description or exemplification of a term anywhere herein may be applied wherever such term appears herein (e.g., in any aspect or embodiment in which such term is relevant) unless indicated or clearly evident otherwise.

What is claimed is:

1. A method for modulating mitochondrial transport of serine in a cell, the method comprising inhibiting expression or activity of sideroflexin 1 (SFXN1) by contacting the cell with a CRISPR/Cas system, RNA interference (RNAi) agent, or antisense agent specific for SFXN1, thereby decreasing the mitochondrial transport of serine in the cell.

2. The method of claim 1, wherein the cell is a human cell and the SFXN1 is human SFXN1.

3. The method of claim 1, wherein inhibiting expression or activity of SFXN1 comprises deleting or mutating the SFXN1 gene.

4. The method of claim 3, wherein the SFXN1 gene is deleted or mutated using a CRISPR/Cas genome editing system.

5. The method of claim 1, wherein the cell is a cancer cell.

6. The method of claim 1, wherein the cell is a blood cancer cell.

7. The method of claim 1, wherein the cell is a mammalian cell.

8. A method of treating a subject in need of treatment for a cancer, the method comprising inhibiting expression or activity of SFXN1 in a cancer cell of the subject by administering a CRISPR/Cas system, RNA interference (RNAi) agent, or antisense agent specific for SFXN1, thereby decreasing mitochondrial transport of serine in the cell, wherein the decrease in mitochondrial transport of serine in the cell reduces the supply of one-carbon units and reduces proliferation of the cell.

9. The method of claim 8, wherein the SFXN1 is human SFXN1 and the subject is human.

10. The method of claim 8, wherein inhibiting expression or activity of SFXN1 comprises administering a CRISPR/Cas system specific for SFXN1 to the subject.

11. The method of claim 8, wherein the cancer cell is a blood cancer cell.

12. The method of claim 1, wherein the method further comprises inhibiting expression or activity of sideroflexin 3 (SFXN3) by contacting the cell with a CRISPR/Cas system, RNA interference (RNAi) agent, or antisense agent specific for SFXN3.

13. The method of claim 12, wherein the cell is a cancer cell.

14. The method of claim 12, wherein the cell is a blood cancer cell.

15. The method of claim 13, wherein the cell is a human cell.

16. The method of claim 8, wherein the method further comprises inhibiting expression or activity of sideroflexin 3 (SFXN3) by administering a CRISPR/Cas system, RNA interference (RNAi) agent, or antisense agent specific for SFXN3.

17. The method of claim 16, wherein the cell is a human cell.

\* \* \* \* \*